United States Patent
Lipscombe et al.

(10) Patent No.: US 6,353,091 B1
(45) Date of Patent: Mar. 5, 2002

(54) HUMAN N-TYPE CALCIUM CHANNEL ISOFORM

(75) Inventors: Diane Lipscombe, Barrington; Stephanie Schorge, Smithfield, both of RI (US)

(73) Assignee: Brown University Research Founddation, Providence, RI (US)

( * ) Notice: Subject to any disclaimer, the term of this patent is extended or adjusted under 35 U.S.C. 154(b) by 0 days.

(21) Appl. No.: 09/268,163

(22) Filed: Mar. 12, 1999

Related U.S. Application Data

(60) Provisional application No. 60/077,901, filed on Mar. 13, 1998.

(51) Int. Cl.$^7$ .............................. C07K 14/00; C07K 5/00
(52) U.S. Cl. ........................................ 530/350; 530/300
(58) Field of Search .................................. 530/300, 350

(56) References Cited

U.S. PATENT DOCUMENTS 5,429,921 A    7/1995   Harpold et al.

FOREIGN PATENT DOCUMENTS

| WO | WO 93/04083 | 3/1993 |
| WO | WO 95/04822 | 2/1995 |
| WO | WO 98/11131 | 3/1998 |

OTHER PUBLICATIONS

Zhang et al., *Nature* 372: 97–100 (1994).
Williams et al., *Science* 257: 389–395 (1992).
Soong et al., *Science* 260: 1133–1136 (1993).
Mintz et al., *Neuron* 9: 85–95 (1992).
Mainen and Sejnowski, *Science* 268: 1503–1509 (1995).
Mathur et al., *J. Gen. Physiol.* 109: 191–199 (1997).
Tang and Papazian, *J. Gen. Physiol.* 109: 301–311 (1997).
Starr et al., *Proc. Natl. Acad. Sci. USA* 89: 5621–5625 (1991).
Yu et al., *Proc. Natl. Acad. Sci. USA* 89: 10494–10498 (1992).
Nakai et al., *Proc. Natl. Acad. Sci. USA* 91: 1014–1018 (1994).
Lin et al., *j. Neuroscience* 19(13): 5322–5331 (1999).
Ligon et al., *J. Biol. Chem.* 273(22): 13905–13911 (1998).
Hines and Carnevale, *Neural Computation* 12: 995–1007 (2000).
Jones and Marks, *J. Gen. Physiol.* 94: 151–167 (1989).
McCarthy and Tanpiengco, *J. Neuroscience* 12: 2225–2234 (1992).
Lin et al., *Neuron* 18: 153–166, 1997.
Sutton et al., *Soc. Neurosci. Abs* 24:21, 1998.
Soong et al., *Science* 260: 1133–1136, 1993.
Lipscombe et al. *Nature* 340:639–642, 1989.

*Primary Examiner*—Sean McGarry
(74) *Attorney, Agent, or Firm*—Wolf, Greenfield & Sacks, P.C.

(57) ABSTRACT

The invention pertains to a human N-type calcium channel isoform, $h\alpha_{1B+SFVG}$, which is involved in central nervous system signaling, and nucleic acids relating thereto. The present invention also includes fragments and biologically functional variants of the human $h\alpha_{1B+SFVG}$ channel. Also included are human N-type calcium channel $h\alpha_{1B+SFVG}$ subunit inhibitors which inhibit human N-type calcium channel $h\alpha_{1B+SFVG}$ subunit activity by inhibiting the expression or function of human N-type calcium channel $h\alpha_{1B+SFVG}$ subunit. The invention further relates to methods of using such nucleic acids, polypeptides, and inhibitors in the treatment and/or diagnosis of disease, such as in methods for treating stroke, pain, e.g., neuropathic pain, and traumatic brain injury.

6 Claims, 3 Drawing Sheets

SEQUENCE LISTING

<160> NUMBER OF SEQ ID NOS: 28

<210> SEQ ID NO 1
<211> LENGTH: 12
<212> TYPE: DNA
<213> ORGANISM: Homo sapiens

<400> SEQUENCE: 1
gagcttcgtg gg                                                                12

<210> SEQ ID NO 2
<211> LENGTH: 4
<212> TYPE: PRT
<213> ORGANISM: Homo sapiens

<400> SEQUENCE: 2

Ser Phe Val Gly
  1

<210> SEQ ID NO 3
<211> LENGTH: 7376
<212> TYPE: DNA
<213> ORGANISM: Homo sapiens
<220> FEATURE:
<221> NAME/KEY: CDS
<222> LOCATION: 146..7174

<400> SEQUENCE: 3

```
gcggcggcgg ctgcggcggt ggggccgggc gaggtccgct gcggtccggg cggctccgtg      60
gctgctccgc tctgagcgcc tggcgcgccc cgcgccctcc ctgccggggc cgctgggccg     120
gggatgcacg cggggcccgg gagcc atg gtc cgc ttc ggg gac gag ctg ggc       172
                            Met Val Arg Phe Gly Asp Glu Leu Gly
                              1               5 ggc cgc tat gga ggc ccc ggc ggc gga gag cgg gcc cgg ggc ggc ggg       220
Gly Arg Tyr Gly Gly Pro Gly Gly Gly Glu Arg Ala Arg Gly Gly Gly
 10              15                  20                  25 gcc ggc ggg gcg ggg ggc ccg ggt ccc ggg ggg ctg cag ccc ggc cag       268
Ala Gly Gly Ala Gly Gly Pro Gly Pro Gly Gly Leu Gln Pro Gly Gln
             30                  35                  40 cgg gtc ctc tac aag caa tcg atc gcg cag cgc gcg cgg acc atg gcg       316
Arg Val Leu Tyr Lys Gln Ser Ile Ala Gln Arg Ala Arg Thr Met Ala
         45                  50                  55 ctg tac aac ccc atc ccg gtc aag cag aac tgc ttc acc gtc aac cgc       364
Leu Tyr Asn Pro Ile Pro Val Lys Gln Asn Cys Phe Thr Val Asn Arg
     60                  65                  70 tcg ctc ttc gtc ttc agc gag gac aac gtc gtc cgc aaa tac gcg aag       412
Ser Leu Phe Val Phe Ser Glu Asp Asn Val Val Arg Lys Tyr Ala Lys
 75                  80                  85 cgc atc acc gag tgg cct cca ttc gag tat atg atc ctg gcc acc atc       460
Arg Ile Thr Glu Trp Pro Pro Phe Glu Tyr Met Ile Leu Ala Thr Ile
         90                  95                 100                 105 atc gcc aac tgc atc gtg ctg gcc ctg gag cag cac ctc cct gat ggg       508
Ile Ala Asn Cys Ile Val Leu Ala Leu Glu Gln His Leu Pro Asp Gly
                110                 115                 120 gac aaa acg ccc atg tcc gag cgg ctg gac gac acg gag ccc tat ttc       556
Asp Lys Thr Pro Met Ser Glu Arg Leu Asp Asp Thr Glu Pro Tyr Phe
            125                 130                 135 atc ggg atc ttt tgc ttc gag gca ggg atc aaa atc atc gct ctg ggc       604
Ile Gly Ile Phe Cys Phe Glu Ala Gly Ile Lys Ile Ile Ala Leu Gly
        140                 145                 150
```

```
ttt gtc ttc cac aag ggc tct tac ctg cgg aac ggc tgg aac gtc atg    652
Phe Val Phe His Lys Gly Ser Tyr Leu Arg Asn Gly Trp Asn Val Met
    155                 160                 165 gac ttc gtg gtc gtc ctc aca ggg atc ctt gcc acg gct gga act gac    700
Asp Phe Val Val Val Leu Thr Gly Ile Leu Ala Thr Ala Gly Thr Asp
170                 175                 180                 185 ttc gac ctg cga aca ctg agg gct gtg cgt gtg ctg agg ccc ctg aag    748
Phe Asp Leu Arg Thr Leu Arg Ala Val Arg Val Leu Arg Pro Leu Lys
                190                 195                 200 ctg gtg tct ggg att cca agt ttg cag gtg gtg ctc aag tcc atc atg    796
Leu Val Ser Gly Ile Pro Ser Leu Gln Val Val Leu Lys Ser Ile Met
            205                 210                 215 aag gcc atg gtt cca ctc ctg cag att ggg ctg ctc ttc ttt gcc        844
Lys Ala Met Val Pro Leu Leu Gln Ile Gly Leu Leu Leu Phe Phe Ala
        220                 225                 230 atc ctc atg ttt gcc atc att ggc ctg gag ttc tac atg ggc aag ttc    892
Ile Leu Met Phe Ala Ile Ile Gly Leu Glu Phe Tyr Met Gly Lys Phe
    235                 240                 245 cac aag gcc tgt ttc ccc aac agc aca gat gcg gag ccc gtg ggt gac    940
His Lys Ala Cys Phe Pro Asn Ser Thr Asp Ala Glu Pro Val Gly Asp
250                 255                 260                 265 ttc ccc tgt ggc aag gag gcc cca gcc cgg ctg tgc gag ggc gac act    988
Phe Pro Cys Gly Lys Glu Ala Pro Ala Arg Leu Cys Glu Gly Asp Thr
                270                 275                 280 gag tgc cgg gag tac tgg cca gga ccc aac ttt ggc atc acc aac ttt   1036
Glu Cys Arg Glu Tyr Trp Pro Gly Pro Asn Phe Gly Ile Thr Asn Phe
            285                 290                 295 gac aat atc ctg ttt gcc atc ttg acg gtg ttc cag tgc atc acc atg   1084
Asp Asn Ile Leu Phe Ala Ile Leu Thr Val Phe Gln Cys Ile Thr Met
        300                 305                 310 gag ggc tgg act gac atc ctc tat aat aca aac gat gcg gcc ggc aac   1132
Glu Gly Trp Thr Asp Ile Leu Tyr Asn Thr Asn Asp Ala Ala Gly Asn
    315                 320                 325 acc tgg aac tgg ctc tac ttc atc cct ctc atc atc atc ggc tcc ttc   1180
Thr Trp Asn Trp Leu Tyr Phe Ile Pro Leu Ile Ile Ile Gly Ser Phe
330                 335                 340                 345 ttc atg ctc aac ctg gtg ctg ggc gtg ctc tcg ggg gag ttt gcc aag   1228
Phe Met Leu Asn Leu Val Leu Gly Val Leu Ser Gly Glu Phe Ala Lys
                350                 355                 360 gag cga gag agg gtg gag aac cgc cgc gcc ttc ctg aag ctg cgc cgg   1276
Glu Arg Glu Arg Val Glu Asn Arg Arg Ala Phe Leu Lys Leu Arg Arg
            365                 370                 375 cag cag cag atc gag cga gag ctc aac ggg tac ctg gag tgg atc ttc   1324
Gln Gln Gln Ile Glu Arg Glu Leu Asn Gly Tyr Leu Glu Trp Ile Phe
        380                 385                 390 aag gcg gag gaa gtc atg ctg gcc gag gag gac agg aat gca gag gag   1372
Lys Ala Glu Glu Val Met Leu Ala Glu Glu Asp Arg Asn Ala Glu Glu
    395                 400                 405 aag tcc cct ttg gac gtg ctg aag aga gcg gcc acc aag aag agc aga   1420
Lys Ser Pro Leu Asp Val Leu Lys Arg Ala Ala Thr Lys Lys Ser Arg
410                 415                 420                 425 aat gac ctg atc cac gca gag gag gga gag gac cgg ttt gca gat ctc   1468
Asn Asp Leu Ile His Ala Glu Glu Gly Glu Asp Arg Phe Ala Asp Leu
                430                 435                 440 tgt gct gtt gga tcc ccc ttc gcc cgc gcc agc ctc aag agc ggg aag   1516
Cys Ala Val Gly Ser Pro Phe Ala Arg Ala Ser Leu Lys Ser Gly Lys
            445                 450                 455 aca gag agc tcg tca tac ttc cgg agg aag gag aag atg ttc cgg ttt   1564
Thr Glu Ser Ser Ser Tyr Phe Arg Arg Lys Glu Lys Met Phe Arg Phe
```

```
                460                 465                 470
ttt atc cgg cgc atg gtg aag gct cag agc ttc tac tgg gtg gtg ctg       1612
Phe Ile Arg Arg Met Val Lys Ala Gln Ser Phe Tyr Trp Val Val Leu
    475                 480                 485 tgc gtg gtg gcc ctg aac aca ctg tgt gtg gcc atg gtg cat tac aac       1660
Cys Val Val Ala Leu Asn Thr Leu Cys Val Ala Met Val His Tyr Asn
490                 495                 500                 505 cag ccg cgg cgg ctt acc acg acc ctg tat ttt gca gag ttt gtt ttc       1708
Gln Pro Arg Arg Leu Thr Thr Thr Leu Tyr Phe Ala Glu Phe Val Phe
                510                 515                 520 ctg ggt ctc ttc ctc aca gag atg tcc ctg aag atg tat ggc ctg ggg       1756
Leu Gly Leu Phe Leu Thr Glu Met Ser Leu Lys Met Tyr Gly Leu Gly
            525                 530                 535 ccc aga agc tac ttc cgg tcc tcc ttc aac tgc ttc gac ttt ggg gtc       1804
Pro Arg Ser Tyr Phe Arg Ser Ser Phe Asn Cys Phe Asp Phe Gly Val
        540                 545                 550 atc gtg ggg agc gtc ttt gaa gtg gtc tgg gcg gcc atc aag ccg gga       1852
Ile Val Gly Ser Val Phe Glu Val Val Trp Ala Ala Ile Lys Pro Gly
    555                 560                 565 agc tcc ttt ggg atc agt gtg ctg cgg gcc ctc cgc ctg ctg agg atc       1900
Ser Ser Phe Gly Ile Ser Val Leu Arg Ala Leu Arg Leu Leu Arg Ile
570                 575                 580                 585 ttc aaa gtc acg aag tac tgg agc tcc ctg cgg aac ctg gtg gtg tcc       1948
Phe Lys Val Thr Lys Tyr Trp Ser Ser Leu Arg Asn Leu Val Val Ser
                590                 595                 600 ctg ctg aac tcc atg aag tcc atc atc agc ctc ctc ttc ttg ctc ttc       1996
Leu Leu Asn Ser Met Lys Ser Ile Ile Ser Leu Leu Phe Leu Leu Phe
            605                 610                 615 ctg ttc att gtg gtc ttc gcc ctg ctg ggg atg cag ctg ttt ggg gga       2044
Leu Phe Ile Val Val Phe Ala Leu Leu Gly Met Gln Leu Phe Gly Gly
        620                 625                 630 cag ttc aac ttc cag gat gag act ccc aca acc aac ttc gac acc ttc       2092
Gln Phe Asn Phe Gln Asp Glu Thr Pro Thr Thr Asn Phe Asp Thr Phe
    635                 640                 645 cct gcc gcc atc ctc act gtc ttc cag atc ctg acg gga gag gac tgg       2140
Pro Ala Ala Ile Leu Thr Val Phe Gln Ile Leu Thr Gly Glu Asp Trp
650                 655                 660                 665 aat gca gtg atg tat cac ggg atc gaa tcg caa ggc ggc gtc agc aaa       2188
Asn Ala Val Met Tyr His Gly Ile Glu Ser Gln Gly Gly Val Ser Lys
                670                 675                 680 ggc atg ttc tcg tcc ttt tac ttc att gtc ctg aca ctg ttc gga aac       2236
Gly Met Phe Ser Ser Phe Tyr Phe Ile Val Leu Thr Leu Phe Gly Asn
            685                 690                 695 tac act ctg ctg aat gtc ttt ctg gcc atc gct gtg gac aac ctg gcc       2284
Tyr Thr Leu Leu Asn Val Phe Leu Ala Ile Ala Val Asp Asn Leu Ala
        700                 705                 710 aac gcc caa gag ctg acc aag gat gaa gag gag atg gaa gaa gca gcc       2332
Asn Ala Gln Glu Leu Thr Lys Asp Glu Glu Glu Met Glu Glu Ala Ala
    715                 720                 725 aat cag aag ctt gct ctg caa aag gcc aaa gaa gtg gct gaa gtc agc       2380
Asn Gln Lys Leu Ala Leu Gln Lys Ala Lys Glu Val Ala Glu Val Ser
730                 735                 740                 745 ccc atg tct gcc gcg aac atc tcc atc gcc gcc agg cag cag aac tcg       2428
Pro Met Ser Ala Ala Asn Ile Ser Ile Ala Ala Arg Gln Gln Asn Ser
                750                 755                 760 gcc aag gcg cgc tcg gtg tgg gag cag cgg gcc agc cag cta cgg ctg       2476
Ala Lys Ala Arg Ser Val Trp Glu Gln Arg Ala Ser Gln Leu Arg Leu
            765                 770                 775 cag aac ctg cgg gcc agc tgc gag gcg ctg tac agc gag atg gac ccc       2524
```

```
Gln Asn Leu Arg Ala Ser Cys Glu Ala Leu Tyr Ser Glu Met Asp Pro
        780                 785                 790 gag gag cgg ctg cgc ttc gcc act acg cgc cac ctg cgg ccc gac atg       2572
Glu Glu Arg Leu Arg Phe Ala Thr Thr Arg His Leu Arg Pro Asp Met
795                 800                 805 aag acg cac ctg gac cgg ccg ctg gtg gtg gag ctg ggc cgc gac ggc       2620
Lys Thr His Leu Asp Arg Pro Leu Val Val Glu Leu Gly Arg Asp Gly
810                 815                 820                 825 gcg cgg ggg ccc gtg gga ggc aaa gcc cga cct gag gct gcg gag gcc       2668
Ala Arg Gly Pro Val Gly Gly Lys Ala Arg Pro Glu Ala Ala Glu Ala
                830                 835                 840 ccc gag ggc gtc gac cct ccg cgc agg cac cac cgg cac cgc gac aag       2716
Pro Glu Gly Val Asp Pro Pro Arg Arg His His Arg His Arg Asp Lys
            845                 850                 855 gac aag acc ccc gcg gcg ggg gac cag gac cga gca gag gcc ccg aag       2764
Asp Lys Thr Pro Ala Ala Gly Asp Gln Asp Arg Ala Glu Ala Pro Lys
        860                 865                 870 gcg gag agc ggg gag ccc ggt gcc cgg gag gag cgg ccg cgg ccg cac       2812
Ala Glu Ser Gly Glu Pro Gly Ala Arg Glu Glu Arg Pro Arg Pro His
875                 880                 885 cgc agc cac agc aag gag gcc gcg ggg ccc ccg gag gcg cgg agc gag       2860
Arg Ser His Ser Lys Glu Ala Ala Gly Pro Pro Glu Ala Arg Ser Glu
890                 895                 900                 905 cgc ggc cga ggc cca ggc ccc gag ggc ggc cgg cgg cac cac cgg cgc       2908
Arg Gly Arg Gly Pro Gly Pro Glu Gly Gly Arg Arg His His Arg Arg
                910                 915                 920 ggc tcc ccg gag gag gcg gcc gag cgg gag ccc cga cgc cac cgc gcg       2956
Gly Ser Pro Glu Glu Ala Ala Glu Arg Glu Pro Arg Arg His Arg Ala
            925                 930                 935 cac cgg cac cag gat ccg agc aag gag tgc gcc ggc gcc aag ggc gag       3004
His Arg His Gln Asp Pro Ser Lys Glu Cys Ala Gly Ala Lys Gly Glu
        940                 945                 950 cgg cgc gcg cgg cac cgc ggc ggc ccc cga gcg ggg ccc cgg gag gcg       3052
Arg Arg Ala Arg His Arg Gly Gly Pro Arg Ala Gly Pro Arg Glu Ala
955                 960                 965 gag agc ggg gag gag ccg gcg cgg cgg cac cgg gcc cgg cac aag gcg       3100
Glu Ser Gly Glu Glu Pro Ala Arg Arg His Arg Ala Arg His Lys Ala
970                 975                 980                 985 cag cct gct cac gag gct gtg gag aag gag acc acg gag aag gag gcc       3148
Gln Pro Ala His Glu Ala Val Glu Lys Glu Thr Thr Glu Lys Glu Ala
                990                 995                 1000 acg gag aag gag gct gag ata gtg gaa gcc gac aag gaa aag gag ctc       3196
Thr Glu Lys Glu Ala Glu Ile Val Glu Ala Asp Lys Glu Lys Glu Leu
            1005                1010                1015 cgg aac cac cag ccc cgg gag cca cac tgt gac ctg gag acc agt ggg       3244
Arg Asn His Gln Pro Arg Glu Pro His Cys Asp Leu Glu Thr Ser Gly
        1020                1025                1030 act gtg act gtg ggt ccc atg cac aca ctg ccc agc acc tgt ctc cag       3292
Thr Val Thr Val Gly Pro Met His Thr Leu Pro Ser Thr Cys Leu Gln
1035                1040                1045 aag gtg gag gaa cag cca gag gat gca gac aat cag cgg aac gtc act       3340
Lys Val Glu Glu Gln Pro Glu Asp Ala Asp Asn Gln Arg Asn Val Thr
1050                1055                1060                1065 cgc atg ggc agt cag ccc cca gac ccg aac act att gta cat atc cca       3388
Arg Met Gly Ser Gln Pro Pro Asp Pro Asn Thr Ile Val His Ile Pro
                1070                1075                1080 gtg atg ctg acg ggc cct ctt ggg gaa gcc acg gtc gtt ccc agt ggt       3436
Val Met Leu Thr Gly Pro Leu Gly Glu Ala Thr Val Val Pro Ser Gly
            1085                1090                1095
```

```
aac gtg gac ctg gaa agc caa gca gag ggg aag aag gag gtg gaa gcg    3484
Asn Val Asp Leu Glu Ser Gln Ala Glu Gly Lys Lys Glu Val Glu Ala
        1100                1105                1110 gat gac gtg atg agg agc ggc ccc cgg cct atc gtc cca tac agc tcc    3532
Asp Asp Val Met Arg Ser Gly Pro Arg Pro Ile Val Pro Tyr Ser Ser
1115                1120                1125 atg ttc tgt tta agc ccc acc aac ctg ctc cgc cgc ttc tgc cac tac    3580
Met Phe Cys Leu Ser Pro Thr Asn Leu Leu Arg Arg Phe Cys His Tyr
1130                1135                1140                1145 atc gtg acc atg agg tac ttc gag gtg gtc att ctc gtg gtc atc gcc    3628
Ile Val Thr Met Arg Tyr Phe Glu Val Val Ile Leu Val Val Ile Ala
                1150                1155                1160 ttg agc agc atc gcc ctg gct gct gag gac cca gtg cgc aca gac tcg    3676
Leu Ser Ser Ile Ala Leu Ala Ala Glu Asp Pro Val Arg Thr Asp Ser
        1165                1170                1175 ccc agg aac aac gct ctg aaa tac ctg gat tac att ttc act ggt gtc    3724
Pro Arg Asn Asn Ala Leu Lys Tyr Leu Asp Tyr Ile Phe Thr Gly Val
1180                1185                1190 ttt acc ttt gag atg gtg ata aag atg atc gac ttg gga ctg ctg ctt    3772
Phe Thr Phe Glu Met Val Ile Lys Met Ile Asp Leu Gly Leu Leu Leu
1195                1200                1205 cac cct gga gcc tat ttc cgg gac ttg tgg aac att ctg gac ttc att    3820
His Pro Gly Ala Tyr Phe Arg Asp Leu Trp Asn Ile Leu Asp Phe Ile
1210                1215                1220                1225 gtg gtc agt ggc gcc ctg gtg gcg ttt gct ttc tcg agc ttc gtg gga    3868
Val Val Ser Gly Ala Leu Val Ala Phe Ala Phe Ser Ser Phe Val Gly
        1230                1235                1240 gga tcc aaa ggg aaa gac atc aat acc atc aag tct ctg aga gtc ctt    3916
Gly Ser Lys Gly Lys Asp Ile Asn Thr Ile Lys Ser Leu Arg Val Leu
1245                1250                1255 cgt gtc ctg cgg ccc ctc aag acc atc aaa cgg ctg ccc aag ctc aag    3964
Arg Val Leu Arg Pro Leu Lys Thr Ile Lys Arg Leu Pro Lys Leu Lys
        1260                1265                1270 gct gtg ttt gac tgt gtg gtg aac tcc ctg aag aat gtc ctc aac atc    4012
Ala Val Phe Asp Cys Val Val Asn Ser Leu Lys Asn Val Leu Asn Ile
1275                1280                1285 ttg att gtc tac atg ctc ttc atg ttc ata ttt gcc gtc att gcg gtg    4060
Leu Ile Val Tyr Met Leu Phe Met Phe Ile Phe Ala Val Ile Ala Val
1290                1295                1300                1305 cag ctc ttc aaa ggg aag ttt ttc tac tgc aca gat gaa tcc aag gag    4108
Gln Leu Phe Lys Gly Lys Phe Phe Tyr Cys Thr Asp Glu Ser Lys Glu
        1310                1315                1320 ctg gag agg gac tgc agg ggt cag tat ttg gat tat gag aag gag gaa    4156
Leu Glu Arg Asp Cys Arg Gly Gln Tyr Leu Asp Tyr Glu Lys Glu Glu
1325                1330                1335 gtg gaa gct cag ccc agg cag tgg aag aaa tac gac ttt cac tac gac    4204
Val Glu Ala Gln Pro Arg Gln Trp Lys Lys Tyr Asp Phe His Tyr Asp
        1340                1345                1350 aat gtg ctc tgg gct ctg ctg acg ctg ttc aca gtg tcc acg gga gaa    4252
Asn Val Leu Trp Ala Leu Leu Thr Leu Phe Thr Val Ser Thr Gly Glu
        1355                1360                1365 ggc tgg ccc atg gtg ctg aaa cac tcc gtg gat gcc acc tat gag gag    4300
Gly Trp Pro Met Val Leu Lys His Ser Val Asp Ala Thr Tyr Glu Glu
1370                1375                1380                1385 cag ggt cca agc cct ggg tac cgc atg gag ctg tcc atc ttc tac gtg    4348
Gln Gly Pro Ser Pro Gly Tyr Arg Met Glu Leu Ser Ile Phe Tyr Val
        1390                1395                1400 gtc tac ttt gtg gtc ttt ccc ttc ttc ttc gtg aac atc ttt gtg gct    4396
Val Tyr Phe Val Val Phe Pro Phe Phe Phe Val Asn Ile Phe Val Ala
1405                1410                1415
```

```
ttg atc atc atc acc ttc cag gag cag ggg gac aag gtg atg tct gaa    4444
Leu Ile Ile Ile Thr Phe Gln Glu Gln Gly Asp Lys Val Met Ser Glu
        1420                1425                1430 tgc agc ctg gag aag aac gag agg gct tgc att gac ttc gcc atc agc    4492
Cys Ser Leu Glu Lys Asn Glu Arg Ala Cys Ile Asp Phe Ala Ile Ser
    1435                1440                1445 gcc aaa ccc ctg aca cgg tac atg ccc caa aac cgg cag tcg ttc cag    4540
Ala Lys Pro Leu Thr Arg Tyr Met Pro Gln Asn Arg Gln Ser Phe Gln
1450                1455                1460                1465 tat aag acg tgg aca ttt gtg gtc tcc ccg ccc ttt gaa tac ttc atc    4588
Tyr Lys Thr Trp Thr Phe Val Val Ser Pro Pro Phe Glu Tyr Phe Ile
        1470                1475                1480 atg gcc atg ata gcc ctc aac act gtg gtg ctg atg atg aag ttc tat    4636
Met Ala Met Ile Ala Leu Asn Thr Val Val Leu Met Met Lys Phe Tyr
        1485                1490                1495 gat gca ccc tat gag tac gag ctg atg ctg aaa tgc ctg aac atc gtg    4684
Asp Ala Pro Tyr Glu Tyr Glu Leu Met Leu Lys Cys Leu Asn Ile Val
        1500                1505                1510 ttc aca tcc atg ttc tcc atg gaa tgc gtg ctg aag atc atc gcc ttt    4732
Phe Thr Ser Met Phe Ser Met Glu Cys Val Leu Lys Ile Ile Ala Phe
        1515                1520                1525 ggg gtg ctg aac tat ttc aga gat gcc tgg aat gtc ttt gac ttt gtc    4780
Gly Val Leu Asn Tyr Phe Arg Asp Ala Trp Asn Val Phe Asp Phe Val
1530                1535                1540                1545 act gtg ttg gga agt att act gat att tta gta aca gag att gcg gaa    4828
Thr Val Leu Gly Ser Ile Thr Asp Ile Leu Val Thr Glu Ile Ala Glu
        1550                1555                1560 acg aac aat ttc atc aac ctc agc ttc ctc cgc ctc ttt cga gct gcg    4876
Thr Asn Asn Phe Ile Asn Leu Ser Phe Leu Arg Leu Phe Arg Ala Ala
        1565                1570                1575 cgg ctg atc aag ctg ctc cgc cag ggc tac acc atc cgc atc ctg ctg    4924
Arg Leu Ile Lys Leu Leu Arg Gln Gly Tyr Thr Ile Arg Ile Leu Leu
        1580                1585                1590 tgg acc ttt gtc cag tcc ttc aag gcc ctg ccc tac gtg tgt ctg ctc    4972
Trp Thr Phe Val Gln Ser Phe Lys Ala Leu Pro Tyr Val Cys Leu Leu
    1595                1600                1605 att gcc atg ctg ttc ttc atc tac gcc atc atc ggc atg cag gtg ttt    5020
Ile Ala Met Leu Phe Phe Ile Tyr Ala Ile Ile Gly Met Gln Val Phe
1610                1615                1620                1625 ggg aat att gcc ctg gat gat gac acc agc atc aac cgc cac aac aac    5068
Gly Asn Ile Ala Leu Asp Asp Asp Thr Ser Ile Asn Arg His Asn Asn
        1630                1635                1640 ttc cgg acg ttt ttg caa gcc ctg atg ctg ctg ttc agg agc gcc acg    5116
Phe Arg Thr Phe Leu Gln Ala Leu Met Leu Leu Phe Arg Ser Ala Thr
        1645                1650                1655 ggg gag gcc tgg cac gag atc atg ctg tcc tgc ctg agc aac cag gcc    5164
Gly Glu Ala Trp His Glu Ile Met Leu Ser Cys Leu Ser Asn Gln Ala
        1660                1665                1670 tgt gat gag cag gcc aat gcc acc gag tgt gga agt gac ttt gcc tac    5212
Cys Asp Glu Gln Ala Asn Ala Thr Glu Cys Gly Ser Asp Phe Ala Tyr
        1675                1680                1685 ttc tac ttc gtc tcc ttc atc ttc ctg tgc tcc ttt ctg atg ttg aac    5260
Phe Tyr Phe Val Ser Phe Ile Phe Leu Cys Ser Phe Leu Met Leu Asn
1690                1695                1700                1705 ctc ttt gtg gct gtg atc atg gac aat ttt gag tac ctc acg cgg gac    5308
Leu Phe Val Ala Val Ile Met Asp Asn Phe Glu Tyr Leu Thr Arg Asp
        1710                1715                1720 tct tcc atc cta ggt cct cac cac ttg gat gag ttc atc cgg gtc tgg    5356
Ser Ser Ile Leu Gly Pro His His Leu Asp Glu Phe Ile Arg Val Trp
```

-continued

|  |  |  |  |
|---|---|---|---|
| 1725 | 1730 | 1735 | |
| gct gaa tac gac ccg gct gcg tgt ggg cgc atc agt tac aat gac atg<br>Ala Glu Tyr Asp Pro Ala Ala Cys Gly Arg Ile Ser Tyr Asn Asp Met<br>    1740            1745            1750 | | | 5404 |
| ttt gag atg ctg aaa cac atg tcc ccg cct ctg ggg ctg ggg aag aaa<br>Phe Glu Met Leu Lys His Met Ser Pro Pro Leu Gly Leu Gly Lys Lys<br>1755            1760            1765 | | | 5452 |
| tgc cct gct cga gtt gct tac aag cgc ctg gtt cgc atg aac atg ccc<br>Cys Pro Ala Arg Val Ala Tyr Lys Arg Leu Val Arg Met Asn Met Pro<br>1770            1775            1780            1785 | | | 5500 |
| atc tcc aac gag gac atg act gtt cac ttc acg tcc acg ctg atg gcc<br>Ile Ser Asn Glu Asp Met Thr Val His Phe Thr Ser Thr Leu Met Ala<br>        1790            1795            1800 | | | 5548 |
| ctc atc cgg acg gca ctg gag atc aag ctg gcc cca gct ggg aca aag<br>Leu Ile Arg Thr Ala Leu Glu Ile Lys Leu Ala Pro Ala Gly Thr Lys<br>    1805            1810            1815 | | | 5596 |
| cag cat cag tgt gac gcg gag ttg agg aag gag att tcc gtt gtg tgg<br>Gln His Gln Cys Asp Ala Glu Leu Arg Lys Glu Ile Ser Val Val Trp<br>1820            1825            1830 | | | 5644 |
| gcc aat ctg ccc cag aag act ttg gac ttg ctg gta cca ccc cat aag<br>Ala Asn Leu Pro Gln Lys Thr Leu Asp Leu Leu Val Pro Pro His Lys<br>1835            1840            1845 | | | 5692 |
| cct gat gag atg aca gtg ggg aag gtt tat gca gct ctg atg ata ttt<br>Pro Asp Glu Met Thr Val Gly Lys Val Tyr Ala Ala Leu Met Ile Phe<br>1850            1855            1860            1865 | | | 5740 |
| gac ttc tac aag cag aac aaa acc acc aga gac cag atg cag cag gct<br>Asp Phe Tyr Lys Gln Asn Lys Thr Thr Arg Asp Gln Met Gln Gln Ala<br>        1870            1875            1880 | | | 5788 |
| cct gga ggc ctc tcc cag atg ggt cct gtg tcc ctg ttc cac cct ctg<br>Pro Gly Gly Leu Ser Gln Met Gly Pro Val Ser Leu Phe His Pro Leu<br>    1885            1890            1895 | | | 5836 |
| aag gcc acc ctg gag cag aca cag ccg gct gtg ctc cga gga gcc cgg<br>Lys Ala Thr Leu Glu Gln Thr Gln Pro Ala Val Leu Arg Gly Ala Arg<br>1900            1905            1910 | | | 5884 |
| gtt ttc ctt cga cag aag agt tcc acc tcc ctc agc aat ggc ggg gcc<br>Val Phe Leu Arg Gln Lys Ser Ser Thr Ser Leu Ser Asn Gly Gly Ala<br>    1915            1920            1925 | | | 5932 |
| ata caa aac caa gag agt ggc atc aaa gag tct gtc tcc tgg ggc act<br>Ile Gln Asn Gln Glu Ser Gly Ile Lys Glu Ser Val Ser Trp Gly Thr<br>1930            1935            1940            1945 | | | 5980 |
| caa agg acc cag gat gca ccc cat gag gcc agg cca ccc ctg gag cgt<br>Gln Arg Thr Gln Asp Ala Pro His Glu Ala Arg Pro Pro Leu Glu Arg<br>        1950            1955            1960 | | | 6028 |
| ggc cac tcc aca gag atc cct gtg ggg cgg tca gga gca ctg gct gtg<br>Gly His Ser Thr Glu Ile Pro Val Gly Arg Ser Gly Ala Leu Ala Val<br>    1965            1970            1975 | | | 6076 |
| gac gtt cag atg cag agc ata acc cgg agg ggc cct gat ggg gag ccc<br>Asp Val Gln Met Gln Ser Ile Thr Arg Arg Gly Pro Asp Gly Glu Pro<br>1980            1985            1990 | | | 6124 |
| cag cct ggg ctg gag agc cag ggt cga gcg gcc tcc atg ccc cgc ctt<br>Gln Pro Gly Leu Glu Ser Gln Gly Arg Ala Ala Ser Met Pro Arg Leu<br>    1995            2000            2005 | | | 6172 |
| gcg gcc gag act cag ccc gtc aca gat gcc agc ccc atg aag cgc tcc<br>Ala Ala Glu Thr Gln Pro Val Thr Asp Ala Ser Pro Met Lys Arg Ser<br>2010            2015            2020            2025 | | | 6220 |
| atc tcc acg ctg gcc cag cgg ccc cgt ggg act cat ctt tgc agc acc<br>Ile Ser Thr Leu Ala Gln Arg Pro Arg Gly Thr His Leu Cys Ser Thr<br>        2030            2035            2040 | | | 6268 |
| acc ccg gac cgc cca ccc cct agc cag gcg tcg tcg cac cac cac cac | | | 6316 |

```
Thr Pro Asp Arg Pro Pro Pro Ser Gln Ala Ser Ser His His His His
        2045                2050                2055 cac cgc tgc cac cgc cgc agg gac agg aag cag agg tcc ctg gag aag      6364
His Arg Cys His Arg Arg Arg Asp Arg Lys Gln Arg Ser Leu Glu Lys
2060                2065                2070 ggg ccc agc ctg tct gcc gat atg gat ggc gca cca agc agt gct gtg      6412
Gly Pro Ser Leu Ser Ala Asp Met Asp Gly Ala Pro Ser Ser Ala Val
        2075                2080                2085 ggg ccg ggg ctg ccc ccg gga gag ggg cct aca ggc tgc cgg cgg gaa      6460
Gly Pro Gly Leu Pro Pro Gly Glu Gly Pro Thr Gly Cys Arg Arg Glu
2090                2095                2100                2105 cga gag cgc cgg cag gag cgg ggc cgg tcc cag gag cgg agg cag ccc      6508
Arg Glu Arg Arg Gln Glu Arg Gly Arg Ser Gln Glu Arg Arg Gln Pro
                2110                2115                2120 tca tcc tcc tcc tcg gag aag cag cgc ttc tac tcc tgc gac cgc ttt      6556
Ser Ser Ser Ser Ser Glu Lys Gln Arg Phe Tyr Ser Cys Asp Arg Phe
            2125                2130                2135 ggg ggc cgt gag ccc ccg aag ccc aag ccc tcc ctc agc agc cac cca      6604
Gly Gly Arg Glu Pro Pro Lys Pro Lys Pro Ser Leu Ser Ser His Pro
        2140                2145                2150 acg tcg cca aca gct ggc cag gag ccg gga ccc cac cca cag ggc agt      6652
Thr Ser Pro Thr Ala Gly Gln Glu Pro Gly Pro His Pro Gln Gly Ser
    2155                2160                2165 ggt tcc gtg aat ggg agc ccc ttg ctg tca aca tct ggt gct agc acc      6700
Gly Ser Val Asn Gly Ser Pro Leu Leu Ser Thr Ser Gly Ala Ser Thr
2170                2175                2180                2185 ccc ggc cgc ggt ggg cgg agg cag ctc ccc cag acg ccc ctg act ccc      6748
Pro Gly Arg Gly Gly Arg Arg Gln Leu Pro Gln Thr Pro Leu Thr Pro
                2190                2195                2200 cgc ccc agc atc acc tac aag acg gcc aac tcc tca ccc atc cac ttc      6796
Arg Pro Ser Ile Thr Tyr Lys Thr Ala Asn Ser Ser Pro Ile His Phe
            2205                2210                2215 gcc ggg gct cag acc agc ctc cct gcc ttc tcc cca ggc cgg ctc agc      6844
Ala Gly Ala Gln Thr Ser Leu Pro Ala Phe Ser Pro Gly Arg Leu Ser
        2220                2225                2230 cgt ggg ctt tcc gaa cac aac gcc ctg ctg cag aga gac ccc ctc agc      6892
Arg Gly Leu Ser Glu His Asn Ala Leu Leu Gln Arg Asp Pro Leu Ser
    2235                2240                2245 cag ccc ctg gcc cct ggc tct cga att ggc tct gac cct tac ctg ggg      6940
Gln Pro Leu Ala Pro Gly Ser Arg Ile Gly Ser Asp Pro Tyr Leu Gly
2250                2255                2260                2265 cag cgt ctg gac agt gag gcc tct gtc cac gcc ctg cct gag gac acg      6988
Gln Arg Leu Asp Ser Glu Ala Ser Val His Ala Leu Pro Glu Asp Thr
                2270                2275                2280 ctc act ttc gag gag gct gtg gcc acc aac tcg ggc cgc tcc tcc agg      7036
Leu Thr Phe Glu Glu Ala Val Ala Thr Asn Ser Gly Arg Ser Ser Arg
            2285                2290                2295 act tcc tac gtg tcc tcc ctg acc tcc cag tct cac cct ctc cgc cgc      7084
Thr Ser Tyr Val Ser Ser Leu Thr Ser Gln Ser His Pro Leu Arg Arg
        2300                2305                2310 gtg ccc aac ggt tac cac tgc acc ctg gga ctc agc tcg ggt ggc cga      7132
Val Pro Asn Gly Tyr His Cys Thr Leu Gly Leu Ser Ser Gly Gly Arg
    2315                2320                2325 gca cgg cac agc tac cac cac cct gac caa gac cac tgg tgc tagctgcac    7183
Ala Arg His Ser Tyr His His Pro Asp Gln Asp His Trp Cys
2330                2335                2340 cgtgaccgct cagacgcctg catgcagcag gcgtgtgttc cagtggatga gttttatcat    7243
ccacacgggg cagtcggccc tcgggggagg ccttgcccac cttggtgagg ctcctgtggc    7303
```

```
ccctccctcc ccctcctccc ctcttttact ctagacgacg aataaagccc tgttgcttga    7363
gtgtacgtac cgc                                                       7376
```

<210> SEQ ID NO 4
<211> LENGTH: 2343
<212> TYPE: PRT
<213> ORGANISM: Homo sapiens

<400> SEQUENCE: 4

```
Met Val Arg Phe Gly Asp Glu Leu Gly Gly Arg Tyr Gly Gly Pro Gly
 1               5                   10                  15

Gly Gly Glu Arg Ala Arg Gly Gly Ala Gly Ala Gly Gly Pro
            20                  25                  30

Gly Pro Gly Gly Leu Gln Pro Gly Gln Arg Val Leu Tyr Lys Gln Ser
         35                  40                  45

Ile Ala Gln Arg Ala Arg Thr Met Ala Leu Tyr Asn Pro Ile Pro Val
     50                  55                  60

Lys Gln Asn Cys Phe Thr Val Asn Arg Ser Leu Phe Val Phe Ser Glu
 65                  70                  75                  80

Asp Asn Val Val Arg Lys Tyr Ala Lys Arg Ile Thr Glu Trp Pro Pro
                 85                  90                  95

Phe Glu Tyr Met Ile Leu Ala Thr Ile Ile Ala Asn Cys Ile Val Leu
            100                 105                 110

Ala Leu Glu Gln His Leu Pro Asp Gly Asp Lys Thr Pro Met Ser Glu
        115                 120                 125

Arg Leu Asp Asp Thr Glu Pro Tyr Phe Ile Gly Ile Phe Cys Phe Glu
    130                 135                 140

Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Leu Thr
                165                 170                 175

Gly Ile Leu Ala Thr Ala Gly Thr Asp Phe Asp Leu Arg Thr Leu Arg
            180                 185                 190

Ala Val Arg Val Leu Arg Pro Leu Lys Leu Val Ser Gly Ile Pro Ser
        195                 200                 205

Leu Gln Val Val Leu Lys Ser Ile Met Lys Ala Met Val Pro Leu Leu
    210                 215                 220

Gln Ile Gly Leu Leu Phe Phe Ala Ile Leu Met Phe Ala Ile Ile
225                 230                 235                 240

Gly Leu Glu Phe Tyr Met Gly Lys Phe His Lys Ala Cys Phe Pro Asn
                245                 250                 255

Ser Thr Asp Ala Glu Pro Val Gly Asp Phe Pro Cys Gly Lys Glu Ala
            260                 265                 270

Pro Ala Arg Leu Cys Glu Gly Asp Thr Glu Cys Arg Glu Tyr Trp Pro
        275                 280                 285

Gly Pro Asn Phe Gly Ile Thr Asn Phe Asp Asn Ile Leu Phe Ala Ile
    290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                325                 330                 335

Ile Pro Leu Ile Ile Ile Gly Ser Phe Phe Met Leu Asn Leu Val Leu
            340                 345                 350

Gly Val Leu Ser Gly Glu Phe Ala Lys Glu Arg Glu Arg Val Glu Asn
```

-continued

```
                355                 360                 365
Arg Arg Ala Phe Leu Lys Leu Arg Arg Gln Gln Gln Ile Glu Arg Glu
    370                 375                 380

Leu Asn Gly Tyr Leu Glu Trp Ile Phe Lys Ala Glu Glu Val Met Leu
385                 390                 395                 400

Ala Glu Glu Asp Arg Asn Ala Glu Glu Lys Ser Pro Leu Asp Val Leu
                405                 410                 415

Lys Arg Ala Ala Thr Lys Lys Ser Arg Asn Asp Leu Ile His Ala Glu
                420                 425                 430

Glu Gly Glu Asp Arg Phe Ala Asp Leu Cys Ala Val Gly Ser Pro Phe
            435                 440                 445

Ala Arg Ala Ser Leu Lys Ser Gly Lys Thr Glu Ser Ser Ser Tyr Phe
450                 455                 460

Arg Arg Lys Glu Lys Met Phe Arg Phe Phe Ile Arg Arg Met Val Lys
465                 470                 475                 480

Ala Gln Ser Phe Tyr Trp Val Val Leu Cys Val Val Ala Leu Asn Thr
                485                 490                 495

Leu Cys Val Ala Met Val His Tyr Asn Gln Pro Arg Arg Leu Thr Thr
            500                 505                 510

Thr Leu Tyr Phe Ala Glu Phe Val Phe Leu Gly Leu Phe Leu Thr Glu
            515                 520                 525

Met Ser Leu Lys Met Tyr Gly Leu Gly Pro Arg Ser Tyr Phe Arg Ser
530                 535                 540

Ser Phe Asn Cys Phe Asp Phe Gly Val Ile Val Gly Ser Val Phe Glu
545                 550                 555                 560

Val Val Trp Ala Ala Ile Lys Pro Gly Ser Ser Phe Gly Ile Ser Val
                565                 570                 575

Leu Arg Ala Leu Arg Leu Leu Arg Ile Phe Lys Val Thr Lys Tyr Trp
            580                 585                 590

Ser Ser Leu Arg Asn Leu Val Val Ser Leu Leu Asn Ser Met Lys Ser
            595                 600                 605

Ile Ile Ser Leu Leu Phe Leu Leu Phe Leu Phe Ile Val Val Phe Ala
610                 615                 620

Leu Leu Gly Met Gln Leu Phe Gly Gly Gln Phe Asn Phe Gln Asp Glu
625                 630                 635                 640

Thr Pro Thr Thr Asn Phe Asp Thr Phe Pro Ala Ala Ile Leu Thr Val
                645                 650                 655

Phe Gln Ile Leu Thr Gly Glu Asp Trp Asn Ala Val Met Tyr His Gly
            660                 665                 670

Ile Glu Ser Gln Gly Gly Val Ser Lys Gly Met Phe Ser Ser Phe Tyr
            675                 680                 685

Phe Ile Val Leu Thr Leu Phe Gly Asn Tyr Thr Leu Leu Asn Val Phe
690                 695                 700

Leu Ala Ile Ala Val Asp Asn Leu Ala Asn Ala Gln Glu Leu Thr Lys
705                 710                 715                 720

Asp Glu Glu Glu Met Glu Glu Ala Ala Asn Gln Lys Leu Ala Leu Gln
                725                 730                 735

Lys Ala Lys Glu Val Ala Glu Val Ser Pro Met Ser Ala Ala Asn Ile
            740                 745                 750

Ser Ile Ala Ala Arg Gln Gln Asn Ser Ala Lys Ala Arg Ser Val Trp
            755                 760                 765

Glu Gln Arg Ala Ser Gln Leu Arg Leu Gln Asn Leu Arg Ala Ser Cys
770                 775                 780
```

-continued

Glu Ala Leu Tyr Ser Glu Met Asp Pro Glu Arg Leu Arg Phe Ala
785                 790                 795                 800

Thr Thr Arg His Leu Arg Pro Asp Met Lys Thr His Leu Asp Arg Pro
            805                 810                 815

Leu Val Val Glu Leu Gly Arg Asp Gly Ala Arg Gly Pro Val Gly Gly
            820                 825                 830

Lys Ala Arg Pro Glu Ala Ala Glu Ala Pro Glu Gly Val Asp Pro Pro
            835                 840                 845

Arg Arg His His Arg His Arg Asp Lys Asp Lys Thr Pro Ala Ala Gly
            850                 855                 860

Asp Gln Asp Arg Ala Glu Ala Pro Lys Ala Glu Ser Gly Glu Pro Gly
865                 870                 875                 880

Ala Arg Glu Glu Arg Pro Arg Pro His Arg Ser His Ser Lys Glu Ala
            885                 890                 895

Ala Gly Pro Pro Glu Ala Arg Ser Glu Arg Gly Arg Gly Pro Gly Pro
            900                 905                 910

Glu Gly Gly Arg Arg His His Arg Arg Gly Ser Pro Glu Glu Ala Ala
            915                 920                 925

Glu Arg Glu Pro Arg Arg His Arg Ala His Arg His Gln Asp Pro Ser
            930                 935                 940

Lys Glu Cys Ala Gly Ala Lys Gly Glu Arg Arg Ala Arg His Arg Gly
945                 950                 955                 960

Gly Pro Arg Ala Gly Pro Arg Glu Ala Glu Ser Gly Glu Glu Pro Ala
            965                 970                 975

Arg Arg His Arg Ala Arg His Lys Ala Gln Pro Ala His Glu Ala Val
            980                 985                 990

Glu Lys Glu Thr Thr Glu Lys Glu Ala Thr Glu Lys Glu Ala Glu Ile
            995                 1000                1005

Val Glu Ala Asp Lys Glu Lys Glu Leu Arg Asn His Gln Pro Arg Glu
            1010                1015                1020

Pro His Cys Asp Leu Glu Thr Ser Gly Thr Val Thr Val Gly Pro Met
1025                1030                1035                1040

His Thr Leu Pro Ser Thr Cys Leu Gln Lys Val Glu Glu Gln Pro Glu
            1045                1050                1055

Asp Ala Asp Asn Gln Arg Asn Val Thr Arg Met Gly Ser Gln Pro Pro
            1060                1065                1070

Asp Pro Asn Thr Ile Val His Ile Pro Val Met Leu Thr Gly Pro Leu
            1075                1080                1085

Gly Glu Ala Thr Val Pro Ser Gly Asn Val Asp Leu Glu Ser Gln
            1090                1095                1100

Ala Glu Gly Lys Lys Glu Val Glu Ala Asp Asp Val Met Arg Ser Gly
1105                1110                1115                1120

Pro Arg Pro Ile Val Pro Tyr Ser Ser Met Phe Cys Leu Ser Pro Thr
            1125                1130                1135

Asn Leu Leu Arg Arg Phe Cys His Tyr Ile Val Thr Met Arg Tyr Phe
            1140                1145                1150

Glu Val Val Ile Leu Val Val Ile Ala Leu Ser Ser Ile Ala Leu Ala
            1155                1160                1165

Ala Glu Asp Pro Val Arg Thr Asp Ser Pro Arg Asn Asn Ala Leu Lys
            1170                1175                1180

Tyr Leu Asp Tyr Ile Phe Thr Gly Val Phe Thr Phe Glu Met Val Ile
            1185                1190                1195                1200

-continued

```
Lys Met Ile Asp Leu Gly Leu Leu His Pro Gly Ala Tyr Phe Arg
            1205                1210                1215
Asp Leu Trp Asn Ile Leu Asp Phe Ile Val Ser Gly Ala Leu Val
            1220                1225                1230
Ala Phe Ala Phe Ser Ser Phe Val Gly Gly Ser Lys Gly Lys Asp Ile
            1235                1240                1245
Asn Thr Ile Lys Ser Leu Arg Val Leu Arg Val Leu Arg Pro Leu Lys
    1250                1255                1260
Thr Ile Lys Arg Leu Pro Lys Leu Lys Ala Val Phe Asp Cys Val Val
1265                1270                1275                1280
Asn Ser Leu Lys Asn Val Leu Asn Ile Leu Ile Val Tyr Met Leu Phe
            1285                1290                1295
Met Phe Ile Phe Ala Val Ile Ala Val Gln Leu Phe Lys Gly Lys Phe
            1300                1305                1310
Phe Tyr Cys Thr Asp Glu Ser Lys Glu Leu Glu Arg Asp Cys Arg Gly
            1315                1320                1325
Gln Tyr Leu Asp Tyr Glu Lys Glu Glu Val Glu Ala Gln Pro Arg Gln
            1330                1335                1340
Trp Lys Lys Tyr Asp Phe His Tyr Asp Asn Val Leu Trp Ala Leu Leu
1345                1350                1355                1360
Thr Leu Phe Thr Val Ser Thr Gly Glu Gly Trp Pro Met Val Leu Lys
            1365                1370                1375
His Ser Val Asp Ala Thr Tyr Glu Glu Gln Gly Pro Ser Pro Gly Tyr
            1380                1385                1390
Arg Met Glu Leu Ser Ile Phe Tyr Val Val Tyr Phe Val Val Phe Pro
            1395                1400                1405
Phe Phe Phe Val Asn Ile Phe Val Ala Leu Ile Ile Ile Thr Phe Gln
    1410                1415                1420
Glu Gln Gly Asp Lys Val Met Ser Glu Cys Ser Leu Glu Lys Asn Glu
1425                1430                1435                1440
Arg Ala Cys Ile Asp Phe Ala Ile Ser Ala Lys Pro Leu Thr Arg Tyr
            1445                1450                1455
Met Pro Gln Asn Arg Gln Ser Phe Gln Tyr Lys Thr Trp Thr Phe Val
            1460                1465                1470
Val Ser Pro Pro Phe Glu Tyr Phe Ile Met Ala Met Ile Ala Leu Asn
            1475                1480                1485
Thr Val Val Leu Met Met Lys Phe Tyr Asp Ala Pro Tyr Glu Tyr Glu
            1490                1495                1500
Leu Met Leu Lys Cys Leu Asn Ile Val Phe Thr Ser Met Phe Ser Met
1505                1510                1515                1520
Glu Cys Val Leu Lys Ile Ile Ala Phe Gly Val Leu Asn Tyr Phe Arg
            1525                1530                1535
Asp Ala Trp Asn Val Phe Asp Phe Val Thr Val Leu Gly Ser Ile Thr
            1540                1545                1550
Asp Ile Leu Val Thr Glu Ile Ala Glu Thr Asn Asn Phe Ile Asn Leu
            1555                1560                1565
Ser Phe Leu Arg Leu Phe Arg Ala Ala Arg Leu Ile Lys Leu Leu Arg
    1570                1575                1580
Gln Gly Tyr Thr Ile Arg Ile Leu Leu Trp Thr Phe Val Gln Ser Phe
1585                1590                1595                1600
Lys Ala Leu Pro Tyr Val Cys Leu Leu Ile Ala Met Leu Phe Phe Ile
            1605                1610                1615
Tyr Ala Ile Ile Gly Met Gln Val Phe Gly Asn Ile Ala Leu Asp Asp
```

-continued

Asp Thr Ser Ile Asn Arg His Asn Asn Phe Arg Thr Phe Leu Gln Ala
1620              1625              1630

Leu Met Leu Leu Phe Arg Ser Ala Thr Gly Glu Ala Trp His Glu Ile
1635              1640              1645

Met Leu Ser Cys Leu Ser Asn Gln Ala Cys Asp Glu Gln Ala Asn Ala
1650              1655              1660

Thr Glu Cys Gly Ser Asp Phe Ala Tyr Phe Tyr Phe Val Ser Phe Ile
1665              1670              1675              1680

Phe Leu Cys Ser Phe Leu Met Leu Asn Leu Phe Val Ala Val Ile Met
    1685              1690              1695

Asp Asn Phe Glu Tyr Leu Thr Arg Asp Ser Ser Ile Leu Gly Pro His
1700              1705              1710

His Leu Asp Glu Phe Ile Arg Val Trp Ala Glu Tyr Asp Pro Ala Ala
1715              1720              1725

Cys Gly Arg Ile Ser Tyr Asn Asp Met Phe Glu Met Leu Lys His Met
1730              1735              1740

Ser Pro Pro Leu Gly Leu Gly Lys Lys Cys Pro Ala Arg Val Ala Tyr
1745              1750              1755              1760

Lys Arg Leu Val Arg Met Asn Met Pro Ile Ser Asn Glu Asp Met Thr
    1765              1770              1775

Val His Phe Thr Ser Thr Leu Met Ala Leu Ile Arg Thr Ala Leu Glu
1780              1785              1790

Ile Lys Leu Ala Pro Ala Gly Thr Lys Gln His Gln Cys Asp Ala Glu
    1795              1800              1805

Leu Arg Lys Glu Ile Ser Val Val Trp Ala Asn Leu Pro Gln Lys Thr
1810              1815              1820

Leu Asp Leu Leu Val Pro Pro His Lys Pro Asp Glu Met Thr Val Gly
1825              1830              1835              1840

Lys Val Tyr Ala Ala Leu Met Ile Phe Asp Phe Tyr Lys Gln Asn Lys
    1845              1850              1855

Thr Thr Arg Asp Gln Met Gln Gln Ala Pro Gly Gly Leu Ser Gln Met
1860              1865              1870

Gly Pro Val Ser Leu Phe His Pro Leu Lys Ala Thr Leu Glu Gln Thr
    1875              1880              1885

Gln Pro Ala Val Leu Arg Gly Ala Arg Val Phe Leu Arg Gln Lys Ser
1890              1895              1900

Ser Thr Ser Leu Ser Asn Gly Gly Ala Ile Gln Asn Gln Glu Ser Gly
1905              1910              1915              1920

Ile Lys Glu Ser Val Ser Trp Gly Thr Gln Arg Thr Gln Asp Ala Pro
    1925              1930              1935

His Glu Ala Arg Pro Pro Leu Glu Arg Gly His Ser Thr Glu Ile Pro
1940              1945              1950

Val Gly Arg Ser Gly Ala Leu Ala Val Asp Val Gln Met Gln Ser Ile
1955              1960              1965

Thr Arg Arg Gly Pro Asp Gly Glu Pro Gln Pro Gly Leu Glu Ser Gln
1970              1975              1980

Gly Arg Ala Ala Ser Met Pro Arg Leu Ala Ala Glu Thr Gln Pro Val
1985              1990              1995              2000

Thr Asp Ala Ser Pro Met Lys Arg Ser Ile Ser Thr Leu Ala Gln Arg
    2005              2010              2015

Pro Arg Gly Thr His Leu Cys Ser Thr Thr Pro Asp Arg Pro Pro Pro
2020              2025              2030

-continued

```
Ser Gln Ala Ser Ser His His His His Arg Cys His Arg Arg Arg
    2050                2055                2060

Asp Arg Lys Gln Arg Ser Leu Glu Lys Gly Pro Ser Leu Ser Ala Asp
2065                2070                2075                2080

Met Asp Gly Ala Pro Ser Ser Ala Val Gly Pro Gly Leu Pro Pro Gly
            2085                2090                2095

Glu Gly Pro Thr Gly Cys Arg Arg Glu Arg Arg Gln Glu Arg
        2100                2105                2110

Gly Arg Ser Gln Glu Arg Arg Gln Pro Ser Ser Ser Ser Glu Lys
        2115                2120                2125

Gln Arg Phe Tyr Ser Cys Asp Arg Phe Gly Arg Glu Pro Pro Lys
    2130                2135                2140

Pro Lys Pro Ser Leu Ser Ser His Pro Thr Ser Pro Thr Ala Gly Gln
2145                2150                2155                2160

Glu Pro Gly Pro His Pro Gln Gly Ser Gly Val Asn Gly Ser Pro
            2165                2170                2175

Leu Leu Ser Thr Ser Gly Ala Ser Thr Pro Gly Arg Gly Gly Arg Arg
            2180                2185                2190

Gln Leu Pro Gln Thr Pro Leu Thr Pro Arg Pro Ser Ile Thr Tyr Lys
        2195                2200                2205

Thr Ala Asn Ser Ser Pro Ile His Phe Ala Gly Ala Gln Thr Ser Leu
    2210                2215                2220

Pro Ala Phe Ser Pro Gly Arg Leu Ser Arg Gly Leu Ser Glu His Asn
2225                2230                2235                2240

Ala Leu Leu Gln Arg Asp Pro Leu Ser Gln Pro Leu Ala Pro Gly Ser
            2245                2250                2255

Arg Ile Gly Ser Asp Pro Tyr Leu Gly Gln Arg Leu Asp Ser Glu Ala
            2260                2265                2270

Ser Val His Ala Leu Pro Glu Asp Thr Leu Thr Phe Glu Glu Ala Val
        2275                2280                2285

Ala Thr Asn Ser Gly Arg Ser Ser Arg Thr Ser Tyr Val Ser Ser Leu
    2290                2295                2300

Thr Ser Gln Ser His Pro Leu Arg Arg Val Pro Asn Gly Tyr His Cys
2305                2310                2315                2320

Thr Leu Gly Leu Ser Ser Gly Gly Arg Ala Arg His Ser Tyr His His
            2325                2330                2335

Pro Asp Gln Asp His Trp Cys
            2340

<210> SEQ ID NO 5
<211> LENGTH: 7364
<212> TYPE: DNA
<213> ORGANISM: Homo sapiens
<220> FEATURE:
<221> NAME/KEY: CDS
<222> LOCATION: 146..7162

<400> SEQUENCE: 5
gcggcggcgg ctgcggcggt ggggccgggc gaggtccgct gcggtcccgg cggctccgtg    60
gctgctccgc tctgagcgcc tggcgcgccc cgcgccctcc ctgccggggc cgctgggccg   120
gggatgcacg cggggcccgg gagcc atg gtc cgc ttc ggg gac gag ctg ggc   172
                           Met Val Arg Phe Gly Asp Glu Leu Gly
                             1               5 ggc cgc tat gga ggc ccc ggc ggc gga gag cgg gcc cgg ggc ggc ggg   220
Gly Arg Tyr Gly Gly Pro Gly Gly Gly Glu Arg Ala Arg Gly Gly Gly
```

```
                    -continued
          10                  15                  20                  25 gcc ggc ggg gcg ggg ggc ccg ggt ccc ggg ggg ctg cag ccc ggc cag    268
Ala Gly Gly Ala Gly Gly Pro Gly Pro Gly Gly Leu Gln Pro Gly Gln
                    30                  35                  40 cgg gtc ctc tac aag caa tcg atc gcg cag cgc gcg cgg acc atg gcg    316
Arg Val Leu Tyr Lys Gln Ser Ile Ala Gln Arg Ala Arg Thr Met Ala
                45                  50                  55 ctg tac aac ccc atc ccg gtc aag cag aac tgc ttc acc gtc aac cgc    364
Leu Tyr Asn Pro Ile Pro Val Lys Gln Asn Cys Phe Thr Val Asn Arg
            60                  65                  70 tcg ctc ttc gtc ttc agc gag gac aac gtc gtc cgc aaa tac gcg aag    412
Ser Leu Phe Val Phe Ser Glu Asp Asn Val Val Arg Lys Tyr Ala Lys
        75                  80                  85 cgc atc acc gag tgg cct cca ttc gag tat atg atc ctg gcc acc atc    460
Arg Ile Thr Glu Trp Pro Pro Phe Glu Tyr Met Ile Leu Ala Thr Ile
90                  95                  100                 105 atc gcc aac tgc atc gtg ctg gcc ctg gag cag cac ctc cct gat ggg    508
Ile Ala Asn Cys Ile Val Leu Ala Leu Glu Gln His Leu Pro Asp Gly
                    110                 115                 120 gac aaa acg ccc atg tcc gag cgg ctg gac gac acg gag ccc tat ttc    556
Asp Lys Thr Pro Met Ser Glu Arg Leu Asp Asp Thr Glu Pro Tyr Phe
                125                 130                 135 atc ggg atc ttt tgc ttc gag gca ggg atc aaa atc atc gct ctg ggc    604
Ile Gly Ile Phe Cys Phe Glu Ala Gly Ile Lys Ile Ile Ala Leu Gly
            140                 145                 150 ttt gtc ttc cac aag ggc tct tac ctg cgg aac ggc tgg aac gtc atg    652
Phe Val Phe His Lys Gly Ser Tyr Leu Arg Asn Gly Trp Asn Val Met
        155                 160                 165 gac ttc gtg gtc gtc ctc aca ggg atc ctt gcc acg gct gga act gac    700
Asp Phe Val Val Val Leu Thr Gly Ile Leu Ala Thr Ala Gly Thr Asp
170                 175                 180                 185 ttc gac ctg cga aca ctg agg gct gtg cgt gtg ctg agg ccc ctg aag    748
Phe Asp Leu Arg Thr Leu Arg Ala Val Arg Val Leu Arg Pro Leu Lys
                    190                 195                 200 ctg gtg tct ggg att cca agt ttg cag gtg gtg ctc aag tcc atc atg    796
Leu Val Ser Gly Ile Pro Ser Leu Gln Val Val Leu Lys Ser Ile Met
                205                 210                 215 aag gcc atg gtt cca ctc ctg cag att ggg ctg ctt ctc ttc ttt gcc    844
Lys Ala Met Val Pro Leu Leu Gln Ile Gly Leu Leu Leu Phe Phe Ala
            220                 225                 230 atc ctc atg ttt gcc atc att ggc ctg gag ttc tac atg ggc aag ttc    892
Ile Leu Met Phe Ala Ile Ile Gly Leu Glu Phe Tyr Met Gly Lys Phe
        235                 240                 245 cac aag gcc tgt ttc ccc aac agc aca gat gcg gag ccc gtg ggt gac    940
His Lys Ala Cys Phe Pro Asn Ser Thr Asp Ala Glu Pro Val Gly Asp
250                 255                 260                 265 ttc ccc tgt ggc aag gag gcc cca gcc cgg ctg tgc gag ggc gac act    988
Phe Pro Cys Gly Lys Glu Ala Pro Ala Arg Leu Cys Glu Gly Asp Thr
                    270                 275                 280 gag tgc cgg gag tac tgg cca gga ccc aac ttt ggc atc acc aac ttt    1036
Glu Cys Arg Glu Tyr Trp Pro Gly Pro Asn Phe Gly Ile Thr Asn Phe
                285                 290                 295 gac aat atc ctg ttt gcc atc ttg acg gtg ttc cag tgc atc acc atg    1084
Asp Asn Ile Leu Phe Ala Ile Leu Thr Val Phe Gln Cys Ile Thr Met
            300                 305                 310 gag ggc tgg act gac atc ctc tat aat aca aac gat gcg gcc ggc aac    1132
Glu Gly Trp Thr Asp Ile Leu Tyr Asn Thr Asn Asp Ala Ala Gly Asn
        315                 320                 325 acc tgg aac tgg ctc tac ttc atc cct ctc atc atc atc ggc tcc ttc    1180
```

```
                                                                          -continued Thr Trp Asn Trp Leu Tyr Phe Ile Pro Leu Ile Ile Ile Gly Ser Phe
330                 335                 340                 345 ttc atg ctc aac ctg gtg ctg ggc gtg ctc tcg ggg gag ttt gcc aag      1228
Phe Met Leu Asn Leu Val Leu Gly Val Leu Ser Gly Glu Phe Ala Lys
                350                 355                 360 gag cga gag agg gtg gag aac cgc cgc gcc ttc ctg aag ctg cgc cgg      1276
Glu Arg Glu Arg Val Glu Asn Arg Arg Ala Phe Leu Lys Leu Arg Arg
                365                 370                 375 cag cag cag atc gag cga gag ctc aac ggg tac ctg gag tgg atc ttc      1324
Gln Gln Gln Ile Glu Arg Glu Leu Asn Gly Tyr Leu Glu Trp Ile Phe
            380                 385                 390 aag gcg gag gaa gtc atg ctg gcc gag gag gac agg aat gca gag gag      1372
Lys Ala Glu Glu Val Met Leu Ala Glu Glu Asp Arg Asn Ala Glu Glu
            395                 400                 405 aag tcc cct ttg gac gtg ctg aag aga gcg gcc acc aag aag agc aga      1420
Lys Ser Pro Leu Asp Val Leu Lys Arg Ala Ala Thr Lys Lys Ser Arg
410                 415                 420                 425 aat gac ctg atc cac gca gag gag gga gag gac cgg ttt gca gat ctc      1468
Asn Asp Leu Ile His Ala Glu Glu Gly Glu Asp Arg Phe Ala Asp Leu
                430                 435                 440 tgt gct gtt gga tcc ccc ttc gcc cgc gcc agc ctc aag agc ggg aag      1516
Cys Ala Val Gly Ser Pro Phe Ala Arg Ala Ser Leu Lys Ser Gly Lys
                445                 450                 455 aca gag agc tcg tca tac ttc cgg agg aag gag aag atg ttc cgg ttt      1564
Thr Glu Ser Ser Ser Tyr Phe Arg Arg Lys Glu Lys Met Phe Arg Phe
                460                 465                 470 ttt atc cgg cgc atg gtg aag gct cag agc ttc tac tgg gtg gtg ctg      1612
Phe Ile Arg Arg Met Val Lys Ala Gln Ser Phe Tyr Trp Val Val Leu
475                 480                 485 tgc gtg gtg gcc ctg aac aca ctg tgt gtg gcc atg gtg cat tac aac      1660
Cys Val Val Ala Leu Asn Thr Leu Cys Val Ala Met Val His Tyr Asn
490                 495                 500                 505 cag ccg cgg cgg ctt acc acg acc ctg tat ttt gca gag ttt gtt ttc      1708
Gln Pro Arg Arg Leu Thr Thr Thr Leu Tyr Phe Ala Glu Phe Val Phe
                510                 515                 520 ctg ggt ctc ttc ctc aca gag atg tcc ctg aag atg tat ggc ctg ggg      1756
Leu Gly Leu Phe Leu Thr Glu Met Ser Leu Lys Met Tyr Gly Leu Gly
                525                 530                 535 ccc aga agc tac ttc cgg tcc tcc ttc aac tgc ttc gac ttt ggg gtc      1804
Pro Arg Ser Tyr Phe Arg Ser Ser Phe Asn Cys Phe Asp Phe Gly Val
                540                 545                 550 atc gtg ggg agc gtc ttt gaa gtg gtc tgg gcg gcc atc aag ccg gga      1852
Ile Val Gly Ser Val Phe Glu Val Val Trp Ala Ala Ile Lys Pro Gly
555                 560                 565 agc tcc ttt ggg atc agt gtg ctg cgg gcc ctc cgc ctg ctg agg atc      1900
Ser Ser Phe Gly Ile Ser Val Leu Arg Ala Leu Arg Leu Leu Arg Ile
570                 575                 580                 585 ttc aaa gtc acg aag tac tgg agc tcc ctg cgg aac ctg gtg gtg tcc      1948
Phe Lys Val Thr Lys Tyr Trp Ser Ser Leu Arg Asn Leu Val Val Ser
                590                 595                 600 ctg ctg aac tcc atg aag tcc atc atc agc ctg ctc ttg ctc ttc          1996
Leu Leu Asn Ser Met Lys Ser Ile Ile Ser Leu Leu Phe Leu Phe
                605                 610                 615 ctg ttc att gtg gtc ttc gcc ctg ctg ggg atg cag ctg ttt ggg gga      2044
Leu Phe Ile Val Val Phe Ala Leu Leu Gly Met Gln Leu Phe Gly Gly
                620                 625                 630 cag ttc aac ttc cag gat gag act ccc aca acc aac ttc gac acc ttc      2092
Gln Phe Asn Phe Gln Asp Glu Thr Pro Thr Thr Asn Phe Asp Thr Phe
                635                 640                 645
```

-continued

| | |
|---|---|
| cct gcc gcc atc ctc act gtc ttc cag atc ctg acg gga gag gac tgg<br>Pro Ala Ala Ile Leu Thr Val Phe Gln Ile Leu Thr Gly Glu Asp Trp<br>650                655                660                665 | 2140 |
| aat gca gtg atg tat cac ggg atc gaa tcg caa ggc ggc gtc agc aaa<br>Asn Ala Val Met Tyr His Gly Ile Glu Ser Gln Gly Gly Val Ser Lys<br>                670                675                680 | 2188 |
| ggc atg ttc tcg tcc ttt tac ttc att gtc ctg aca ctg ttc gga aac<br>Gly Met Phe Ser Ser Phe Tyr Phe Ile Val Leu Thr Leu Phe Gly Asn<br>685                690                695 | 2236 |
| tac act ctg ctg aat gtc ttt ctg gcc atc gct gtg gac aac ctg gcc<br>Tyr Thr Leu Leu Asn Val Phe Leu Ala Ile Ala Val Asp Asn Leu Ala<br>                700                705                710 | 2284 |
| aac gcc caa gag ctg acc aag gat gaa gag gag atg gaa gaa gca gcc<br>Asn Ala Gln Glu Leu Thr Lys Asp Glu Glu Glu Met Glu Glu Ala Ala<br>715                720                725 | 2332 |
| aat cag aag ctt gct ctg caa aag gcc aaa gaa gtg gct gaa gtc agc<br>Asn Gln Lys Leu Ala Leu Gln Lys Ala Lys Glu Val Ala Glu Val Ser<br>730                735                740                745 | 2380 |
| ccc atg tct gcc gcg aac atc tcc atc gcc gcc agg cag cag aac tcg<br>Pro Met Ser Ala Ala Asn Ile Ser Ile Ala Ala Arg Gln Gln Asn Ser<br>                750                755                760 | 2428 |
| gcc aag gcg cgc tcg gtg tgg gag cag cgg gcc agc cag cta cgg ctg<br>Ala Lys Ala Arg Ser Val Trp Glu Gln Arg Ala Ser Gln Leu Arg Leu<br>765                770                775 | 2476 |
| cag aac ctg cgg gcc agc tgc gag gcg ctg tac agc gag atg gac ccc<br>Gln Asn Leu Arg Ala Ser Cys Glu Ala Leu Tyr Ser Glu Met Asp Pro<br>780                785                790 | 2524 |
| gag gag cgg ctg cgc ttc gcc act acg cgc cac ctg cgg ccc gac atg<br>Glu Glu Arg Leu Arg Phe Ala Thr Thr Arg His Leu Arg Pro Asp Met<br>795                800                805 | 2572 |
| aag acg cac ctg gac cgg ccg ctg gtg gtg gag ctg ggc cgc gac ggc<br>Lys Thr His Leu Asp Arg Pro Leu Val Val Glu Leu Gly Arg Asp Gly<br>810                815                820                825 | 2620 |
| gcg cgg ggg ccc gtg gga ggc aaa gcc cga cct gag gct gcg gag gcc<br>Ala Arg Gly Pro Val Gly Gly Lys Ala Arg Pro Glu Ala Ala Glu Ala<br>                830                835                840 | 2668 |
| ccc gag ggc gtc gac cct ccg cgc agg cac cac cgg cac cgc gac aag<br>Pro Glu Gly Val Asp Pro Pro Arg Arg His His Arg His Arg Asp Lys<br>845                850                855 | 2716 |
| gac aag acc ccc gcg gcg ggg gac cag gac cga gca gag gcc ccg aag<br>Asp Lys Thr Pro Ala Ala Gly Asp Gln Asp Arg Ala Glu Ala Pro Lys<br>860                865                870 | 2764 |
| gcg gag agc ggg gag ccc ggt gcc cgg gag gag cgg ccg cgg ccg cac<br>Ala Glu Ser Gly Glu Pro Gly Ala Arg Glu Glu Arg Pro Arg Pro His<br>875                880                885 | 2812 |
| cgc agc cac agc aag gag gcc gcg ggg ccc ccg gag gcg cgg agc gag<br>Arg Ser His Ser Lys Glu Ala Ala Gly Pro Pro Glu Ala Arg Ser Glu<br>890                895                900                905 | 2860 |
| cgc ggc cga ggc cca ggc ccc gag ggc ggc cgg cgg cac cac cgg cgc<br>Arg Gly Arg Gly Pro Gly Pro Glu Gly Gly Arg Arg His His Arg Arg<br>                910                915                920 | 2908 |
| ggc tcc ccg gag gag gcg gcc gag cgg gag ccc cga cgc cac cgc gcg<br>Gly Ser Pro Glu Glu Ala Ala Glu Arg Glu Pro Arg Arg His Arg Ala<br>925                930                935 | 2956 |
| cac cgg cac cag gat ccg agc aag gag tgc gcc ggc gcc aag ggc gag<br>His Arg His Gln Asp Pro Ser Lys Glu Cys Ala Gly Ala Lys Gly Glu<br>                940                945                950 | 3004 |
| cgg cgc gcg cgg cac cgc ggc ggc ccc gac gcg ggg ccc cgg gag gcg<br>Arg Arg Ala Arg His Arg Gly Gly Pro Arg Ala Gly Pro Arg Glu Ala<br>955                960                965 | 3052 |

-continued

| | |
|---|---|
| gag agc ggg gag gag ccg gcg cgg cgg cac cgg gcc cgg cac aag gcg<br>Glu Ser Gly Glu Glu Pro Ala Arg Arg His Arg Ala Arg His Lys Ala<br>970                        975                      980                      985 | 3100 |
| cag cct gct cac gag gct gtg gag aag gag acc acg gag aag gag gcc<br>Gln Pro Ala His Glu Ala Val Glu Lys Glu Thr Thr Glu Lys Glu Ala<br>                        990                      995                     1000 | 3148 |
| acg gag aag gag gct gag ata gtg gaa gcc gac aag gaa aag gag ctc<br>Thr Glu Lys Glu Ala Glu Ile Val Glu Ala Asp Lys Glu Lys Glu Leu<br>          1005                     1010                     1015 | 3196 |
| cgg aac cac cag ccc cgg gag cca cac tgt gac ctg gag acc agt ggg<br>Arg Asn His Gln Pro Arg Glu Pro His Cys Asp Leu Glu Thr Ser Gly<br>          1020                     1025                     1030 | 3244 |
| act gtg act gtg ggt ccc atg cac aca ctg ccc agc acc tgt ctc cag<br>Thr Val Thr Val Gly Pro Met His Thr Leu Pro Ser Thr Cys Leu Gln<br>          1035                     1040                     1045 | 3292 |
| aag gtg gag gaa cag cca gag gat gca gac aat cag cgg aac gtc act<br>Lys Val Glu Glu Gln Pro Glu Asp Ala Asp Asn Gln Arg Asn Val Thr<br>1050                      1055                    1060                    1065 | 3340 |
| cgc atg ggc agt cag ccc cca gac ccg aac act att gta cat atc cca<br>Arg Met Gly Ser Gln Pro Pro Asp Pro Asn Thr Ile Val His Ile Pro<br>          1070                     1075                     1080 | 3388 |
| gtg atg ctg acg ggc cct ctt ggg gaa gcc acg gtc gtt ccc agt ggt<br>Val Met Leu Thr Gly Pro Leu Gly Glu Ala Thr Val Val Pro Ser Gly<br>          1085                     1090                     1095 | 3436 |
| aac gtg gac ctg gaa agc caa gca gag ggg aag aag gag gtg gaa gcg<br>Asn Val Asp Leu Glu Ser Gln Ala Glu Gly Lys Lys Glu Val Glu Ala<br>1100                      1105                    1110 | 3484 |
| gat gac gtg atg agg agc ggc ccc cgg cct atc gtc cca tac agc tcc<br>Asp Asp Val Met Arg Ser Gly Pro Arg Pro Ile Val Pro Tyr Ser Ser<br>    1115                     1120                    1125 | 3532 |
| atg ttc tgt tta agc ccc acc aac ctg ctc cgc cgc ttc tgc cac tac<br>Met Phe Cys Leu Ser Pro Thr Asn Leu Leu Arg Arg Phe Cys His Tyr<br>1130                      1135                    1140                    1145 | 3580 |
| atc gtg acc atg agg tac ttc gag gtg gtc att ctc gtg gtc atc gcc<br>Ile Val Thr Met Arg Tyr Phe Glu Val Val Ile Leu Val Val Ile Ala<br>          1150                     1155                     1160 | 3628 |
| ttg agc agc atc gcc ctg gct gct gag gac cca gtg cgc aca gac tcg<br>Leu Ser Ser Ile Ala Leu Ala Ala Glu Asp Pro Val Arg Thr Asp Ser<br>          1165                     1170                     1175 | 3676 |
| ccc agg aac aac gct ctg aaa tac ctg gat tac att ttc act ggt gtc<br>Pro Arg Asn Asn Ala Leu Lys Tyr Leu Asp Tyr Ile Phe Thr Gly Val<br>1180                      1185                    1190 | 3724 |
| ttt acc ttt gag atg gtg ata aag atg atc gac ttg gga ctg ctg ctt<br>Phe Thr Phe Glu Met Val Ile Lys Met Ile Asp Leu Gly Leu Leu Leu<br>          1195                     1200                     1205 | 3772 |
| cac cct gga gcc tat ttc cgg gac ttg tgg aac att ctg gac ttc att<br>His Pro Gly Ala Tyr Phe Arg Asp Leu Trp Asn Ile Leu Asp Phe Ile<br>1210                      1215                    1220                    1225 | 3820 |
| gtg gtc agt ggc gcc ctg gtg gcg ttt gct ttc tca gga tcc aaa ggg<br>Val Val Ser Gly Ala Leu Val Ala Phe Ala Phe Ser Gly Ser Lys Gly<br>          1230                     1235                     1240 | 3868 |
| aaa gac atc aat acc atc aag tct ctg aga gtc ctt cgt gtc ctg cgg<br>Lys Asp Ile Asn Thr Ile Lys Ser Leu Arg Val Leu Arg Val Leu Arg<br>          1245                     1250                     1255 | 3916 |
| ccc ctc aag acc atc aaa cgg ctg ccc aag ctc aag gct gtg ttt gac<br>Pro Leu Lys Thr Ile Lys Arg Leu Pro Lys Leu Lys Ala Val Phe Asp<br>          1260                     1265                     1270 | 3964 |
| tgt gtg gtg aac tcc ctg aag aat gtc ctc aac atc ttg att gtc tac<br>Cys Val Val Asn Ser Leu Lys Asn Val Leu Asn Ile Leu Ile Val Tyr | 4012 |

-continued

```
         1275                1280                1285
atg ctc ttc atg ttc ata ttt gcc gtc att gcg gtg cag ctc ttc aaa    4060
Met Leu Phe Met Phe Ile Phe Ala Val Ile Ala Val Gln Leu Phe Lys
1290                1295                1300                1305 ggg aag ttt ttc tac tgc aca gat gaa tcc aag gag ctg gag agg gac    4108
Gly Lys Phe Phe Tyr Cys Thr Asp Glu Ser Lys Glu Leu Glu Arg Asp
            1310                1315                1320 tgc agg ggt cag tat ttg gat tat gag aag gag gaa gtg gaa gct cag    4156
Cys Arg Gly Gln Tyr Leu Asp Tyr Glu Lys Glu Glu Val Glu Ala Gln
        1325                1330                1335 ccc agg cag tgg aag aaa tac gac ttt cac tac gac aat gtg ctc tgg    4204
Pro Arg Gln Trp Lys Lys Tyr Asp Phe His Tyr Asp Asn Val Leu Trp
    1340                1345                1350 gct ctg ctg acg ctg ttc aca gtg tcc acg gga gaa ggc tgg ccc atg    4252
Ala Leu Leu Thr Leu Phe Thr Val Ser Thr Gly Glu Gly Trp Pro Met
1355                1360                1365 gtg ctg aaa cac tcc gtg gat gcc acc tat gag gag cag ggt cca agc    4300
Val Leu Lys His Ser Val Asp Ala Thr Tyr Glu Glu Gln Gly Pro Ser
1370                1375                1380                1385 cct ggg tac cgc atg gag ctg tcc atc ttc tac gtg gtc tac ttt gtg    4348
Pro Gly Tyr Arg Met Glu Leu Ser Ile Phe Tyr Val Val Tyr Phe Val
            1390                1395                1400 gtc ttt ccc ttc ttc ttc gtc aac atc ttt gtg gct ttg atc atc atc    4396
Val Phe Pro Phe Phe Phe Val Asn Ile Phe Val Ala Leu Ile Ile Ile
        1405                1410                1415 acc ttc cag gag cag ggg gac aag gtg atg tct gaa tgc agc ctg gag    4444
Thr Phe Gln Glu Gln Gly Asp Lys Val Met Ser Glu Cys Ser Leu Glu
    1420                1425                1430 aag aac gag agg gct tgc att gac ttc gcc atc agc gcc aaa ccc ctg    4492
Lys Asn Glu Arg Ala Cys Ile Asp Phe Ala Ile Ser Ala Lys Pro Leu
1435                1440                1445 aca cgg tac atg ccc caa aac cgg cag tcg ttc cag tat aag acg tgg    4540
Thr Arg Tyr Met Pro Gln Asn Arg Gln Ser Phe Gln Tyr Lys Thr Trp
1450                1455                1460                1465 aca ttt gtg gtc tcc ccg ccc ttt gaa tac ttc atc atg gcc atg ata    4588
Thr Phe Val Val Ser Pro Pro Phe Glu Tyr Phe Ile Met Ala Met Ile
            1470                1475                1480 gcc ctc aac act gtg gtg ctg atg atg aag ttc tat gat gca ccc tat    4636
Ala Leu Asn Thr Val Val Leu Met Met Lys Phe Tyr Asp Ala Pro Tyr
        1485                1490                1495 gag tac gag ctg atg ctg aaa tgc ctg aac atc gtg ttc aca tcc atg    4684
Glu Tyr Glu Leu Met Leu Lys Cys Leu Asn Ile Val Phe Thr Ser Met
    1500                1505                1510 ttc tcc atg gaa tgc gtg ctg aag atc atc gcc ttt ggg gtg ctg aac    4732
Phe Ser Met Glu Cys Val Leu Lys Ile Ile Ala Phe Gly Val Leu Asn
1515                1520                1525 tat ttc aga gat gcc tgg aat gtc ttt gac ttt gtc act gtg ttg gga    4780
Tyr Phe Arg Asp Ala Trp Asn Val Phe Asp Phe Val Thr Val Leu Gly
1530                1535                1540                1545 agt att act gat att tta gta aca gag att gcg gaa acg aac aat ttc    4828
Ser Ile Thr Asp Ile Leu Val Thr Glu Ile Ala Glu Thr Asn Asn Phe
            1550                1555                1560 atc aac ctc agc ttc ctc cgc ctc ttt cga gct gcg cgg ctg atc aag    4876
Ile Asn Leu Ser Phe Leu Arg Leu Phe Arg Ala Ala Arg Leu Ile Lys
        1565                1570                1575 ctg ctc cgc cag ggc tac acc atc cgc atc ctg ctg tgg acc ttt gtc    4924
Leu Leu Arg Gln Gly Tyr Thr Ile Arg Ile Leu Leu Trp Thr Phe Val
    1580                1585                1590 cag tcc ttc aag gcc ctg ccc tac gtg tgt ctg ctc att gcc atg ctg    4972
```

```
                                                                         -continued Gln Ser Phe Lys Ala Leu Pro Tyr Val Cys Leu Leu Ile Ala Met Leu
 1595                1600                1605 ttc ttc atc tac gcc atc atc ggc atg cag gtg ttt ggg aat att gcc      5020
Phe Phe Ile Tyr Ala Ile Ile Gly Met Gln Val Phe Gly Asn Ile Ala
1610                1615                1620                1625 ctg gat gat gac acc agc atc aac cgc cac aac aac ttc cgg acg ttt      5068
Leu Asp Asp Asp Thr Ser Ile Asn Arg His Asn Asn Phe Arg Thr Phe
            1630                1635                1640 ttg caa gcc ctg atg ctg ctg ttc agg agc gcc acg ggg gag gcc tgg      5116
Leu Gln Ala Leu Met Leu Leu Phe Arg Ser Ala Thr Gly Glu Ala Trp
        1645                1650                1655 cac gag atc atg ctg tcc tgc ctg agc aac cag gcc tgt gat gag cag      5164
His Glu Ile Met Leu Ser Cys Leu Ser Asn Gln Ala Cys Asp Glu Gln
    1660                1665                1670 gcc aat gcc acc gag tgt gga agt gac ttt gcc tac ttc tac ttc gtc      5212
Ala Asn Ala Thr Glu Cys Gly Ser Asp Phe Ala Tyr Phe Tyr Phe Val
1675                1680                1685 tcc ttc atc ttc ctg tgc tcc ttt ctg atg ttg aac ctc ttt gtg gct      5260
Ser Phe Ile Phe Leu Cys Ser Phe Leu Met Leu Asn Leu Phe Val Ala
1690                1695                1700                1705 gtg atc atg gac aat ttt gag tac ctc acg cgg gac tct tcc atc cta      5308
Val Ile Met Asp Asn Phe Glu Tyr Leu Thr Arg Asp Ser Ser Ile Leu
            1710                1715                1720 ggt cct cac cac ttg gat gag ttc atc cgg gtc tgg gct gaa tac gac      5356
Gly Pro His His Leu Asp Glu Phe Ile Arg Val Trp Ala Glu Tyr Asp
        1725                1730                1735 ccg gct gcg tgt ggg cgc atc agt tac aat gac atg ttt gag atg ctg      5404
Pro Ala Ala Cys Gly Arg Ile Ser Tyr Asn Asp Met Phe Glu Met Leu
    1740                1745                1750 aaa cac atg tcc ccg cct ctg ggg ctg ggg aag aaa tgc cct gct cga      5452
Lys His Met Ser Pro Pro Leu Gly Leu Gly Lys Lys Cys Pro Ala Arg
1755                1760                1765 gtt gct tac aag cgc ctg gtt cgc atg aac atg ccc atc tcc aac gag      5500
Val Ala Tyr Lys Arg Leu Val Arg Met Asn Met Pro Ile Ser Asn Glu
1770                1775                1780                1785 gac atg act gtt cac ttc acg tcc acg ctg atg gcc ctc atc cgg acg      5548
Asp Met Thr Val His Phe Thr Ser Thr Leu Met Ala Leu Ile Arg Thr
            1790                1795                1800 gca ctg gag atc aag ctg gcc cca gct ggg aca aag cag cat cag tgt      5596
Ala Leu Glu Ile Lys Leu Ala Pro Ala Gly Thr Lys Gln His Gln Cys
        1805                1810                1815 gac gcg gag ttg agg aag gag att tcc gtt gtg tgg gcc aat ctg ccc      5644
Asp Ala Glu Leu Arg Lys Glu Ile Ser Val Val Trp Ala Asn Leu Pro
    1820                1825                1830 cag aag act ttg gac ttg ctg gta cca ccc cat aag cct gat gag atg      5692
Gln Lys Thr Leu Asp Leu Leu Val Pro Pro His Lys Pro Asp Glu Met
1835                1840                1845 aca gtg ggg aag gtt tat gca gct ctg atg ata ttt gac ttc tac aag      5740
Thr Val Gly Lys Val Tyr Ala Ala Leu Met Ile Phe Asp Phe Tyr Lys
1850                1855                1860                1865 cag aac aaa acc acc aga gac cag atg cag cag gct cct gga ggc ctc      5788
Gln Asn Lys Thr Thr Arg Asp Gln Met Gln Gln Ala Pro Gly Gly Leu
            1870                1875                1880 tcc cag atg ggt cct gtg tcc ctg ttc cac cct ctg aag gcc acc ctg      5836
Ser Gln Met Gly Pro Val Ser Leu Phe His Pro Leu Lys Ala Thr Leu
        1885                1890                1895 gag cag aca cag ccg gct gtg ctc cga gga gcc cgg gtt ttc ctt cga      5884
Glu Gln Thr Gln Pro Ala Val Leu Arg Gly Ala Arg Val Phe Leu Arg
    1900                1905                1910
```

```
cag aag agt tcc acc tcc ctc agc aat ggc ggg gcc ata caa aac caa    5932
Gln Lys Ser Ser Thr Ser Leu Ser Asn Gly Gly Ala Ile Gln Asn Gln
    1915                1920                1925 gag agt ggc atc aaa gag tct gtc tcc tgg ggc act caa agg acc cag    5980
Glu Ser Gly Ile Lys Glu Ser Val Ser Trp Gly Thr Gln Arg Thr Gln
1930                1935                1940                1945 gat gca ccc cat gag gcc agg cca ccc ctg gag cgt ggc cac tcc aca    6028
Asp Ala Pro His Glu Ala Arg Pro Pro Leu Glu Arg Gly His Ser Thr
                1950                1955                1960 gag atc cct gtg ggg cgg tca gga gca ctg gct gtg gac gtt cag atg    6076
Glu Ile Pro Val Gly Arg Ser Gly Ala Leu Ala Val Asp Val Gln Met
            1965                1970                1975 cag agc ata acc cgg agg ggc cct gat ggg gag ccc cag cct ggg ctg    6124
Gln Ser Ile Thr Arg Arg Gly Pro Asp Gly Glu Pro Gln Pro Gly Leu
        1980                1985                1990 gag agc cag ggt cga gcg gcc tcc atg ccc cgc ctt gcg gcc gag act    6172
Glu Ser Gln Gly Arg Ala Ala Ser Met Pro Arg Leu Ala Ala Glu Thr
    1995                2000                2005 cag ccc gtc aca gat gcc agc ccc atg aag cgc tcc atc tcc acg ctg    6220
Gln Pro Val Thr Asp Ala Ser Pro Met Lys Arg Ser Ile Ser Thr Leu
2010                2015                2020                2025 gcc cag cgg ccc cgt ggg act cat ctt tgc agc acc acc ccg gac cgc    6268
Ala Gln Arg Pro Arg Gly Thr His Leu Cys Ser Thr Thr Pro Asp Arg
                2030                2035                2040 cca ccc cct agc cag gcg tcg tcg cac cac cac cac cac cgc tgc cac    6316
Pro Pro Pro Ser Gln Ala Ser Ser His His His His His Arg Cys His
            2045                2050                2055 cgc cgc agg gac agg aag cag agg tcc ctg gag aag ggg ccc agc ctg    6364
Arg Arg Arg Asp Arg Lys Gln Arg Ser Leu Glu Lys Gly Pro Ser Leu
        2060                2065                2070 tct gcc gat atg gat ggc gca cca agc agt gct gtg ggg ccg ggg ctg    6412
Ser Ala Asp Met Asp Gly Ala Pro Ser Ser Ala Val Gly Pro Gly Leu
    2075                2080                2085 ccc ccg gga gag ggg cct aca ggc tgc cgg cgg gaa cga gag cgc cgg    6460
Pro Pro Gly Glu Gly Pro Thr Gly Cys Arg Arg Glu Arg Glu Arg Arg
2090                2095                2100                2105 cag gag cgg ggc cgg tcc cag gag cgg agg cag ccc tca tcc tcc tcc    6508
Gln Glu Arg Gly Arg Ser Gln Glu Arg Arg Gln Pro Ser Ser Ser Ser
                2110                2115                2120 tcg gag aag cag cgc ttc tac tcc tgc gac cgc ttt ggg ggc cgt gag    6556
Ser Glu Lys Gln Arg Phe Tyr Ser Cys Asp Arg Phe Gly Gly Arg Glu
            2125                2130                2135 ccc ccg aag ccc aag ccc tcc ctc agc agc cac cca acg tcg cca aca    6604
Pro Pro Lys Pro Lys Pro Ser Leu Ser Ser His Pro Thr Ser Pro Thr
        2140                2145                2150 gct ggc cag gag ccg gga ccc cac cca cag ggc agt ggt tcc gtg aat    6652
Ala Gly Gln Glu Pro Gly Pro His Pro Gln Gly Ser Gly Ser Val Asn
    2155                2160                2165 ggg agc ccc ttg ctg tca aca tct ggt gct agc acc ccc ggc cgc ggt    6700
Gly Ser Pro Leu Leu Ser Thr Ser Gly Ala Ser Thr Pro Gly Arg Gly
2170                2175                2180                2185 ggg cgg agg cag ctc ccc cag acg ccc ctg act ccc cgc ccc agc atc    6748
Gly Arg Arg Gln Leu Pro Gln Thr Pro Leu Thr Pro Arg Pro Ser Ile
                2190                2195                2200 acc tac aag acg gcc aac tcc tca ccc atc cac ttc gcc ggg gct cag    6796
Thr Tyr Lys Thr Ala Asn Ser Ser Pro Ile His Phe Ala Gly Ala Gln
            2205                2210                2215 acc agc ctc cct gcc ttc tcc cca ggc cgg ctc agc cgt ggg ctt tcc    6844
Thr Ser Leu Pro Ala Phe Ser Pro Gly Arg Leu Ser Arg Gly Leu Ser
        2220                2225                2230
```

-continued

```
gaa cac aac gcc ctg ctg cag aga gac ccc ctc agc cag ccc ctg gcc     6892
Glu His Asn Ala Leu Leu Gln Arg Asp Pro Leu Ser Gln Pro Leu Ala
    2235                2240                2245 cct ggc tct cga att ggc tct gac cct tac ctg ggg cag cgt ctg gac     6940
Pro Gly Ser Arg Ile Gly Ser Asp Pro Tyr Leu Gly Gln Arg Leu Asp
2250                2255                2260                2265 agt gag gcc tct gtc cac gcc ctg cct gag gac acg ctc act ttc gag     6988
Ser Glu Ala Ser Val His Ala Leu Pro Glu Asp Thr Leu Thr Phe Glu
            2270                2275                2280 gag gct gtg gcc acc aac tcg ggc cgc tcc tcc agg act tcc tac gtg     7036
Glu Ala Val Ala Thr Asn Ser Gly Arg Ser Ser Arg Thr Ser Tyr Val
        2285                2290                2295 tcc tcc ctg acc tcc cag tct cac cct ctc cgc cgc gtg ccc aac ggt     7084
Ser Ser Leu Thr Ser Gln Ser His Pro Leu Arg Arg Val Pro Asn Gly
    2300                2305                2310 tac cac tgc acc ctg gga ctc agc tcg ggt ggc cga gca cgg cac agc     7132
Tyr His Cys Thr Leu Gly Leu Ser Ser Gly Gly Arg Ala Arg His Ser
    2315                2320                2325 tac cac cac cct gac caa gac cac tgg tgc tagctgcacc gtgaccgctc aga   7185
Tyr His His Pro Asp Gln Asp His Trp Cys
2330                2335 cgcctgcatg cagcaggcgt gtgttccagt ggatgagttt tatcatccac acggggcagt   7245
cggccctcgg gggaggcctt gcccaccttg gtgaggctcc tgtggccccct ccctcccct    7305 cctcccctct tttactctag acgacgaata aagccctgtt gcttgagtgt acgtaccgc    7364

<210> SEQ ID NO 6
<211> LENGTH: 2339
<212> TYPE: PRT
<213> ORGANISM: Homo sapiens

<400> SEQUENCE: 6

Met Val Arg Phe Gly Asp Glu Leu Gly Gly Arg Tyr Gly Gly Pro Gly
 1               5                  10                  15

Gly Gly Glu Arg Ala Arg Gly Gly Ala Gly Gly Ala Gly Gly Pro
            20                  25                  30

Gly Pro Gly Gly Leu Gln Pro Gly Gln Arg Val Leu Tyr Lys Gln Ser
        35                  40                  45

Ile Ala Gln Arg Ala Arg Thr Met Ala Leu Tyr Asn Pro Ile Pro Val
    50                  55                  60

Lys Gln Asn Cys Phe Thr Val Asn Arg Ser Leu Phe Val Phe Ser Glu
65                  70                  75                  80

Asp Asn Val Val Arg Lys Tyr Ala Lys Arg Ile Thr Glu Trp Pro Pro
                85                  90                  95

Phe Glu Tyr Met Ile Leu Ala Thr Ile Ile Ala Asn Cys Ile Val Leu
            100                 105                 110

Ala Leu Glu Gln His Leu Pro Asp Gly Asp Lys Thr Pro Met Ser Glu
        115                 120                 125

Arg Leu Asp Asp Thr Glu Pro Tyr Phe Ile Gly Ile Phe Cys Phe Glu
    130                 135                 140

Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Leu Thr
                165                 170                 175

Gly Ile Leu Ala Thr Ala Gly Thr Asp Phe Asp Leu Arg Thr Leu Arg
            180                 185                 190
```

-continued

```
Ala Val Arg Val Leu Arg Pro Leu Lys Leu Val Ser Gly Ile Pro Ser
        195                 200                 205

Leu Gln Val Val Leu Lys Ser Ile Met Lys Ala Met Val Pro Leu Leu
    210                 215                 220

Gln Ile Gly Leu Leu Leu Phe Phe Ala Ile Leu Met Phe Ala Ile Ile
225                 230                 235                 240

Gly Leu Glu Phe Tyr Met Gly Lys Phe His Lys Ala Cys Phe Pro Asn
                245                 250                 255

Ser Thr Asp Ala Glu Pro Val Gly Asp Phe Pro Cys Gly Lys Glu Ala
            260                 265                 270

Pro Ala Arg Leu Cys Glu Gly Asp Thr Glu Cys Arg Glu Tyr Trp Pro
        275                 280                 285

Gly Pro Asn Phe Gly Ile Thr Asn Phe Asp Asn Ile Leu Phe Ala Ile
    290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                325                 330                 335

Ile Pro Leu Ile Ile Ile Gly Ser Phe Phe Met Leu Asn Leu Val Leu
            340                 345                 350

Gly Val Leu Ser Gly Glu Phe Ala Lys Glu Arg Glu Arg Val Glu Asn
        355                 360                 365

Arg Arg Ala Phe Leu Lys Leu Arg Arg Gln Gln Gln Ile Glu Arg Glu
370                 375                 380

Leu Asn Gly Tyr Leu Glu Trp Ile Phe Lys Ala Glu Glu Val Met Leu
385                 390                 395                 400

Ala Glu Glu Asp Arg Asn Ala Glu Glu Lys Ser Pro Leu Asp Val Leu
                405                 410                 415

Lys Arg Ala Ala Thr Lys Lys Ser Arg Asn Asp Leu Ile His Ala Glu
            420                 425                 430

Glu Gly Glu Asp Arg Phe Ala Asp Leu Cys Ala Val Gly Ser Pro Phe
        435                 440                 445

Ala Arg Ala Ser Leu Lys Ser Gly Lys Thr Glu Ser Ser Ser Tyr Phe
    450                 455                 460

Arg Arg Lys Glu Lys Met Phe Arg Phe Phe Ile Arg Arg Met Val Lys
465                 470                 475                 480

Ala Gln Ser Phe Tyr Trp Val Val Leu Cys Val Val Ala Leu Asn Thr
                485                 490                 495

Leu Cys Val Ala Met Val His Tyr Asn Gln Pro Arg Arg Leu Thr Thr
            500                 505                 510

Thr Leu Tyr Phe Ala Glu Phe Val Phe Leu Gly Leu Phe Leu Thr Glu
        515                 520                 525

Met Ser Leu Lys Met Tyr Gly Leu Gly Pro Arg Ser Tyr Phe Arg Ser
    530                 535                 540

Ser Phe Asn Cys Phe Asp Phe Gly Val Ile Val Gly Ser Val Phe Glu
545                 550                 555                 560

Val Val Trp Ala Ala Ile Lys Pro Gly Ser Ser Phe Gly Ile Ser Val
                565                 570                 575

Leu Arg Ala Leu Arg Leu Leu Arg Ile Phe Lys Val Thr Lys Tyr Trp
            580                 585                 590

Ser Ser Leu Arg Asn Leu Val Val Ser Leu Leu Asn Ser Met Lys Ser
        595                 600                 605

Ile Ile Ser Leu Leu Phe Leu Leu Phe Leu Phe Ile Val Val Phe Ala
```

-continued

```
        610                 615                 620
Leu Leu Gly Met Gln Leu Phe Gly Gly Gln Phe Asn Phe Gln Asp Glu
625                 630                 635                 640
Thr Pro Thr Thr Asn Phe Asp Thr Phe Pro Ala Ala Ile Leu Thr Val
                    645                 650                 655
Phe Gln Ile Leu Thr Gly Glu Asp Trp Asn Ala Val Met Tyr His Gly
                    660                 665                 670
Ile Glu Ser Gln Gly Gly Val Ser Lys Gly Met Phe Ser Ser Phe Tyr
                    675                 680                 685
Phe Ile Val Leu Thr Leu Phe Gly Asn Tyr Thr Leu Leu Asn Val Phe
                    690                 695                 700
Leu Ala Ile Ala Val Asp Asn Leu Ala Asn Ala Gln Glu Leu Thr Lys
705                 710                 715                 720
Asp Glu Glu Glu Met Glu Glu Ala Ala Asn Gln Lys Leu Ala Leu Gln
                    725                 730                 735
Lys Ala Lys Glu Val Ala Glu Val Ser Pro Met Ser Ala Ala Asn Ile
                    740                 745                 750
Ser Ile Ala Ala Arg Gln Gln Asn Ser Ala Lys Ala Arg Ser Val Trp
                    755                 760                 765
Glu Gln Arg Ala Ser Gln Leu Arg Leu Gln Asn Leu Arg Ala Ser Cys
770                 775                 780
Glu Ala Leu Tyr Ser Glu Met Asp Pro Glu Glu Arg Leu Arg Phe Ala
785                 790                 795                 800
Thr Thr Arg His Leu Arg Pro Asp Met Lys Thr His Leu Asp Arg Pro
                    805                 810                 815
Leu Val Val Glu Leu Gly Arg Asp Gly Ala Arg Gly Pro Val Gly Gly
                    820                 825                 830
Lys Ala Arg Pro Glu Ala Ala Glu Ala Pro Glu Gly Val Asp Pro Pro
                    835                 840                 845
Arg Arg His His Arg His Arg Asp Lys Asp Lys Thr Pro Ala Ala Gly
                    850                 855                 860
Asp Gln Asp Arg Ala Glu Ala Pro Lys Ala Glu Ser Gly Glu Pro Gly
865                 870                 875                 880
Ala Arg Glu Glu Arg Pro Arg Pro His Arg Ser His Ser Lys Glu Ala
                    885                 890                 895
Ala Gly Pro Pro Glu Ala Arg Ser Glu Arg Gly Arg Gly Pro Gly Pro
                    900                 905                 910
Glu Gly Gly Arg Arg His His Arg Arg Gly Ser Pro Glu Glu Ala Ala
                    915                 920                 925
Glu Arg Glu Pro Arg Arg His Arg Ala His Arg His Gln Asp Pro Ser
                    930                 935                 940
Lys Glu Cys Ala Gly Ala Lys Gly Glu Arg Arg Ala Arg His Arg Gly
945                 950                 955                 960
Gly Pro Arg Ala Gly Pro Arg Glu Ala Glu Ser Gly Glu Glu Pro Ala
                    965                 970                 975
Arg Arg His Arg Ala Arg His Lys Ala Gln Pro Ala His Glu Ala Val
                    980                 985                 990
Glu Lys Glu Thr Thr Glu Lys Glu Ala Thr Glu Lys Glu Ala Glu Ile
                    995                 1000                1005
Val Glu Ala Asp Lys Glu Lys Glu Leu Arg Asn His Gln Pro Arg Glu
                    1010                1015                1020
Pro His Cys Asp Leu Glu Thr Ser Gly Thr Val Thr Val Gly Pro Met
1025                1030                1035                1040
```

-continued

His Thr Leu Pro Ser Thr Cys Leu Gln Lys Val Glu Glu Gln Pro Glu
            1045                1050                1055

Asp Ala Asp Asn Gln Arg Asn Val Thr Arg Met Gly Ser Gln Pro Pro
            1060                1065                1070

Asp Pro Asn Thr Ile Val His Ile Pro Val Met Leu Thr Gly Pro Leu
            1075                1080                1085

Gly Glu Ala Thr Val Val Pro Ser Gly Asn Val Asp Leu Glu Ser Gln
            1090                1095                1100

Ala Glu Gly Lys Lys Glu Val Glu Ala Asp Asp Val Met Arg Ser Gly
1105                1110                1115                1120

Pro Arg Pro Ile Val Pro Tyr Ser Ser Met Phe Cys Leu Ser Pro Thr
            1125                1130                1135

Asn Leu Leu Arg Arg Phe Cys His Tyr Ile Val Thr Met Arg Tyr Phe
            1140                1145                1150

Glu Val Val Ile Leu Val Val Ile Ala Leu Ser Ser Ile Ala Leu Ala
            1155                1160                1165

Ala Glu Asp Pro Val Arg Thr Asp Ser Pro Arg Asn Asn Ala Leu Lys
            1170                1175                1180

Tyr Leu Asp Tyr Ile Phe Thr Gly Val Phe Thr Phe Glu Met Val Ile
1185                1190                1195                1200

Lys Met Ile Asp Leu Gly Leu Leu Leu His Pro Gly Ala Tyr Phe Arg
            1205                1210                1215

Asp Leu Trp Asn Ile Leu Asp Phe Ile Val Val Ser Gly Ala Leu Val
            1220                1225                1230

Ala Phe Ala Phe Ser Gly Ser Lys Gly Lys Asp Ile Asn Thr Ile Lys
            1235                1240                1245

Ser Leu Arg Val Leu Arg Val Leu Arg Pro Leu Lys Thr Ile Lys Arg
            1250                1255                1260

Leu Pro Lys Leu Lys Ala Val Phe Asp Cys Val Val Asn Ser Leu Lys
1265                1270                1275                1280

Asn Val Leu Asn Ile Leu Ile Val Tyr Met Leu Phe Met Phe Ile Phe
            1285                1290                1295

Ala Val Ile Ala Val Gln Leu Phe Lys Gly Lys Phe Phe Tyr Cys Thr
            1300                1305                1310

Asp Glu Ser Lys Glu Leu Glu Arg Asp Cys Arg Gly Gln Tyr Leu Asp
            1315                1320                1325

Tyr Glu Lys Glu Glu Val Glu Ala Gln Pro Arg Gln Trp Lys Lys Tyr
            1330                1335                1340

Asp Phe His Tyr Asp Asn Val Leu Trp Ala Leu Leu Thr Leu Phe Thr
1345                1350                1355                1360

Val Ser Thr Gly Glu Gly Trp Pro Met Val Leu Lys His Ser Val Asp
            1365                1370                1375

Ala Thr Tyr Glu Glu Gln Gly Pro Ser Pro Gly Tyr Arg Met Glu Leu
            1380                1385                1390

Ser Ile Phe Tyr Val Val Tyr Phe Val Val Phe Pro Phe Phe Phe Val
            1395                1400                1405

Asn Ile Phe Val Ala Leu Ile Ile Ile Thr Phe Gln Glu Gln Gly Asp
            1410                1415                1420

Lys Val Met Ser Glu Cys Ser Leu Glu Lys Asn Glu Arg Ala Cys Ile
1425                1430                1435                1440

Asp Phe Ala Ile Ser Ala Lys Pro Leu Thr Arg Tyr Met Pro Gln Asn
            1445                1450                1455

-continued

```
Arg Gln Ser Phe Gln Tyr Lys Thr Trp Thr Phe Val Val Ser Pro Pro
            1460                1465                1470

Phe Glu Tyr Phe Ile Met Ala Met Ile Ala Leu Asn Thr Val Val Leu
        1475                1480                1485

Met Met Lys Phe Tyr Asp Ala Pro Tyr Glu Tyr Glu Leu Met Leu Lys
1490                1495                1500

Cys Leu Asn Ile Val Phe Thr Ser Met Phe Ser Met Glu Cys Val Leu
1505                1510                1515                1520

Lys Ile Ile Ala Phe Gly Val Leu Asn Tyr Phe Arg Asp Ala Trp Asn
            1525                1530                1535

Val Phe Asp Phe Val Thr Val Leu Gly Ser Ile Thr Asp Ile Leu Val
            1540                1545                1550

Thr Glu Ile Ala Glu Thr Asn Asn Phe Ile Asn Leu Ser Phe Leu Arg
        1555                1560                1565

Leu Phe Arg Ala Ala Arg Leu Ile Lys Leu Leu Arg Gln Gly Tyr Thr
        1570                1575                1580

Ile Arg Ile Leu Leu Trp Thr Phe Val Gln Ser Phe Lys Ala Leu Pro
1585                1590                1595                1600

Tyr Val Cys Leu Leu Ile Ala Met Leu Phe Phe Ile Tyr Ala Ile Ile
            1605                1610                1615

Gly Met Gln Val Phe Gly Asn Ile Ala Leu Asp Asp Asp Thr Ser Ile
            1620                1625                1630

Asn Arg His Asn Asn Phe Arg Thr Phe Leu Gln Ala Leu Met Leu Leu
        1635                1640                1645

Phe Arg Ser Ala Thr Gly Glu Ala Trp His Glu Ile Met Leu Ser Cys
        1650                1655                1660

Leu Ser Asn Gln Ala Cys Asp Glu Gln Ala Asn Ala Thr Glu Cys Gly
1665                1670                1675                1680

Ser Asp Phe Ala Tyr Phe Tyr Phe Val Ser Phe Ile Phe Leu Cys Ser
            1685                1690                1695

Phe Leu Met Leu Asn Leu Phe Val Ala Val Ile Met Asp Asn Phe Glu
        1700                1705                1710

Tyr Leu Thr Arg Asp Ser Ser Ile Leu Gly Pro His His Leu Asp Glu
        1715                1720                1725

Phe Ile Arg Val Trp Ala Glu Tyr Asp Pro Ala Ala Cys Gly Arg Ile
        1730                1735                1740

Ser Tyr Asn Asp Met Phe Glu Met Leu Lys His Met Ser Pro Pro Leu
1745                1750                1755                1760

Gly Leu Gly Lys Lys Cys Pro Ala Arg Val Ala Tyr Lys Arg Leu Val
            1765                1770                1775

Arg Met Asn Met Pro Ile Ser Asn Glu Asp Met Thr Val His Phe Thr
            1780                1785                1790

Ser Thr Leu Met Ala Leu Ile Arg Thr Ala Leu Glu Ile Lys Leu Ala
        1795                1800                1805

Pro Ala Gly Thr Lys Gln His Gln Cys Asp Ala Glu Leu Arg Lys Glu
        1810                1815                1820

Ile Ser Val Val Trp Ala Asn Leu Pro Gln Lys Thr Leu Asp Leu Leu
1825                1830                1835                1840

Val Pro Pro His Lys Pro Asp Glu Met Thr Val Gly Lys Val Tyr Ala
            1845                1850                1855

Ala Leu Met Ile Phe Asp Phe Tyr Lys Gln Asn Lys Thr Thr Arg Asp
            1860                1865                1870

Gln Met Gln Gln Ala Pro Gly Gly Leu Ser Gln Met Gly Pro Val Ser
```

-continued

```
            1875                1880                1885
Leu Phe His Pro Leu Lys Ala Thr Leu Glu Gln Thr Gln Pro Ala Val
    1890                1895                1900
Leu Arg Gly Ala Arg Val Phe Leu Arg Gln Lys Ser Ser Thr Ser Leu
1905                1910                1915                1920
Ser Asn Gly Gly Ala Ile Gln Asn Gln Glu Ser Gly Ile Lys Glu Ser
            1925                1930                1935
Val Ser Trp Gly Thr Gln Arg Thr Gln Asp Ala Pro His Glu Ala Arg
        1940                1945                1950
Pro Pro Leu Glu Arg Gly His Ser Thr Glu Ile Pro Val Gly Arg Ser
        1955                1960                1965
Gly Ala Leu Ala Val Asp Val Gln Met Gln Ser Ile Thr Arg Arg Gly
        1970                1975                1980
Pro Asp Gly Glu Pro Gln Pro Gly Leu Glu Ser Gln Gly Arg Ala Ala
1985                1990                1995                2000
Ser Met Pro Arg Leu Ala Ala Glu Thr Gln Pro Val Thr Asp Ala Ser
            2005                2010                2015
Pro Met Lys Arg Ser Ile Ser Thr Leu Ala Gln Arg Pro Arg Gly Thr
            2020                2025                2030
His Leu Cys Ser Thr Thr Pro Asp Arg Pro Pro Ser Gln Ala Ser
            2035                2040                2045
Ser His His His His Arg Cys His Arg Arg Asp Arg Lys Gln
    2050                2055                2060
Arg Ser Leu Glu Lys Gly Pro Ser Leu Ser Ala Asp Met Asp Gly Ala
2065                2070                2075                2080
Pro Ser Ser Ala Val Gly Pro Gly Leu Pro Pro Gly Glu Gly Pro Thr
            2085                2090                2095
Gly Cys Arg Arg Glu Arg Glu Arg Gln Glu Arg Gly Arg Ser Gln
        2100                2105                2110
Glu Arg Arg Gln Pro Ser Ser Ser Ser Glu Lys Gln Arg Phe Tyr
    2115                2120                2125
Ser Cys Asp Arg Phe Gly Gly Arg Glu Pro Pro Lys Pro Lys Pro Ser
    2130                2135                2140
Leu Ser Ser His Pro Thr Ser Pro Thr Ala Gly Gln Glu Pro Gly Pro
2145                2150                2155                2160
His Pro Gln Gly Ser Gly Ser Val Asn Gly Ser Pro Leu Leu Ser Thr
            2165                2170                2175
Ser Gly Ala Ser Thr Pro Gly Arg Gly Gly Arg Arg Gln Leu Pro Gln
            2180                2185                2190
Thr Pro Leu Thr Pro Arg Pro Ser Ile Thr Tyr Lys Thr Ala Asn Ser
        2195                2200                2205
Ser Pro Ile His Phe Ala Gly Ala Gln Thr Ser Leu Pro Ala Phe Ser
    2210                2215                2220
Pro Gly Arg Leu Ser Arg Gly Leu Ser Glu His Asn Ala Leu Leu Gln
2225                2230                2235                2240
Arg Asp Pro Leu Ser Gln Pro Leu Ala Pro Gly Ser Arg Ile Gly Ser
            2245                2250                2255
Asp Pro Tyr Leu Gly Gln Arg Leu Asp Ser Glu Ala Ser Val His Ala
        2260                2265                2270
Leu Pro Glu Asp Thr Leu Thr Phe Glu Glu Ala Val Ala Thr Asn Ser
        2275                2280                2285
Gly Arg Ser Ser Arg Thr Ser Tyr Val Ser Ser Leu Thr Ser Gln Ser
2290                2295                2300
```

-continued

```
His Pro Leu Arg Arg Val Pro Asn Gly Tyr His Cys Thr Leu Gly Leu
2305                2310                2315                2320

Ser Ser Gly Gly Arg Ala Arg His Ser Tyr His His Pro Asp Gln Asp
                2325                2330                2335

His Trp Cys

<210> SEQ ID NO 7
<211> LENGTH: 7177
<212> TYPE: DNA
<213> ORGANISM: Homo sapiens
<220> FEATURE:
<221> NAME/KEY: CDS
<222> LOCATION: 146..6856

<400> SEQUENCE: 7
gcggcggcgg ctgcggcggt ggggccgggc gaggtccgct gcggtcccgg cggctccgtg      60
gctgctccgc tctgagcgcc tggcgcgccc cgcgccctcc ctgccggggc cgctgggccg     120
gggatgcacg cggggcccgg gagcc atg gtc cgc ttc ggg gac gag ctg ggc       172
                            Met Val Arg Phe Gly Asp Glu Leu Gly
                            1               5 ggc cgc tat gga ggc ccc ggc ggc gga gag cgg gcc cgg ggc ggc ggg       220
Gly Arg Tyr Gly Gly Pro Gly Gly Gly Glu Arg Ala Arg Gly Gly Gly
10              15                  20                  25 gcc ggc ggg gcg ggg ggc ccg ggt ccc ggg ggg ctg cag ccc ggc cag       268
Ala Gly Gly Ala Gly Gly Pro Gly Pro Gly Gly Leu Gln Pro Gly Gln
                30                  35                  40 cgg gtc ctc tac aag caa tcg atc gcg cag cgc gcg cgg acc atg gcg       316
Arg Val Leu Tyr Lys Gln Ser Ile Ala Gln Arg Ala Arg Thr Met Ala
            45                  50                  55 ctg tac aac ccc atc ccg gtc aag cag aac tgc ttc acc gtc aac cgc       364
Leu Tyr Asn Pro Ile Pro Val Lys Gln Asn Cys Phe Thr Val Asn Arg
        60                  65                  70 tcg ctc ttc gtc ttc agc gag gac aac gtc gtc cgc aaa tac gcg aag       412
Ser Leu Phe Val Phe Ser Glu Asp Asn Val Val Arg Lys Tyr Ala Lys
    75                  80                  85 cgc atc acc gag tgg cct cca ttc gag tat atg atc ctg gcc acc atc       460
Arg Ile Thr Glu Trp Pro Pro Phe Glu Tyr Met Ile Leu Ala Thr Ile
90                  95                 100                 105 atc gcc aac tgc atc gtg ctg gcc ctg gag cag cac ctc cct gat ggg       508
Ile Ala Asn Cys Ile Val Leu Ala Leu Glu Gln His Leu Pro Asp Gly
                110                 115                 120 gac aaa acg ccc atg tcc gag cgg ctg gac gac acg gag ccc tat ttc       556
Asp Lys Thr Pro Met Ser Glu Arg Leu Asp Asp Thr Glu Pro Tyr Phe
            125                 130                 135 atc ggg atc ttt tgc ttc gag gca ggg atc aaa atc atc gct ctg ggc       604
Ile Gly Ile Phe Cys Phe Glu Ala Gly Ile Lys Ile Ile Ala Leu Gly
        140                 145                 150 ttt gtc ttc cac aag ggc tct tac ctg cgg aac ggc tgg aac gtc atg       652
Phe Val Phe His Lys Gly Ser Tyr Leu Arg Asn Gly Trp Asn Val Met
    155                 160                 165 gac ttc gtg gtc gtc ctc aca ggg atc ctt gcc acg gct gga act gac       700
Asp Phe Val Val Val Leu Thr Gly Ile Leu Ala Thr Ala Gly Thr Asp
170                 175                 180                 185 ttc gac ctg cga aca ctg agg gct gtg cgt gtg ctg agg ccc ctg aag       748
Phe Asp Leu Arg Thr Leu Arg Ala Val Arg Val Leu Arg Pro Leu Lys
                190                 195                 200 ctg gtg tct ggg att cca agt ttg cag gtg gtg ctc aag tcc atc atg       796
Leu Val Ser Gly Ile Pro Ser Leu Gln Val Val Leu Lys Ser Ile Met
            205                 210                 215
```

-continued

| | |
|---|---|
| aag gcc atg gtt cca ctc ctg cag att ggg ctg ctt ctc ttc ttt gcc<br>Lys Ala Met Val Pro Leu Leu Gln Ile Gly Leu Leu Leu Phe Phe Ala<br>220                            225                        230 | 844 |
| atc ctc atg ttt gcc atc att ggc ctg gag ttc tac atg ggc aag ttc<br>Ile Leu Met Phe Ala Ile Ile Gly Leu Glu Phe Tyr Met Gly Lys Phe<br>235                            240                        245 | 892 |
| cac aag gcc tgt ttc ccc aac agc aca gat gcg gag ccc gtg ggt gac<br>His Lys Ala Cys Phe Pro Asn Ser Thr Asp Ala Glu Pro Val Gly Asp<br>250                            255                        260                        265 | 940 |
| ttc ccc tgt ggc aag gag gcc cca gcc cgg ctg tgc gag ggc gac act<br>Phe Pro Cys Gly Lys Glu Ala Pro Ala Arg Leu Cys Glu Gly Asp Thr<br>                  270                        275                        280 | 988 |
| gag tgc cgg gag tac tgg cca gga ccc aac ttt ggc atc acc aac ttt<br>Glu Cys Arg Glu Tyr Trp Pro Gly Pro Asn Phe Gly Ile Thr Asn Phe<br>                  285                        290                        295 | 1036 |
| gac aat atc ctg ttt gcc atc ttg acg gtg ttc cag tgc atc acc atg<br>Asp Asn Ile Leu Phe Ala Ile Leu Thr Val Phe Gln Cys Ile Thr Met<br>300                            305                        310 | 1084 |
| gag ggc tgg act gac atc ctc tat aat aca aac gat gcg gcc ggc aac<br>Glu Gly Trp Thr Asp Ile Leu Tyr Asn Thr Asn Asp Ala Ala Gly Asn<br>315                            320                        325 | 1132 |
| acc tgg aac tgg ctc tac ttc atc cct ctc atc atc atc ggc tcc ttc<br>Thr Trp Asn Trp Leu Tyr Phe Ile Pro Leu Ile Ile Ile Gly Ser Phe<br>330                            335                        340                        345 | 1180 |
| ttc atg ctc aac ctg gtg ctg ggc gtg ctc tcg ggg gag ttt gcc aag<br>Phe Met Leu Asn Leu Val Leu Gly Val Leu Ser Gly Glu Phe Ala Lys<br>                  350                        355                        360 | 1228 |
| gag cga gag agg gtg gag aac cgc cgc gcc ttc ctg aag ctg cgc cgg<br>Glu Arg Glu Arg Val Glu Asn Arg Arg Ala Phe Leu Lys Leu Arg Arg<br>                  365                        370                        375 | 1276 |
| cag cag cag atc gag cga gag ctc aac ggg tac ctg gag tgg atc ttc<br>Gln Gln Gln Ile Glu Arg Glu Leu Asn Gly Tyr Leu Glu Trp Ile Phe<br>                  380                        385                        390 | 1324 |
| aag gcg gag gaa gtc atg ctg gcc gag gag gac agg aat gca gag gag<br>Lys Ala Glu Glu Val Met Leu Ala Glu Glu Asp Arg Asn Ala Glu Glu<br>395                            400                        405 | 1372 |
| aag tcc cct ttg gac gtg ctg aag aga gcg gcc acc aag aag agc aga<br>Lys Ser Pro Leu Asp Val Leu Lys Arg Ala Ala Thr Lys Lys Ser Arg<br>410                            415                        420                        425 | 1420 |
| aat gac ctg atc cac gca gag gag gga gag gac cgg ttt gca gat ctc<br>Asn Asp Leu Ile His Ala Glu Glu Gly Glu Asp Arg Phe Ala Asp Leu<br>                  430                        435                        440 | 1468 |
| tgt gct gtt gga tcc ccc ttc gcc cgc gcc agc ctc aag agc ggg aag<br>Cys Ala Val Gly Ser Pro Phe Ala Arg Ala Ser Leu Lys Ser Gly Lys<br>                  445                        450                        455 | 1516 |
| aca gag agc tcg tca tac ttc cgg agg aag gag aag atg ttc cgg ttt<br>Thr Glu Ser Ser Ser Tyr Phe Arg Arg Lys Glu Lys Met Phe Arg Phe<br>460                            465                        470 | 1564 |
| ttt atc cgg cgc atg gtg aag gct cag agc ttc tac tgg gtg gtg ctg<br>Phe Ile Arg Arg Met Val Lys Ala Gln Ser Phe Tyr Trp Val Val Leu<br>475                            480                        485 | 1612 |
| tgc gtg gtg gcc ctg aac aca ctg tgt gtg gcc atg gtg cat tac aac<br>Cys Val Val Ala Leu Asn Thr Leu Cys Val Ala Met Val His Tyr Asn<br>490                            495                        500                        505 | 1660 |
| cag ccg cgg cgg ctt acc acg acc ctg tat ttt gca gag ttt gtt ttc<br>Gln Pro Arg Arg Leu Thr Thr Thr Leu Tyr Phe Ala Glu Phe Val Phe<br>                  510                        515                        520 | 1708 |
| ctg ggt ctc ttc ctc aca gag atg tcc ctg aag atg tat ggc ctg ggg<br>Leu Gly Leu Phe Leu Thr Glu Met Ser Leu Lys Met Tyr Gly Leu Gly | 1756 |

-continued

```
                525                     530                     535
ccc aga agc tac ttc cgg tcc tcc ttc aac tgc ttc gac ttt ggg gtc    1804
Pro Arg Ser Tyr Phe Arg Ser Ser Phe Asn Cys Phe Asp Phe Gly Val
            540                     545                 550 atc gtg ggg agc gtc ttt gaa gtg gtc tgg gcg gcc atc aag ccg gga    1852
Ile Val Gly Ser Val Phe Glu Val Val Trp Ala Ala Ile Lys Pro Gly
555                     560                     565 agc tcc ttt ggg atc agt gtg ctg cgg gcc ctc cgc ctg ctg agg atc    1900
Ser Ser Phe Gly Ile Ser Val Leu Arg Ala Leu Arg Leu Leu Arg Ile
570                     575                     580                     585 ttc aaa gtc acg aag tac tgg agc tcc ctg cgg aac ctg gtg gtg tcc    1948
Phe Lys Val Thr Lys Tyr Trp Ser Ser Leu Arg Asn Leu Val Val Ser
                590                     595                     600 ctg ctg aac tcc atg aag tcc atc atc agc ctg ctc ttc ttg ctc ttc    1996
Leu Leu Asn Ser Met Lys Ser Ile Ile Ser Leu Leu Phe Leu Leu Phe
                605                     610                     615 ctg ttc att gtg gtc ttc gcc ctg ctg ggg atg cag ctg ttt ggg gga    2044
Leu Phe Ile Val Val Phe Ala Leu Leu Gly Met Gln Leu Phe Gly Gly
            620                     625                     630 cag ttc aac ttc cag gat gag act ccc aca acc aac ttc gac acc ttc    2092
Gln Phe Asn Phe Gln Asp Glu Thr Pro Thr Thr Asn Phe Asp Thr Phe
        635                     640                     645 cct gcc gcc atc ctc act gtc ttc cag atc ctg acg gga gag gac tgg    2140
Pro Ala Ala Ile Leu Thr Val Phe Gln Ile Leu Thr Gly Glu Asp Trp
650                     655                     660                     665 aat gca gtg atg tat cac ggg atc gaa tcg caa ggc ggc gtc agc aaa    2188
Asn Ala Val Met Tyr His Gly Ile Glu Ser Gln Gly Gly Val Ser Lys
                670                     675                     680 ggc atg ttc tcg tcc ttt tac ttc att gtc ctg aca ctg ttc gga aac    2236
Gly Met Phe Ser Ser Phe Tyr Phe Ile Val Leu Thr Leu Phe Gly Asn
            685                     690                     695 tac act ctg ctg aat gtc ttt ctg gcc atc gct gtg gac aac ctg gcc    2284
Tyr Thr Leu Leu Asn Val Phe Leu Ala Ile Ala Val Asp Asn Leu Ala
        700                     705                     710 aac gcc caa gag ctg acc aag gat gaa gag gag atg gaa gaa gca gcc    2332
Asn Ala Gln Glu Leu Thr Lys Asp Glu Glu Glu Met Glu Glu Ala Ala
    715                     720                     725 aat cag aag ctt gct ctg caa aag gcc aaa gaa gtg gct gaa gtc agc    2380
Asn Gln Lys Leu Ala Leu Gln Lys Ala Lys Glu Val Ala Glu Val Ser
730                     735                     740                     745 ccc atg tct gcc gcg aac atc tcc atc gcc gcc agg cag cag aac tcg    2428
Pro Met Ser Ala Ala Asn Ile Ser Ile Ala Ala Arg Gln Gln Asn Ser
                750                     755                     760 gcc aag gcg cgc tcg gtg tgg gag cag cgg gcc agc cag cta cgg ctg    2476
Ala Lys Ala Arg Ser Val Trp Glu Gln Arg Ala Ser Gln Leu Arg Leu
            765                     770                     775 cag aac ctg cgg gcc agc tgc gag gcg ctg tac agc gag atg gac ccc    2524
Gln Asn Leu Arg Ala Ser Cys Glu Ala Leu Tyr Ser Glu Met Asp Pro
        780                     785                     790 gag gag cgg ctg cgc ttc gcc act acg cgc cac ctg cgg ccc gac atg    2572
Glu Glu Arg Leu Arg Phe Ala Thr Thr Arg His Leu Arg Pro Asp Met
    795                     800                     805 aag acg cac ctg gac cgg ccg ctg gtg gtg gag ctg ggc cgc gac ggc    2620
Lys Thr His Leu Asp Arg Pro Leu Val Val Glu Leu Gly Arg Asp Gly
810                     815                     820                     825 gcg cgg ggg ccc gtg gga ggc aaa gcc cga cct gag gct gcg gag gcc    2668
Ala Arg Gly Pro Val Gly Gly Lys Ala Arg Pro Glu Ala Ala Glu Ala
                830                     835                     840 ccc gag ggc gtc gac cct ccg cgc agg cac cac cgg cac cgc gac aag    2716
```

```
                                    -continued

Pro Glu Gly Val Asp Pro Pro Arg Arg His His Arg His Arg Asp Lys
            845                 850                 855 gac aag acc ccc gcg gcg ggg gac cag gac cga gca gag gcc ccg aag    2764
Asp Lys Thr Pro Ala Ala Gly Asp Gln Asp Arg Ala Glu Ala Pro Lys
            860                 865                 870 gcg gag agc ggg gag ccc ggt gcc cgg gag gag cgg ccg cgg ccg cac    2812
Ala Glu Ser Gly Glu Pro Gly Ala Arg Glu Glu Arg Pro Arg Pro His
        875                 880                 885 cgc agc cac agc aag gag gcc gcg ggg ccc ccg gag gcg cgg agc gag    2860
Arg Ser His Ser Lys Glu Ala Ala Gly Pro Pro Glu Ala Arg Ser Glu
890                 895                 900                 905 cgc ggc cga ggc cca ggc ccc gag ggc ggc cgg cgg cac cac cgg cgc    2908
Arg Gly Arg Gly Pro Gly Pro Glu Gly Gly Arg Arg His His Arg Arg
                910                 915                 920 ggc tcc ccg gag gag gcg gcc gag cgg gag ccc cga cgc cac cgc gcg    2956
Gly Ser Pro Glu Glu Ala Ala Glu Arg Glu Pro Arg Arg His Arg Ala
            925                 930                 935 cac cgg cac cag gat ccg agc aag gag tgc gcc ggc gcc aag ggc gag    3004
His Arg His Gln Asp Pro Ser Lys Glu Cys Ala Gly Ala Lys Gly Glu
        940                 945                 950 cgg cgc gcg cgg cac cgc ggc ggc ccc cga gcg ggg ccc cgg gag gcg    3052
Arg Arg Ala Arg His Arg Gly Gly Pro Arg Ala Gly Pro Arg Glu Ala
    955                 960                 965 gag agc ggg gag gag ccg gcg cgg cgg cac cgg gcc cgg cac aag gcg    3100
Glu Ser Gly Glu Glu Pro Ala Arg Arg His Arg Ala Arg His Lys Ala
970                 975                 980                 985 cag cct gct cac gag gct gtg gag aag gag acc acg gag aag gag gcc    3148
Gln Pro Ala His Glu Ala Val Glu Lys Glu Thr Thr Glu Lys Glu Ala
                990                 995                 1000 acg gag aag gag gct gag ata gtg gaa gcc gac aag gaa aag gag ctc    3196
Thr Glu Lys Glu Ala Glu Ile Val Glu Ala Asp Lys Glu Lys Glu Leu
            1005                1010                1015 cgg aac cac cag ccc cgg gag cca cac tgt gac ctg gag acc agt ggg    3244
Arg Asn His Gln Pro Arg Glu Pro His Cys Asp Leu Glu Thr Ser Gly
        1020                1025                1030 act gtg act gtg ggt ccc atg cac aca ctg ccc agc acc tgt ctc cag    3292
Thr Val Thr Val Gly Pro Met His Thr Leu Pro Ser Thr Cys Leu Gln
    1035                1040                1045 aag gtg gag gaa cag cca gag gat gca gac aat cag cgg aac gtc act    3340
Lys Val Glu Glu Gln Pro Glu Asp Ala Asp Asn Gln Arg Asn Val Thr
1050                1055                1060                1065 cgc atg ggc agt cag ccc cca gac ccg aac act att gta cat atc cca    3388
Arg Met Gly Ser Gln Pro Pro Asp Pro Asn Thr Ile Val His Ile Pro
                1070                1075                1080 gtg atg ctg acg ggc cct ctt ggg gaa gcc acg gtc gtt ccc agt ggt    3436
Val Met Leu Thr Gly Pro Leu Gly Glu Ala Thr Val Val Pro Ser Gly
            1085                1090                1095 aac gtg gac ctg gaa agc caa gca gag ggg aag aag gag gtg gaa gcg    3484
Asn Val Asp Leu Glu Ser Gln Ala Glu Gly Lys Lys Glu Val Glu Ala
        1100                1105                1110 gat gac gtg atg agg agc ggc ccc cgg cct atc gtc cca tac agc tcc    3532
Asp Asp Val Met Arg Ser Gly Pro Arg Pro Ile Val Pro Tyr Ser Ser
    1115                1120                1125 atg ttc tgt tta agc ccc acc aac ctg ctc cgc cgc ttc tgc cac tac    3580
Met Phe Cys Leu Ser Pro Thr Asn Leu Leu Arg Arg Phe Cys His Tyr
1130                1135                1140                1145 atc gtg acc atg agg tac ttc gag gtg gtc att ctc gtg gtc atc gcc    3628
Ile Val Thr Met Arg Tyr Phe Glu Val Val Ile Leu Val Val Ile Ala
                1150                1155                1160
```

```
                                                              -continued ttg agc agc atc gcc ctg gct gct gag gac cca gtg cgc aca gac tcg        3676
Leu Ser Ser Ile Ala Leu Ala Ala Glu Asp Pro Val Arg Thr Asp Ser
        1165                1170                1175 ccc agg aac aac gct ctg aaa tac ctg gat tac att ttc act ggt gtc        3724
Pro Arg Asn Asn Ala Leu Lys Tyr Leu Asp Tyr Ile Phe Thr Gly Val
    1180                1185                1190 ttt acc ttt gag atg gtg ata aag atg atc gac ttg gga ctg ctg ctt        3772
Phe Thr Phe Glu Met Val Ile Lys Met Ile Asp Leu Gly Leu Leu Leu
1195                1200                1205 cac cct gga gcc tat ttc cgg gac ttg tgg aac att ctg gac ttc att        3820
His Pro Gly Ala Tyr Phe Arg Asp Leu Trp Asn Ile Leu Asp Phe Ile
1210                1215                1220                1225 gtg gtc agt ggc gcc ctg gtg gcg ttt gct ttc tca gga tcc aaa ggg        3868
Val Val Ser Gly Ala Leu Val Ala Phe Ala Phe Ser Gly Ser Lys Gly
            1230                1235                1240 aaa gac atc aat acc atc aag tct ctg aga gtc ctt cgt gtc ctg cgg        3916
Lys Asp Ile Asn Thr Ile Lys Ser Leu Arg Val Leu Arg Val Leu Arg
        1245                1250                1255 ccc ctc aag acc atc aaa cgg ctg ccc aag ctc aag gct gtg ttt gac        3964
Pro Leu Lys Thr Ile Lys Arg Leu Pro Lys Leu Lys Ala Val Phe Asp
    1260                1265                1270 tgt gtg gtg aac tcc ctg aag aat gtc ctc aac atc ttg att gtc tac        4012
Cys Val Val Asn Ser Leu Lys Asn Val Leu Asn Ile Leu Ile Val Tyr
    1275                1280                1285 atg ctc ttc atg ttc ata ttt gcc gtc att gcg gtg cag ctc ttc aaa        4060
Met Leu Phe Met Phe Ile Phe Ala Val Ile Ala Val Gln Leu Phe Lys
1290                1295                1300                1305 ggg aag ttt ttc tac tgc aca gat gaa tcc aag gag ctg gag agg gac        4108
Gly Lys Phe Phe Tyr Cys Thr Asp Glu Ser Lys Glu Leu Glu Arg Asp
            1310                1315                1320 tgc agg ggt cag tat ttg gat tat gag aag gag gaa gtg gaa gct cag        4156
Cys Arg Gly Gln Tyr Leu Asp Tyr Glu Lys Glu Glu Val Glu Ala Gln
        1325                1330                1335 ccc agg cag tgg aag aaa tac gac ttt cac tac gac aat gtg ctc tgg        4204
Pro Arg Gln Trp Lys Lys Tyr Asp Phe His Tyr Asp Asn Val Leu Trp
    1340                1345                1350 gct ctg ctg acg ctg ttc aca gtg tcc acg gga gaa ggc tgg ccc atg        4252
Ala Leu Leu Thr Leu Phe Thr Val Ser Thr Gly Glu Gly Trp Pro Met
1355                1360                1365 gtg ctg aaa cac tcc gtg gat gcc acc tat gag gag cag ggt cca agc        4300
Val Leu Lys His Ser Val Asp Ala Thr Tyr Glu Glu Gln Gly Pro Ser
1370                1375                1380                1385 cct ggg tac cgc atg gag ctg tcc atc ttc tac gtg gtc tac ttt gtg        4348
Pro Gly Tyr Arg Met Glu Leu Ser Ile Phe Tyr Val Val Tyr Phe Val
            1390                1395                1400 gtc ttt ccc ttc ttc gtc aac atc ttt gtg gct ttg atc atc atc            4396
Val Phe Pro Phe Phe Val Asn Ile Phe Val Ala Leu Ile Ile Ile
        1405                1410                1415 acc ttc cag gag cag ggg gac aag gtg atg tct gaa tgc agc ctg gag        4444
Thr Phe Gln Glu Gln Gly Asp Lys Val Met Ser Glu Cys Ser Leu Glu
    1420                1425                1430 aag aac gag agg gct tgc att gac ttc gcc atc agc gcc aaa ccc ctg        4492
Lys Asn Glu Arg Ala Cys Ile Asp Phe Ala Ile Ser Ala Lys Pro Leu
1435                1440                1445 aca cgg tac atg ccc caa aac cgg cag tcg ttc cag tat aag acg tgg        4540
Thr Arg Tyr Met Pro Gln Asn Arg Gln Ser Phe Gln Tyr Lys Thr Trp
1450                1455                1460                1465 aca ttt gtg gtc tcc ccg ccc ttt gaa tac ttc atc atg gcc atg ata        4588
Thr Phe Val Val Ser Pro Pro Phe Glu Tyr Phe Ile Met Ala Met Ile
            1470                1475                1480
```

```
gcc ctc aac act gtg gtg ctg atg atg aag ttc tat gat gca ccc tat    4636
Ala Leu Asn Thr Val Val Leu Met Met Lys Phe Tyr Asp Ala Pro Tyr
            1485                1490                1495 gag tac gag ctg atg ctg aaa tgc ctg aac atc gtg ttc aca tcc atg    4684
Glu Tyr Glu Leu Met Leu Lys Cys Leu Asn Ile Val Phe Thr Ser Met
        1500                1505                1510 ttc tcc atg gaa tgc gtg ctg aag atc atc gcc ttt ggg gtg ctg aac    4732
Phe Ser Met Glu Cys Val Leu Lys Ile Ile Ala Phe Gly Val Leu Asn
    1515                1520                1525 tat ttc aga gat gcc tgg aat gtc ttt gac ttt gtc act gtg ttg gga    4780
Tyr Phe Arg Asp Ala Trp Asn Val Phe Asp Phe Val Thr Val Leu Gly
1530                1535                1540                1545 agt att act gat att tta gta aca gag att gcg gaa acg aac aat ttc    4828
Ser Ile Thr Asp Ile Leu Val Thr Glu Ile Ala Glu Thr Asn Asn Phe
            1550                1555                1560 atc aac ctc agc ttc ctc cgc ctc ttt cga gct gcg cgg ctg atc aag    4876
Ile Asn Leu Ser Phe Leu Arg Leu Phe Arg Ala Ala Arg Leu Ile Lys
        1565                1570                1575 ctg ctc cgc cag ggc tac acc atc cgc atc ctg ctg tgg acc ttt gtc    4924
Leu Leu Arg Gln Gly Tyr Thr Ile Arg Ile Leu Leu Trp Thr Phe Val
    1580                1585                1590 cag tcc ttc aag gcc ctg ccc tac gtg tgt ctg ctc att gcc atg ctg    4972
Gln Ser Phe Lys Ala Leu Pro Tyr Val Cys Leu Leu Ile Ala Met Leu
1595                1600                1605 ttc ttc atc tac gcc atc atc ggc atg cag gtg ttt ggg aat att gcc    5020
Phe Phe Ile Tyr Ala Ile Ile Gly Met Gln Val Phe Gly Asn Ile Ala
1610                1615                1620                1625 ctg gat gat gac acc agc atc aac cgc cac aac aac ttc cgg acg ttt    5068
Leu Asp Asp Asp Thr Ser Ile Asn Arg His Asn Asn Phe Arg Thr Phe
            1630                1635                1640 ttg caa gcc ctg atg ctg ctg ttc agg agc gcc acg ggg gag gcc tgg    5116
Leu Gln Ala Leu Met Leu Leu Phe Arg Ser Ala Thr Gly Glu Ala Trp
        1645                1650                1655 cac gag atc atg ctg tcc tgc ctg agc aac cag gcc tgt gat gag cag    5164
His Glu Ile Met Leu Ser Cys Leu Ser Asn Gln Ala Cys Asp Glu Gln
    1660                1665                1670 gcc aat gcc acc gag tgt gga agt gac ttt gcc tac ttc tac ttc gtc    5212
Ala Asn Ala Thr Glu Cys Gly Ser Asp Phe Ala Tyr Phe Tyr Phe Val
1675                1680                1685 tcc ttc atc ttc ctg tgc tcc ttt ctg atg ttg aac ctc ttt gtg gct    5260
Ser Phe Ile Phe Leu Cys Ser Phe Leu Met Leu Asn Leu Phe Val Ala
1690                1695                1700                1705 gtg atc atg gac aat ttt gag tac ctc acg cgg gac tct tcc atc cta    5308
Val Ile Met Asp Asn Phe Glu Tyr Leu Thr Arg Asp Ser Ser Ile Leu
            1710                1715                1720 ggt cct cac cac ttg gat gag ttc atc cgg gtc tgg gct gaa tac gac    5356
Gly Pro His His Leu Asp Glu Phe Ile Arg Val Trp Ala Glu Tyr Asp
        1725                1730                1735 ccg gct gcg tgt ggg cgc atc agt tac aat gac atg ttt gag atg ctg    5404
Pro Ala Ala Cys Gly Arg Ile Ser Tyr Asn Asp Met Phe Glu Met Leu
    1740                1745                1750 aaa cac atg tcc ccg cct ctg ggg ctg ggg aag aaa tgc cct gct cga    5452
Lys His Met Ser Pro Pro Leu Gly Leu Gly Lys Lys Cys Pro Ala Arg
1755                1760                1765 gtt gct tac aag cgc ctg gtt cgc atg aac atg ccc atc tcc aac gag    5500
Val Ala Tyr Lys Arg Leu Val Arg Met Asn Met Pro Ile Ser Asn Glu
1770                1775                1780                1785 gac atg act gtt cac ttc acg tcc acg ctg atg gcc ctc atc cgg acg    5548
Asp Met Thr Val His Phe Thr Ser Thr Leu Met Ala Leu Ile Arg Thr
```

-continued

```
              1790                1795                1800
gca ctg gag atc aag ctg gcc cca gct ggg aca aag cag cat cag tgt         5596
Ala Leu Glu Ile Lys Leu Ala Pro Ala Gly Thr Lys Gln His Gln Cys
            1805                1810                1815 gac gcg gag ttg agg aag gag att tcc gtt gtg tgg gcc aat ctg ccc         5644
Asp Ala Glu Leu Arg Lys Glu Ile Ser Val Val Trp Ala Asn Leu Pro
        1820                1825                1830 cag aag act ttg gac ttg ctg gta cca ccc cat aag cct gat gag atg         5692
Gln Lys Thr Leu Asp Leu Leu Val Pro Pro His Lys Pro Asp Glu Met
    1835                1840                1845 aca gtg ggg aag gtt tat gca gct ctg atg ata ttt gac ttc tac aag         5740
Thr Val Gly Lys Val Tyr Ala Ala Leu Met Ile Phe Asp Phe Tyr Lys
1850                1855                1860                1865 cag aac aaa acc acc aga gac cag atg cag cag gct cct gga ggc ctc         5788
Gln Asn Lys Thr Thr Arg Asp Gln Met Gln Gln Ala Pro Gly Gly Leu
            1870                1875                1880 tcc cag atg ggt cct gtg tcc ctg ttc cac cct ctg aag gcc acc ctg         5836
Ser Gln Met Gly Pro Val Ser Leu Phe His Pro Leu Lys Ala Thr Leu
        1885                1890                1895 gag cag aca cag ccg gct gtg ctc cga gga gcc cgg gtt ttc ctt cga         5884
Glu Gln Thr Gln Pro Ala Val Leu Arg Gly Ala Arg Val Phe Leu Arg
    1900                1905                1910 cag aag agt tcc acc tcc ctc agc aat ggc ggg gcc ata caa aac caa         5932
Gln Lys Ser Ser Thr Ser Leu Ser Asn Gly Gly Ala Ile Gln Asn Gln
1915                1920                1925 gag agt ggc atc aaa gag tct gtc tcc tgg ggc act caa agg acc cag         5980
Glu Ser Gly Ile Lys Glu Ser Val Ser Trp Gly Thr Gln Arg Thr Gln
1930                1935                1940                1945 gat gca ccc cat gag gcc agg cca ccc ctg gag cgt ggc cac tcc aca         6028
Asp Ala Pro His Glu Ala Arg Pro Pro Leu Glu Arg Gly His Ser Thr
        1950                1955                1960 gag atc cct gtg ggg cgg tca gga gca ctg gct gtg gac gtt cag atg         6076
Glu Ile Pro Val Gly Arg Ser Gly Ala Leu Ala Val Asp Val Gln Met
            1965                1970                1975 cag agc ata acc cgg agg ggc cct gat ggg gag ccc cag cct ggg ctg         6124
Gln Ser Ile Thr Arg Arg Gly Pro Asp Gly Glu Pro Gln Pro Gly Leu
        1980                1985                1990 gag agc cag ggt cga gcg gcc tcc atg ccc cgc ctt gcg gcc gag act         6172
Glu Ser Gln Gly Arg Ala Ala Ser Met Pro Arg Leu Ala Ala Glu Thr
    1995                2000                2005 cag ccc gtc aca gat gcc agc ccc atg aag cgc tcc atc tcc acg ctg         6220
Gln Pro Val Thr Asp Ala Ser Pro Met Lys Arg Ser Ile Ser Thr Leu
2010                2015                2020                2025 gcc cag cgg ccc cgt ggg act cat ctt tgc agc acc acc ccg gac cgc         6268
Ala Gln Arg Pro Arg Gly Thr His Leu Cys Ser Thr Thr Pro Asp Arg
            2030                2035                2040 cca ccc cct agc cag gcg tcg tcg cac cac cac cac cac cgc tgc cac         6316
Pro Pro Pro Ser Gln Ala Ser Ser His His His His His Arg Cys His
        2045                2050                2055 cgc cgc agg gac agg aag cag agg tcc ctg gag aag ggg ccc agc ctg         6364
Arg Arg Arg Asp Arg Lys Gln Arg Ser Leu Glu Lys Gly Pro Ser Leu
    2060                2065                2070 tct gcc gat atg gat ggc gca cca agc agt gct gtg ggg ccg ggg ctg         6412
Ser Ala Asp Met Asp Gly Ala Pro Ser Ser Ala Val Gly Pro Gly Leu
2075                2080                2085 ccc ccg gga gag ggg cct aca ggc tgc cgg cgg gaa cga gag cgc cgg         6460
Pro Pro Gly Glu Gly Pro Thr Gly Cys Arg Arg Glu Arg Glu Arg Arg
2090                2095                2100                2105 cag gag cgg ggc cgg tcc cag gag cgg agg cag ccc tca tcc tcc tcc         6508
```

-continued

| | | | | | | | | | | | | |
|---|---|---|---|---|---|---|---|---|---|---|---|---|
| Gln | Glu | Arg | Gly | Arg | Ser | Gln | Glu | Arg | Arg | Pro | Ser | Ser | Ser | Ser |
| | | | 2110 | | | | | 2115 | | | | 2120 | | |

```
tcg gag aag cag cgc ttc tac tcc tgc gac cgc ttt ggg ggc cgt gag      6556
Ser Glu Lys Gln Arg Phe Tyr Ser Cys Asp Arg Phe Gly Gly Arg Glu
            2125                2130                2135 ccc ccg aag ccc aag ccc tcc ctc agc agc cac cca acg tcg cca aca      6604
Pro Pro Lys Pro Lys Pro Ser Leu Ser Ser His Pro Thr Ser Pro Thr
        2140                2145                2150 gct ggc cag gag ccg gga ccc cac cca cag gcc ggc tca gcc gtg ggc      6652
Ala Gly Gln Glu Pro Gly Pro His Pro Gln Ala Gly Ser Ala Val Gly
    2155                2160                2165 ttt ccg aac aca acg ccc tgc tgc aga gag acc ccc tca gcc agc ccc      6700
Phe Pro Asn Thr Thr Pro Cys Cys Arg Glu Thr Pro Ser Ala Ser Pro
2170                2175                2180                2185 tgg ccc ctg gct ctc gaa ttg gct ctg acc ctt acc tgg ggc agc gtc      6748
Trp Pro Leu Ala Leu Glu Leu Ala Leu Thr Leu Thr Trp Gly Ser Val
            2190                2195                2200 tgg aca gtg agg cct ctg tcc acg ccc tgc ctg agg aca cgc tca ctt      6796
Trp Thr Val Arg Pro Leu Ser Thr Pro Cys Leu Arg Thr Arg Ser Leu
        2205                2210                2215 tcg agg agg ctg tgg cca cca act cgg gcc gct cct cca gga ctt cct      6844
Ser Arg Arg Leu Trp Pro Pro Thr Arg Ala Ala Pro Pro Gly Leu Pro
    2220                2225                2230 acg tgt cct ccc tgacctccca gtctcaccct ctccgccgcg tgcccaacgg ttacc    6901
Thr Cys Pro Pro
   2235 actgcaccct gggactcagc tcgggtggcc gagcacggca cagctaccac caccctgacc   6961 aagaccactg gtgctagctg caccgtgacc gctcagacgc ctgcatgcag caggcgtgtg   7021 ttccagtgga tgagttttat catccacacg gggcagtcgg ccctcggggg aggccttgcc   7081 caccttggtg aggctcctgt ggcccctccc tccccctcct cccctctttt actctagacg   7141 acgaataaag ccctgttgct tgagtgtacg taccgc                             7177

<210> SEQ ID NO 8
<211> LENGTH: 2237
<212> TYPE: PRT
<213> ORGANISM: Homo sapiens

<400> SEQUENCE: 8

Met Val Arg Phe Gly Asp Glu Leu Gly Gly Arg Tyr Gly Gly Pro Gly
 1               5                  10                  15

Gly Gly Glu Arg Ala Arg Gly Gly Ala Gly Gly Ala Gly Gly Pro
            20                  25                  30

Gly Pro Gly Gly Leu Gln Pro Gly Gln Arg Val Leu Tyr Lys Gln Ser
        35                  40                  45

Ile Ala Gln Arg Ala Arg Thr Met Ala Leu Tyr Asn Pro Ile Pro Val
    50                  55                  60

Lys Gln Asn Cys Phe Thr Val Asn Arg Ser Leu Phe Val Phe Ser Glu
65                  70                  75                  80

Asp Asn Val Val Arg Lys Tyr Ala Lys Arg Ile Thr Glu Trp Pro Pro
                85                  90                  95

Phe Glu Tyr Met Ile Leu Ala Thr Ile Ile Ala Asn Cys Ile Val Leu
            100                 105                 110

Ala Leu Glu Gln His Leu Pro Asp Gly Asp Lys Thr Pro Met Ser Glu
        115                 120                 125

Arg Leu Asp Asp Thr Glu Pro Tyr Phe Ile Gly Ile Phe Cys Phe Glu
    130                 135                 140
```

```
Ala Gly Ile Lys Ile Ile Ala Leu Gly Phe Val Phe His Lys Gly Ser
145                 150                 155                 160

Tyr Leu Arg Asn Gly Trp Asn Val Met Asp Phe Val Val Leu Thr
                165                 170                 175

Gly Ile Leu Ala Thr Ala Gly Thr Asp Phe Asp Leu Arg Thr Leu Arg
                180                 185                 190

Ala Val Arg Val Leu Arg Pro Leu Lys Leu Val Ser Gly Ile Pro Ser
            195                 200                 205

Leu Gln Val Val Leu Lys Ser Ile Met Lys Ala Met Val Pro Leu Leu
        210                 215                 220

Gln Ile Gly Leu Leu Phe Ala Ile Leu Met Phe Ala Ile Ile
225                 230                 235                 240

Gly Leu Glu Phe Tyr Met Gly Lys Phe His Lys Ala Cys Phe Pro Asn
                245                 250                 255

Ser Thr Asp Ala Glu Pro Val Gly Asp Phe Pro Cys Gly Lys Glu Ala
                260                 265                 270

Pro Ala Arg Leu Cys Glu Gly Asp Thr Glu Cys Arg Glu Tyr Trp Pro
            275                 280                 285

Gly Pro Asn Phe Gly Ile Thr Asn Phe Asp Asn Ile Leu Phe Ala Ile
        290                 295                 300

Leu Thr Val Phe Gln Cys Ile Thr Met Glu Gly Trp Thr Asp Ile Leu
305                 310                 315                 320

Tyr Asn Thr Asn Asp Ala Ala Gly Asn Thr Trp Asn Trp Leu Tyr Phe
                325                 330                 335

Ile Pro Leu Ile Ile Ile Gly Ser Phe Phe Met Leu Asn Leu Val Leu
                340                 345                 350

Gly Val Leu Ser Gly Glu Phe Ala Lys Glu Arg Glu Arg Val Glu Asn
            355                 360                 365

Arg Arg Ala Phe Leu Lys Leu Arg Arg Gln Gln Ile Glu Arg Glu
370                 375                 380

Leu Asn Gly Tyr Leu Glu Trp Ile Phe Lys Ala Glu Glu Val Met Leu
385                 390                 395                 400

Ala Glu Glu Asp Arg Asn Ala Glu Glu Lys Ser Pro Leu Asp Val Leu
                405                 410                 415

Lys Arg Ala Ala Thr Lys Lys Ser Arg Asn Asp Leu Ile His Ala Glu
                420                 425                 430

Glu Gly Glu Asp Arg Phe Ala Asp Leu Cys Ala Val Gly Ser Pro Phe
            435                 440                 445

Ala Arg Ala Ser Leu Lys Ser Gly Lys Thr Glu Ser Ser Ser Tyr Phe
            450                 455                 460

Arg Arg Lys Glu Lys Met Phe Arg Phe Phe Ile Arg Arg Met Val Lys
465                 470                 475                 480

Ala Gln Ser Phe Tyr Trp Val Val Leu Cys Val Val Ala Leu Asn Thr
                485                 490                 495

Leu Cys Val Ala Met Val His Tyr Asn Gln Pro Arg Arg Leu Thr Thr
                500                 505                 510

Thr Leu Tyr Phe Ala Glu Phe Val Phe Leu Gly Leu Phe Leu Thr Glu
            515                 520                 525

Met Ser Leu Lys Met Tyr Gly Leu Gly Pro Arg Ser Tyr Phe Arg Ser
        530                 535                 540

Ser Phe Asn Cys Phe Asp Phe Gly Val Ile Val Gly Ser Val Phe Glu
545                 550                 555                 560
```

-continued

```
Val Val Trp Ala Ala Ile Lys Pro Gly Ser Ser Phe Gly Ile Ser Val
                565                 570                 575

Leu Arg Ala Leu Arg Leu Leu Arg Ile Phe Lys Val Thr Lys Tyr Trp
            580                 585                 590

Ser Ser Leu Arg Asn Leu Val Val Ser Leu Leu Asn Ser Met Lys Ser
        595                 600                 605

Ile Ile Ser Leu Leu Phe Leu Leu Phe Leu Phe Ile Val Val Phe Ala
    610                 615                 620

Leu Leu Gly Met Gln Leu Phe Gly Gly Gln Phe Asn Phe Gln Asp Glu
625                 630                 635                 640

Thr Pro Thr Thr Asn Phe Asp Thr Phe Pro Ala Ala Ile Leu Thr Val
                645                 650                 655

Phe Gln Ile Leu Thr Gly Glu Asp Trp Asn Ala Val Met Tyr His Gly
            660                 665                 670

Ile Glu Ser Gln Gly Gly Val Ser Lys Gly Met Phe Ser Ser Phe Tyr
        675                 680                 685

Phe Ile Val Leu Thr Leu Phe Gly Asn Tyr Thr Leu Leu Asn Val Phe
    690                 695                 700

Leu Ala Ile Ala Val Asp Asn Leu Ala Asn Ala Gln Glu Leu Thr Lys
705                 710                 715                 720

Asp Glu Glu Glu Met Glu Glu Ala Ala Asn Gln Lys Leu Ala Leu Gln
                725                 730                 735

Lys Ala Lys Glu Val Ala Glu Val Ser Pro Met Ser Ala Ala Asn Ile
            740                 745                 750

Ser Ile Ala Ala Arg Gln Gln Asn Ser Ala Lys Ala Arg Ser Val Trp
        755                 760                 765

Glu Gln Arg Ala Ser Gln Leu Arg Leu Gln Asn Leu Arg Ala Ser Cys
    770                 775                 780

Glu Ala Leu Tyr Ser Glu Met Asp Pro Glu Glu Arg Leu Arg Phe Ala
785                 790                 795                 800

Thr Thr Arg His Leu Arg Pro Asp Met Lys Thr His Leu Asp Arg Pro
                805                 810                 815

Leu Val Val Glu Leu Gly Arg Asp Gly Ala Arg Gly Pro Val Gly Gly
            820                 825                 830

Lys Ala Arg Pro Glu Ala Ala Glu Ala Pro Glu Gly Val Asp Pro Pro
        835                 840                 845

Arg Arg His His Arg His Arg Asp Lys Asp Lys Thr Pro Ala Ala Gly
    850                 855                 860

Asp Gln Asp Arg Ala Glu Ala Pro Lys Ala Glu Ser Gly Glu Pro Gly
865                 870                 875                 880

Ala Arg Glu Glu Arg Pro Arg Pro His Arg Ser His Ser Lys Glu Ala
                885                 890                 895

Ala Gly Pro Pro Glu Ala Arg Ser Glu Arg Gly Arg Gly Pro Gly Pro
            900                 905                 910

Glu Gly Gly Arg Arg His His Arg Arg Gly Ser Pro Glu Ala Ala
        915                 920                 925

Glu Arg Glu Pro Arg Arg His Arg Ala His Arg His Gln Asp Pro Ser
    930                 935                 940

Lys Glu Cys Ala Gly Ala Lys Gly Glu Arg Arg Ala Arg His Arg Gly
945                 950                 955                 960

Gly Pro Arg Ala Gly Pro Arg Glu Ala Glu Ser Gly Glu Glu Pro Ala
                965                 970                 975

Arg Arg His Arg Ala Arg His Lys Ala Gln Pro Ala His Glu Ala Val
```

-continued

```
              980                 985                 990
Glu Lys Glu Thr Thr Glu Lys Glu Ala Thr Glu Lys Glu Ala Glu Ile
        995                1000                1005
Val Glu Ala Asp Lys Glu Lys Glu Leu Arg Asn His Gln Pro Arg Glu
1010                1015                1020
Pro His Cys Asp Leu Glu Thr Ser Gly Thr Val Thr Val Gly Pro Met
1025                1030                1035                1040
His Thr Leu Pro Ser Thr Cys Leu Gln Lys Val Glu Glu Gln Pro Glu
                1045                1050                1055
Asp Ala Asp Asn Gln Arg Asn Val Thr Arg Met Gly Ser Gln Pro Pro
            1060                1065                1070
Asp Pro Asn Thr Ile Val His Ile Pro Val Met Leu Thr Gly Pro Leu
        1075                1080                1085
Gly Glu Ala Thr Val Val Pro Ser Gly Asn Val Asp Leu Glu Ser Gln
    1090                1095                1100
Ala Glu Gly Lys Lys Glu Val Glu Ala Asp Asp Val Met Arg Ser Gly
1105                1110                1115                1120
Pro Arg Pro Ile Val Pro Tyr Ser Ser Met Phe Cys Leu Ser Pro Thr
                1125                1130                1135
Asn Leu Leu Arg Arg Phe Cys His Tyr Ile Val Thr Met Arg Tyr Phe
            1140                1145                1150
Glu Val Val Ile Leu Val Val Ile Ala Leu Ser Ser Ile Ala Leu Ala
        1155                1160                1165
Ala Glu Asp Pro Val Arg Thr Asp Ser Pro Arg Asn Asn Ala Leu Lys
    1170                1175                1180
Tyr Leu Asp Tyr Ile Phe Thr Gly Val Phe Thr Phe Glu Met Val Ile
1185                1190                1195                1200
Lys Met Ile Asp Leu Gly Leu Leu Leu His Pro Gly Ala Tyr Phe Arg
                1205                1210                1215
Asp Leu Trp Asn Ile Leu Asp Phe Ile Val Ser Gly Ala Leu Val
            1220                1225                1230
Ala Phe Ala Phe Ser Gly Ser Lys Gly Lys Asp Ile Asn Thr Ile Lys
        1235                1240                1245
Ser Leu Arg Val Leu Arg Val Leu Arg Pro Leu Lys Thr Ile Lys Arg
    1250                1255                1260
Leu Pro Lys Leu Lys Ala Val Phe Asp Cys Val Val Asn Ser Leu Lys
1265                1270                1275                1280
Asn Val Leu Asn Ile Leu Ile Val Tyr Met Leu Phe Met Phe Ile Phe
                1285                1290                1295
Ala Val Ile Ala Val Gln Leu Phe Lys Gly Lys Phe Phe Tyr Cys Thr
            1300                1305                1310
Asp Glu Ser Lys Glu Leu Glu Arg Asp Cys Arg Gly Gln Tyr Leu Asp
        1315                1320                1325
Tyr Glu Lys Glu Glu Val Glu Ala Gln Pro Arg Gln Trp Lys Lys Tyr
    1330                1335                1340
Asp Phe His Tyr Asp Asn Val Leu Trp Ala Leu Leu Thr Leu Phe Thr
1345                1350                1355                1360
Val Ser Thr Gly Glu Gly Trp Pro Met Val Leu Lys His Ser Val Asp
                1365                1370                1375
Ala Thr Tyr Glu Glu Gln Gly Pro Ser Pro Gly Tyr Arg Met Glu Leu
            1380                1385                1390
Ser Ile Phe Tyr Val Val Tyr Phe Val Val Phe Pro Phe Phe Phe Val
        1395                1400                1405
```

```
Asn Ile Phe Val Ala Leu Ile Ile Ile Thr Phe Gln Glu Gln Gly Asp
            1410                1415                1420
Lys Val Met Ser Glu Cys Ser Leu Glu Lys Asn Glu Arg Ala Cys Ile
1425                1430                1435                1440
Asp Phe Ala Ile Ser Ala Lys Pro Leu Thr Arg Tyr Met Pro Gln Asn
            1445                1450                1455
Arg Gln Ser Phe Gln Tyr Lys Thr Trp Thr Phe Val Val Ser Pro Pro
            1460                1465                1470
Phe Glu Tyr Phe Ile Met Ala Met Ile Ala Leu Asn Thr Val Val Leu
            1475                1480                1485
Met Met Lys Phe Tyr Asp Ala Pro Tyr Glu Tyr Glu Leu Met Leu Lys
            1490                1495                1500
Cys Leu Asn Ile Val Phe Thr Ser Met Phe Ser Met Glu Cys Val Leu
1505                1510                1515                1520
Lys Ile Ile Ala Phe Gly Val Leu Asn Tyr Phe Arg Asp Ala Trp Asn
            1525                1530                1535
Val Phe Asp Phe Val Thr Val Leu Gly Ser Ile Thr Asp Ile Leu Val
            1540                1545                1550
Thr Glu Ile Ala Glu Thr Asn Asn Phe Ile Asn Leu Ser Phe Leu Arg
            1555                1560                1565
Leu Phe Arg Ala Ala Arg Leu Ile Lys Leu Leu Arg Gln Gly Tyr Thr
            1570                1575                1580
Ile Arg Ile Leu Leu Trp Thr Phe Val Gln Ser Phe Lys Ala Leu Pro
1585                1590                1595                1600
Tyr Val Cys Leu Leu Ile Ala Met Leu Phe Phe Ile Tyr Ala Ile Ile
            1605                1610                1615
Gly Met Gln Val Phe Gly Asn Ile Ala Leu Asp Asp Asp Thr Ser Ile
            1620                1625                1630
Asn Arg His Asn Asn Phe Arg Thr Phe Leu Gln Ala Leu Met Leu Leu
            1635                1640                1645
Phe Arg Ser Ala Thr Gly Glu Ala Trp His Glu Ile Met Leu Ser Cys
            1650                1655                1660
Leu Ser Asn Gln Ala Cys Asp Glu Gln Ala Asn Ala Thr Glu Cys Gly
1665                1670                1675                1680
Ser Asp Phe Ala Tyr Phe Tyr Phe Val Ser Phe Ile Phe Leu Cys Ser
            1685                1690                1695
Phe Leu Met Leu Asn Leu Phe Val Ala Val Ile Met Asp Asn Phe Glu
            1700                1705                1710
Tyr Leu Thr Arg Asp Ser Ser Ile Leu Gly Pro His His Leu Asp Glu
            1715                1720                1725
Phe Ile Arg Val Trp Ala Glu Tyr Asp Pro Ala Ala Cys Gly Arg Ile
            1730                1735                1740
Ser Tyr Asn Asp Met Phe Glu Met Leu Lys His Met Ser Pro Pro Leu
1745                1750                1755                1760
Gly Leu Gly Lys Lys Cys Pro Ala Arg Val Ala Tyr Lys Arg Leu Val
            1765                1770                1775
Arg Met Asn Met Pro Ile Ser Asn Glu Asp Met Thr Val His Phe Thr
            1780                1785                1790
Ser Thr Leu Met Ala Leu Ile Arg Thr Ala Leu Glu Ile Lys Leu Ala
            1795                1800                1805
Pro Ala Gly Thr Lys Gln His Gln Cys Asp Ala Glu Leu Arg Lys Glu
            1810                1815                1820
```

```
Ile Ser Val Val Trp Ala Asn Leu Pro Gln Lys Thr Leu Asp Leu Leu
1825                1830                1835                1840

Val Pro Pro His Lys Pro Asp Glu Met Thr Val Gly Lys Val Tyr Ala
                1845                1850                1855

Ala Leu Met Ile Phe Asp Phe Tyr Lys Gln Asn Lys Thr Thr Arg Asp
            1860                1865                1870

Gln Met Gln Gln Ala Pro Gly Gly Leu Ser Gln Met Gly Pro Val Ser
        1875                1880                1885

Leu Phe His Pro Leu Lys Ala Thr Leu Glu Gln Thr Gln Pro Ala Val
    1890                1895                1900

Leu Arg Gly Ala Arg Val Phe Leu Arg Gln Lys Ser Ser Thr Ser Leu
1905                1910                1915                1920

Ser Asn Gly Gly Ala Ile Gln Asn Gln Glu Ser Gly Ile Lys Glu Ser
                1925                1930                1935

Val Ser Trp Gly Thr Gln Arg Thr Gln Asp Ala Pro His Glu Ala Arg
            1940                1945                1950

Pro Pro Leu Glu Arg Gly His Ser Thr Glu Ile Pro Val Gly Arg Ser
        1955                1960                1965

Gly Ala Leu Ala Val Asp Val Gln Met Gln Ser Ile Thr Arg Arg Gly
    1970                1975                1980

Pro Asp Gly Glu Pro Gln Pro Gly Leu Glu Ser Gln Gly Arg Ala Ala
1985                1990                1995                2000

Ser Met Pro Arg Leu Ala Ala Glu Thr Gln Pro Val Thr Asp Ala Ser
                2005                2010                2015

Pro Met Lys Arg Ser Ile Ser Thr Leu Ala Gln Arg Pro Arg Gly Thr
            2020                2025                2030

His Leu Cys Ser Thr Thr Pro Asp Arg Pro Pro Ser Gln Ala Ser
        2035                2040                2045

Ser His His His His Arg Cys His Arg Arg Asp Arg Lys Gln
    2050                2055                2060

Arg Ser Leu Glu Lys Gly Pro Ser Leu Ser Ala Asp Met Asp Gly Ala
2065                2070                2075                2080

Pro Ser Ser Ala Val Gly Pro Gly Leu Pro Pro Gly Glu Gly Pro Thr
                2085                2090                2095

Gly Cys Arg Arg Glu Arg Glu Arg Arg Gln Glu Arg Gly Arg Ser Gln
            2100                2105                2110

Glu Arg Arg Gln Pro Ser Ser Ser Ser Ser Glu Lys Gln Arg Phe Tyr
        2115                2120                2125

Ser Cys Asp Arg Phe Gly Gly Arg Glu Pro Pro Lys Pro Lys Pro Ser
    2130                2135                2140

Leu Ser Ser His Pro Thr Ser Pro Thr Ala Gly Gln Glu Pro Gly Pro
2145                2150                2155                2160

His Pro Gln Ala Gly Ser Ala Val Gly Phe Pro Asn Thr Thr Pro Cys
                2165                2170                2175

Cys Arg Glu Thr Pro Ser Ala Ser Pro Trp Pro Leu Ala Leu Glu Leu
            2180                2185                2190

Ala Leu Thr Leu Thr Trp Gly Ser Val Trp Thr Val Arg Pro Leu Ser
        2195                2200                2205

Thr Pro Cys Leu Arg Thr Arg Ser Leu Ser Arg Arg Leu Trp Pro Pro
    2210                2215                2220

Thr Arg Ala Ala Pro Pro Gly Leu Pro Thr Cys Pro Pro
2225                2230                2235
```

-continued

```
<210> SEQ ID NO 9
<211> LENGTH: 7011
<212> TYPE: DNA
<213> ORGANISM: Rattus norvegicus
<220> FEATURE:
<221> NAME/KEY: CDS
<222> LOCATION: 1..7008

<400> SEQUENCE: 9 atg gtc cgc ttc ggg gac gag cta ggc ggc cgc tat ggg ggc acc ggc      48
Met Val Arg Phe Gly Asp Glu Leu Gly Gly Arg Tyr Gly Gly Thr Gly
 1               5                  10                  15 ggc ggg gag cgg gct cgg ggc ggc ggg gcc ggc ggg gcc ggt ggc ccg      96
Gly Gly Glu Arg Ala Arg Gly Gly Gly Ala Gly Gly Ala Gly Gly Pro
             20                  25                  30 ggc cag ggg ggt ctg ccg ccg ggc cag cgg gtc ctg tac aag cag tcc     144
Gly Gln Gly Gly Leu Pro Pro Gly Gln Arg Val Leu Tyr Lys Gln Ser
         35                  40                  45 att gcg caa cgc gca cgg acc atg gcc ctg tac aac ccc atc cca gtc     192
Ile Ala Gln Arg Ala Arg Thr Met Ala Leu Tyr Asn Pro Ile Pro Val
 50                  55                  60 aag cag aac tgc ttc acc gtc aac cgc tcg ctc ttc gtc ttc agc gag     240
Lys Gln Asn Cys Phe Thr Val Asn Arg Ser Leu Phe Val Phe Ser Glu
 65                  70                  75                  80 gac aac gtc gtc cgc aaa tat gct aag cgc atc acc gaa tgg ccg ccc     288
Asp Asn Val Val Arg Lys Tyr Ala Lys Arg Ile Thr Glu Trp Pro Pro
                 85                  90                  95 ttc gaa tat atg atc ctg gcc acc atc atc gcc aac tgt att gtc ctg     336
Phe Glu Tyr Met Ile Leu Ala Thr Ile Ile Ala Asn Cys Ile Val Leu
            100                 105                 110 gcc ctg gag cag cac ctc cct gat ggg gac aag act ccc atg tct gaa     384
Ala Leu Glu Gln His Leu Pro Asp Gly Asp Lys Thr Pro Met Ser Glu
        115                 120                 125 cga ctg gat gac acg gaa cct tac ttc atc ggc atc ttt tgc ttc gag     432
Arg Leu Asp Asp Thr Glu Pro Tyr Phe Ile Gly Ile Phe Cys Phe Glu
    130                 135                 140 gcg ggc atc aag atc ata gct ctg ggc ttc gtg ttc cac aaa ggc tcc     480
Ala Gly Ile Lys Ile Ile Ala Leu Gly Phe Val Phe His Lys Gly Ser
145                 150                 155                 160 tac ctc cgg aat ggc tgg aac gtc atg gac ttc gtg gtg gtc ctc aca     528
Tyr Leu Arg Asn Gly Trp Asn Val Met Asp Phe Val Val Val Leu Thr
                165                 170                 175 gag att ctt gcc aca gct gga act gac ttt gat ctg cgc acc ctg agg     576
Glu Ile Leu Ala Thr Ala Gly Thr Asp Phe Asp Leu Arg Thr Leu Arg
            180                 185                 190 gct gtg cgt gtg ctt agg ccc ctg aag ttg gtg tct gga att cca agc     624
Ala Val Arg Val Leu Arg Pro Leu Lys Leu Val Ser Gly Ile Pro Ser
        195                 200                 205 ttg cag gtg gtg ctc aag tcc atc atg aag gcc atg gtc ccg ctg ctg     672
Leu Gln Val Val Leu Lys Ser Ile Met Lys Ala Met Val Pro Leu Leu
    210                 215                 220 cag atc ggg ctg ctc ctc ttc ttc gcc atc ctc atg ttc gct atc atc     720
Gln Ile Gly Leu Leu Leu Phe Phe Ala Ile Leu Met Phe Ala Ile Ile
225                 230                 235                 240 ggc ctc gag ttc tat atg ggc aaa ttc cat aag gcc tgc ttc ccc aac     768
Gly Leu Glu Phe Tyr Met Gly Lys Phe His Lys Ala Cys Phe Pro Asn
                245                 250                 255 agc aca gat gca gag cct gtg ggt gac ttt cct tgt ggc aag gag gcc     816
Ser Thr Asp Ala Glu Pro Val Gly Asp Phe Pro Cys Gly Lys Glu Ala
            260                 265                 270 cct gct cgt ctg tgt gac agt gac acc gaa tgc cgg gag tac tgg cca     864
```

```
Pro Ala Arg Leu Cys Asp Ser Asp Thr Glu Cys Arg Glu Tyr Trp Pro
        275                 280                 285 gga ccc aac ttt ggc atc acc aat ttt gac aac atc ctg ttt gcc atc      912
Gly Pro Asn Phe Gly Ile Thr Asn Phe Asp Asn Ile Leu Phe Ala Ile
    290                 295                 300 ttg acc gtg ttc cag tgt atc acc atg gag ggc tgg act gac atc ctc      960
Leu Thr Val Phe Gln Cys Ile Thr Met Glu Gly Trp Thr Asp Ile Leu
305                 310                 315                 320 tac aat aca aat gat gcg gcc ggc aac acg tgg aac tgg ttg tac ttc     1008
Tyr Asn Thr Asn Asp Ala Ala Gly Asn Thr Trp Asn Trp Leu Tyr Phe
                325                 330                 335 atc ccc ctc atc atc att ggc tcc ttc ttc atg ctc aac ctg gtg ctc     1056
Ile Pro Leu Ile Ile Ile Gly Ser Phe Phe Met Leu Asn Leu Val Leu
            340                 345                 350 ggt gtg ctt tca gga gag ttt gcc aaa gag cgg gag cga gtc gag aac     1104
Gly Val Leu Ser Gly Glu Phe Ala Lys Glu Arg Glu Arg Val Glu Asn
        355                 360                 365 cgc cgt gcc ttc ctg aag ctc cgc agg cag cag cag att gag cga gaa     1152
Arg Arg Ala Phe Leu Lys Leu Arg Arg Gln Gln Gln Ile Glu Arg Glu
    370                 375                 380 ctg aat ggg tac ttg gag tgg atc ttc aag gcg gag gaa gtc atg ttg     1200
Leu Asn Gly Tyr Leu Glu Trp Ile Phe Lys Ala Glu Glu Val Met Leu
385                 390                 395                 400 gca gag gag gac aag aac gca gaa gag aag tcc cct ttg gat gca gtg     1248
Ala Glu Glu Asp Lys Asn Ala Glu Glu Lys Ser Pro Leu Asp Ala Val
                405                 410                 415 ttg aag aga gct gct acc aag aag agc cga aat gac ctc atc cat gca     1296
Leu Lys Arg Ala Ala Thr Lys Lys Ser Arg Asn Asp Leu Ile His Ala
            420                 425                 430 gaa gag ggg gag gac cgg ttt gta gac ctc tgt gct gct ggg tct ccc     1344
Glu Glu Gly Glu Asp Arg Phe Val Asp Leu Cys Ala Ala Gly Ser Pro
        435                 440                 445 ttt gct cgt gcc agc ctc aag agt ggg aag aca gag agc tca tcg tac     1392
Phe Ala Arg Ala Ser Leu Lys Ser Gly Lys Thr Glu Ser Ser Ser Tyr
    450                 455                 460 ttc cgg agg aag gag aag atg ttc cgg ttc ctt atc cgt cgt atg gtg     1440
Phe Arg Arg Lys Glu Lys Met Phe Arg Phe Leu Ile Arg Arg Met Val
465                 470                 475                 480 aaa gca cag agc ttc tac tgg gtg gta ctg tgc gtg gtg gcc ctg aac     1488
Lys Ala Gln Ser Phe Tyr Trp Val Val Leu Cys Val Val Ala Leu Asn
                485                 490                 495 acg ttg tgt gtg gcc atg gta cac tat aat cag cct cag cgg ctt acc     1536
Thr Leu Cys Val Ala Met Val His Tyr Asn Gln Pro Gln Arg Leu Thr
            500                 505                 510 act gca ctg tac ttt gca gag ttt gtt ttc ctg ggt ctc ttc ctc aca     1584
Thr Ala Leu Tyr Phe Ala Glu Phe Val Phe Leu Gly Leu Phe Leu Thr
        515                 520                 525 gag atg tcc ctg aag atg tac ggt cta ggg ccc aga agc tac ttc cgg     1632
Glu Met Ser Leu Lys Met Tyr Gly Leu Gly Pro Arg Ser Tyr Phe Arg
    530                 535                 540 tct tcc ttc aac tgc ttt gac ttt ggg gtg att gtg ggg agt atc ttt     1680
Ser Ser Phe Asn Cys Phe Asp Phe Gly Val Ile Val Gly Ser Ile Phe
545                 550                 555                 560 gaa gta gtc tgg gct gcc atc aag cca gga acc tcc ttc gga atc agt     1728
Glu Val Val Trp Ala Ala Ile Lys Pro Gly Thr Ser Phe Gly Ile Ser
                565                 570                 575 gtg ctg cgg gct ctc cga ctg ctg agg att ttc aaa gtc acc aag tat     1776
Val Leu Arg Ala Leu Arg Leu Leu Arg Ile Phe Lys Val Thr Lys Tyr
            580                 585                 590
```

-continued

| | | |
|---|---|---|
| tgg aac tcc ctg agg aac ctg gtt gtt tcc ctc ctc aac tcc atg aag<br>Trp Asn Ser Leu Arg Asn Leu Val Val Ser Leu Leu Asn Ser Met Lys<br>595                          600                        605 | 1824 |
| tcc atc atc agc ctt ctc ttc ctg ctt ttc ctt ttc att gtg gtc ttc<br>Ser Ile Ile Ser Leu Leu Phe Leu Leu Phe Leu Phe Ile Val Val Phe<br>610                          615                        620 | 1872 |
| gct ctg ttg ggg atg cag ctg ttt ggg gga cag ttc aac ttt caa gat<br>Ala Leu Leu Gly Met Gln Leu Phe Gly Gly Gln Phe Asn Phe Gln Asp<br>625                          630                        635                        640 | 1920 |
| gag act cca acc acc aat ttt gat acc ttc cca gct gcc atc ctc act<br>Glu Thr Pro Thr Thr Asn Phe Asp Thr Phe Pro Ala Ala Ile Leu Thr<br>                          645                        650                        655 | 1968 |
| gtg ttt cag att ctg aca gga gag gac tgg aat gca gtc atg tat cat<br>Val Phe Gln Ile Leu Thr Gly Glu Asp Trp Asn Ala Val Met Tyr His<br>                        660                        665                        670 | 2016 |
| ggg att gag tca caa gga gga gtc agc aaa ggc atg ttt tca tcc ttt<br>Gly Ile Glu Ser Gln Gly Gly Val Ser Lys Gly Met Phe Ser Ser Phe<br>                  675                        680                        685 | 2064 |
| tac ttc atc gtc ctg aca ctg ttt gga aac tac acc ctg ttg aac gtt<br>Tyr Phe Ile Val Leu Thr Leu Phe Gly Asn Tyr Thr Leu Leu Asn Val<br>690                          695                        700 | 2112 |
| ttc ttg gcc att gct gtg gac aac ctt gcc aat gcc cag gag ttg acc<br>Phe Leu Ala Ile Ala Val Asp Asn Leu Ala Asn Ala Gln Glu Leu Thr<br>705                          710                        715                        720 | 2160 |
| aag gat gaa gag gag atg gaa gag gca gcc aat cag aag ctt gct ctt<br>Lys Asp Glu Glu Glu Met Glu Glu Ala Ala Asn Gln Lys Leu Ala Leu<br>                          725                        730                        735 | 2208 |
| cag aag gcc aaa gaa gta gct gaa gtc agc ccc atg tct gct gcc aac<br>Gln Lys Ala Lys Glu Val Ala Glu Val Ser Pro Met Ser Ala Ala Asn<br>                  740                        745                        750 | 2256 |
| atc tcc att gct gcc agg cag cag aac tcg gcc aag gcg cgc tca gta<br>Ile Ser Ile Ala Ala Arg Gln Gln Asn Ser Ala Lys Ala Arg Ser Val<br>755                          760                        765 | 2304 |
| tgg gag cag cgg gcc agt cag cta agg ctc cag aac ctg cgt gcc agc<br>Trp Glu Gln Arg Ala Ser Gln Leu Arg Leu Gln Asn Leu Arg Ala Ser<br>770                          775                        780 | 2352 |
| tgt gag gca ctg tac agt gag atg gac ccg gag gag cgc ctg cgt tat<br>Cys Glu Ala Leu Tyr Ser Glu Met Asp Pro Glu Glu Arg Leu Arg Tyr<br>785                          790                        795                        800 | 2400 |
| gcc agc acg cgc cac gtg agg cca gac atg aag aca cac atg gac cga<br>Ala Ser Thr Arg His Val Arg Pro Asp Met Lys Thr His Met Asp Arg<br>                  805                        810                        815 | 2448 |
| ccc cta gtg gtg gaa cct ggt cgg gat ggc ctg cgg gga ccc gcc ggg<br>Pro Leu Val Val Glu Pro Gly Arg Asp Gly Leu Arg Gly Pro Ala Gly<br>820                          825                        830 | 2496 |
| aac aag tca aag cct gag ggc acg gag gcc acc gaa ggt gcg gat cca<br>Asn Lys Ser Lys Pro Glu Gly Thr Glu Ala Thr Glu Gly Ala Asp Pro<br>                  835                        840                        845 | 2544 |
| cca cgc cga cac cac cgg cat cgt gat agg gac aag acc tca gcc tca<br>Pro Arg Arg His His Arg His Arg Asp Arg Asp Lys Thr Ser Ala Ser<br>850                          855                        860 | 2592 |
| acc cct gct gga ggc gaa cag gac agg aca gac tgc cca aag gcc gaa<br>Thr Pro Ala Gly Gly Glu Gln Asp Arg Thr Asp Cys Pro Lys Ala Glu<br>865                          870                        875                        880 | 2640 |
| agc acc gag acc ggg gcc cgg gag gaa cgt gcg cgc cct cgt cga agt<br>Ser Thr Glu Thr Gly Ala Arg Glu Glu Arg Ala Arg Pro Arg Arg Ser<br>                  885                        890                        895 | 2688 |
| cac agc aag gag gct cca ggg gct gac aca caa gtg cgt tgt gag cgc<br>His Ser Lys Glu Ala Pro Gly Ala Asp Thr Gln Val Arg Cys Glu Arg<br>900                          905                        910 | 2736 |

```
agt aga cgt cac cac cgg cgc gga tcc ccg gag gag gcc act gaa cgg      2784
Ser Arg Arg His His Arg Arg Gly Ser Pro Glu Glu Ala Thr Glu Arg
            915                 920                 925 gaa cct cgg cgc cac cgt gcc cac cgg cac gca cag gac tca agc aag      2832
Glu Pro Arg Arg His Arg Ala His Arg His Ala Gln Asp Ser Ser Lys
        930                 935                 940 gaa ggc aag gag ggc act gca ccg gtg ctt gta ccc aag ggc gag cgt      2880
Glu Gly Lys Glu Gly Thr Ala Pro Val Leu Val Pro Lys Gly Glu Arg
945                 950                 955                 960 cgc gca aga cat cga ggc ccg cgt acg ggc ccc cgt gag aca gag aac      2928
Arg Ala Arg His Arg Gly Pro Arg Thr Gly Pro Arg Glu Thr Glu Asn
                965                 970                 975 agt gag gag ccc aca cgc agg cac cgt gca aag cat aag gtg cca cca      2976
Ser Glu Glu Pro Thr Arg Arg His Arg Ala Lys His Lys Val Pro Pro
            980                 985                 990 aca ctt gag ccc cca gag agg gag gtt gca gag aag gag agc aac gtg      3024
Thr Leu Glu Pro Pro Glu Arg Glu Val Ala Glu Lys Glu Ser Asn Val
        995                 1000                1005 gtg gaa ggg gat aag gaa act cga aat cac cag ccc aag gaa cct cgc      3072
Val Glu Gly Asp Lys Glu Thr Arg Asn His Gln Pro Lys Glu Pro Arg
    1010                1015                1020 tgt gac ctg gag gcc att gcg gtt aca ggc gtg ggc tct ctg cac atg      3120
Cys Asp Leu Glu Ala Ile Ala Val Thr Gly Val Gly Ser Leu His Met
1025                1030                1035                1040 ctg ccc agc acc tgt ctc cag aaa gtg gac gaa cag cca gag gat gca      3168
Leu Pro Ser Thr Cys Leu Gln Lys Val Asp Glu Gln Pro Glu Asp Ala
                1045                1050                1055 gac aac cag cgt aat gtc acc cgg atg ggc agt cag ccc tca gac ccc      3216
Asp Asn Gln Arg Asn Val Thr Arg Met Gly Ser Gln Pro Ser Asp Pro
            1060                1065                1070 agc acc act gtg cat gtc cca gtg aca ctg aca ggc cct ccc ggg gag      3264
Ser Thr Thr Val His Val Pro Val Thr Leu Thr Gly Pro Pro Gly Glu
        1075                1080                1085 gcc act gta gtt ccc agt gct aac acg gac ctg gaa ggc caa gcg gag      3312
Ala Thr Val Val Pro Ser Ala Asn Thr Asp Leu Glu Gly Gln Ala Glu
    1090                1095                1100 ggc aag aag gag gca gag gct gac gat gtg ctg aga aga ggc ccc agg      3360
Gly Lys Lys Glu Ala Glu Ala Asp Asp Val Leu Arg Arg Gly Pro Arg
1105                1110                1115                1120 ccc atc gtt ccc tac agt tcc atg ttc tgc ctc agc ccc acc aac cta      3408
Pro Ile Val Pro Tyr Ser Ser Met Phe Cys Leu Ser Pro Thr Asn Leu
                1125                1130                1135 ctc cgt cgc ttc tgc cat tac att gtg acc atg cgg tac ttt gag atg      3456
Leu Arg Arg Phe Cys His Tyr Ile Val Thr Met Arg Tyr Phe Glu Met
            1140                1145                1150 gtg att ctt gtg gtc atc gcc ttg agc agc att gcc ctg gct gct gag      3504
Val Ile Leu Val Val Ile Ala Leu Ser Ser Ile Ala Leu Ala Ala Glu
        1155                1160                1165 gat ccc gtg cgg acc gac tca ttc cgg aac aat gct ctg aag tac atg      3552
Asp Pro Val Arg Thr Asp Ser Phe Arg Asn Asn Ala Leu Lys Tyr Met
    1170                1175                1180 gac tac atc ttt aca gga gtc ttc acc ttt gag atg gtc ata aag atg      3600
Asp Tyr Ile Phe Thr Gly Val Phe Thr Phe Glu Met Val Ile Lys Met
1185                1190                1195                1200 ata gac ttg ggc ctg ctg ctg cac cct ggg gcc tac ttc cgg gac ctg      3648
Ile Asp Leu Gly Leu Leu Leu His Pro Gly Ala Tyr Phe Arg Asp Leu
                1205                1210                1215 tgg aac att ctg gac ttc att gtt gtc agt gga gcc ctg gtg gca ttt      3696
Trp Asn Ile Leu Asp Phe Ile Val Val Ser Gly Ala Leu Val Ala Phe
```

-continued

| | | |
|---|---|---|
| gca ttc tcg agc ttc atg gga gga tcc aaa ggg aaa gac atc aat acc<br>Ala Phe Ser Ser Phe Met Gly Gly Ser Lys Gly Lys Asp Ile Asn Thr<br>        1235                        1240                  1245 | 3744 |
| atc aag tct ctg aga gtc ctg cga gtc ctg cgg ccc ctc aag acc atc<br>Ile Lys Ser Leu Arg Val Leu Arg Val Leu Arg Pro Leu Lys Thr Ile<br>1250                  1255                    1260 | 3792 |
| aag cgg ctg cct aaa ctc aag gct gtg ttt gac tgt gtg gtg aac tct<br>Lys Arg Leu Pro Lys Leu Lys Ala Val Phe Asp Cys Val Val Asn Ser<br>1265                  1270                  1275                1280 | 3840 |
| ctg aag aat gtc ttg aac atc ctg atc gtc tac atg ctc ttc atg ttt<br>Leu Lys Asn Val Leu Asn Ile Leu Ile Val Tyr Met Leu Phe Met Phe<br>                        1285                  1290                1295 | 3888 |
| ata ttt gcc gtc atc gcc gtc caa ctc ttc aaa ggg aag ttc ttt tac<br>Ile Phe Ala Val Ile Ala Val Gln Leu Phe Lys Gly Lys Phe Phe Tyr<br>            1300                  1305                1310 | 3936 |
| tgc act gat gag tcc aag gag ctg gag cgg gac tgc agg ggt cag tat<br>Cys Thr Asp Glu Ser Lys Glu Leu Glu Arg Asp Cys Arg Gly Gln Tyr<br>1315                  1320                  1325 | 3984 |
| ttg gat tat gag aag gaa gag gta gaa gcc cag cca agg cag tgg aag<br>Leu Asp Tyr Glu Lys Glu Glu Val Glu Ala Gln Pro Arg Gln Trp Lys<br>        1330                  1335                1340 | 4032 |
| aaa tat gac ttc cac tat gac aat gtg ctc tgg gcc ttg ctg act ctg<br>Lys Tyr Asp Phe His Tyr Asp Asn Val Leu Trp Ala Leu Leu Thr Leu<br>1345                  1350                  1355                1360 | 4080 |
| ttt acg gtg tcc aca gga gag ggg tgg ccc atg gtg ctg aaa cac tct<br>Phe Thr Val Ser Thr Gly Glu Gly Trp Pro Met Val Leu Lys His Ser<br>                        1365                  1370                1375 | 4128 |
| gtg gac gcc acc tat gag gag cag ggg cca agc ccc ggg ttt cgg atg<br>Val Asp Ala Thr Tyr Glu Glu Gln Gly Pro Ser Pro Gly Phe Arg Met<br>        1380                  1385                1390 | 4176 |
| gag ctt tcc atc ttc tat gtg gtc tac ttt gtg gtc ttc cct ttt ttc<br>Glu Leu Ser Ile Phe Tyr Val Val Tyr Phe Val Val Phe Pro Phe Phe<br>            1395                  1400                1405 | 4224 |
| ttt gtc aac atc ttt gtg gcc ttg atc atc atc acc ttc cag gag cag<br>Phe Val Asn Ile Phe Val Ala Leu Ile Ile Ile Thr Phe Gln Glu Gln<br>        1410                  1415                1420 | 4272 |
| ggg gac aag gtg atg tct gag tgc agt ctg gaa aag aat gag agg gct<br>Gly Asp Lys Val Met Ser Glu Cys Ser Leu Glu Lys Asn Glu Arg Ala<br>1425                  1430                  1435                1440 | 4320 |
| tgc att gac ttt gcc atc agc gcc aaa ccc ctg aca cgg tac atg cct<br>Cys Ile Asp Phe Ala Ile Ser Ala Lys Pro Leu Thr Arg Tyr Met Pro<br>                        1445                  1450                1455 | 4368 |
| cag aac aag cag tcg ttc cag tat aag aca tgg aca ttt gtg gtc tct<br>Gln Asn Lys Gln Ser Phe Gln Tyr Lys Thr Trp Thr Phe Val Val Ser<br>        1460                  1465                1470 | 4416 |
| cca ccc ttt gag tac ttc att atg gcc atg ata gcc ctc aac aca gtg<br>Pro Pro Phe Glu Tyr Phe Ile Met Ala Met Ile Ala Leu Asn Thr Val<br>            1475                  1480                1485 | 4464 |
| gtg ctg atg atg aag ttc tac gat gcc cct tat gag tac gag ctg atg<br>Val Leu Met Met Lys Phe Tyr Asp Ala Pro Tyr Glu Tyr Glu Leu Met<br>        1490                  1495                1500 | 4512 |
| ctg aag tgc ttg aac atc gtc ttc aca tcc atg ttc tct ctg gag tgc<br>Leu Lys Cys Leu Asn Ile Val Phe Thr Ser Met Phe Ser Leu Glu Cys<br>1505                  1510                  1515                1520 | 4560 |
| atc ctg aag atc atc gcc ttc ggg gtg ttg aac tac ttc aga gat gcc<br>Ile Leu Lys Ile Ile Ala Phe Gly Val Leu Asn Tyr Phe Arg Asp Ala<br>                        1525                  1530                1535 | 4608 |
| tgg aac gtc ttt gac ttt gtc act gtt ttg gga agt att act gat att | 4656 |

```
Trp Asn Val Phe Asp Phe Val Thr Val Leu Gly Ser Ile Thr Asp Ile
        1540                1545                1550 tta gta acg gag att gcg aac aac ttc atc aac ttg agc ttc ctt cgc    4704
Leu Val Thr Glu Ile Ala Asn Asn Phe Ile Asn Leu Ser Phe Leu Arg
    1555                1560                1565 ctc ttc cgg gca gca cgg ctg atc aag ctc tgt cgc cag ggc tac acc    4752
Leu Phe Arg Ala Ala Arg Leu Ile Lys Leu Cys Arg Gln Gly Tyr Thr
1570                1575                1580 atc cgc atc ttg tta tgg acc ttt gtc cag tcc ttt aag gcg ctg ccc    4800
Ile Arg Ile Leu Leu Trp Thr Phe Val Gln Ser Phe Lys Ala Leu Pro
1585                1590                1595                1600 tac gtg tgc ctc ctc att gcc atg ctg ttc ttc atc tac gcc atc atc    4848
Tyr Val Cys Leu Leu Ile Ala Met Leu Phe Phe Ile Tyr Ala Ile Ile
                1605                1610                1615 ggc atg cag gtt ttt gga aac att gcc ctt gat gat ggc acc agc atc    4896
Gly Met Gln Val Phe Gly Asn Ile Ala Leu Asp Asp Gly Thr Ser Ile
            1620                1625                1630 aac cga cac aac aac ttc cgg aca ttt ctg caa gcc tta atg ctg ttg    4944
Asn Arg His Asn Asn Phe Arg Thr Phe Leu Gln Ala Leu Met Leu Leu
        1635                1640                1645 ttc agg agt gcc act ggg gag gcc tgg cac gaa atc atg ctg tct tgc    4992
Phe Arg Ser Ala Thr Gly Glu Ala Trp His Glu Ile Met Leu Ser Cys
    1650                1655                1660 ctg ggc aac cgg gcc tgc gac cca cat gcc aac gcc agc gaa tgc ggg    5040
Leu Gly Asn Arg Ala Cys Asp Pro His Ala Asn Ala Ser Glu Cys Gly
1665                1670                1675                1680 agc gac ttt gcc tat ttt tat ttt gtc tcc ttc atc ttc ctc tgt tcc    5088
Ser Asp Phe Ala Tyr Phe Tyr Phe Val Ser Phe Ile Phe Leu Cys Ser
                1685                1690                1695 ttt ctg atg ctg aac ctc ttt gtt gct gtg atc atg gac aat ttc gaa    5136
Phe Leu Met Leu Asn Leu Phe Val Ala Val Ile Met Asp Asn Phe Glu
            1700                1705                1710 tac ctc acg cgg gat tct tcc atc cta ggg ccg cac cac ctc gat gaa    5184
Tyr Leu Thr Arg Asp Ser Ser Ile Leu Gly Pro His His Leu Asp Glu
        1715                1720                1725 ttc att cgc gtc tgg gct gaa tac gac cca gct gcg tgt ggg cgc atc    5232
Phe Ile Arg Val Trp Ala Glu Tyr Asp Pro Ala Ala Cys Gly Arg Ile
    1730                1735                1740 agt tac aat gac atg ttt gag atg ctg aaa cac atg tcc cca cct ctg    5280
Ser Tyr Asn Asp Met Phe Glu Met Leu Lys His Met Ser Pro Pro Leu
1745                1750                1755                1760 ggt ttg ggg aag aaa tgc ccg gct cga gtt gca tac aag cgc ctg gtt    5328
Gly Leu Gly Lys Lys Cys Pro Ala Arg Val Ala Tyr Lys Arg Leu Val
                1765                1770                1775 cga atg aac atg ccc ata tcc aat gag gac atg acg gta cac ttt aca    5376
Arg Met Asn Met Pro Ile Ser Asn Glu Asp Met Thr Val His Phe Thr
            1780                1785                1790 tcc aca ctg atg gcc ctc atc cgg acg gca ctg gag atc aag ctt gcc    5424
Ser Thr Leu Met Ala Leu Ile Arg Thr Ala Leu Glu Ile Lys Leu Ala
        1795                1800                1805 cca gcg ggg aca aaa cag cac caa tgt gat gct gag ctg agg aag gag    5472
Pro Ala Gly Thr Lys Gln His Gln Cys Asp Ala Glu Leu Arg Lys Glu
    1810                1815                1820 atc tct tct gtg tgg gct aat ctg ccc cag aag act ctg gac tta ctg    5520
Ile Ser Ser Val Trp Ala Asn Leu Pro Gln Lys Thr Leu Asp Leu Leu
1825                1830                1835                1840 gtg cca ccc cac aaa cct gac gag atg aca gtg ggg aag gtc tat gcg    5568
Val Pro Pro His Lys Pro Asp Glu Met Thr Val Gly Lys Val Tyr Ala
                1845                1850                1855
```

-continued

```
gct ctc atg ata ttt gac ttc tac aaa cag aac aaa acc acc aga gat      5616
Ala Leu Met Ile Phe Asp Phe Tyr Lys Gln Asn Lys Thr Thr Arg Asp
        1860                1865                1870 cag act cac caa gct cct gga ggc ctg tcc cag atg ggt cct gtt tcc      5664
Gln Thr His Gln Ala Pro Gly Gly Leu Ser Gln Met Gly Pro Val Ser
        1875                1880                1885 cta ttc cat cct ctg aag gcc acc ctg gag cag aca cag ccc gct gtg      5712
Leu Phe His Pro Leu Lys Ala Thr Leu Glu Gln Thr Gln Pro Ala Val
        1890                1895                1900 ctc cga gga gct cgg gtt ttc ctt cga caa aag agt gca act tcc ctc      5760
Leu Arg Gly Ala Arg Val Phe Leu Arg Gln Lys Ser Ala Thr Ser Leu
1905                1910                1915                1920 agc aat ggg ggc gcc ata caa acc cag gaa agt ggc atc aag gag tcc      5808
Ser Asn Gly Gly Ala Ile Gln Thr Gln Glu Ser Gly Ile Lys Glu Ser
        1925                1930                1935 ctg tcc tgg ggc acg cag agg acc cag gac gta ctt tat gag gcc aga      5856
Leu Ser Trp Gly Thr Gln Arg Thr Gln Asp Val Leu Tyr Glu Ala Arg
        1940                1945                1950 gca cct cta gaa cgt ggc cat tct gca gag atc cct gtg ggg cag cca      5904
Ala Pro Leu Glu Arg Gly His Ser Ala Glu Ile Pro Val Gly Gln Pro
        1955                1960                1965 gga gca ctg gct gta gat gtc cag atg cag aac atg aca ttg aga gga      5952
Gly Ala Leu Ala Val Asp Val Gln Met Gln Asn Met Thr Leu Arg Gly
        1970                1975                1980 ccg gat ggg gag ccc cag cct ggc ctg gag agc caa ggc cga gcg gcc      6000
Pro Asp Gly Glu Pro Gln Pro Gly Leu Glu Ser Gln Gly Arg Ala Ala
1985                1990                1995                2000 tct atg cca cgc ctg gcg gca gaa aca cag ccg gcc cct aat gcc agc      6048
Ser Met Pro Arg Leu Ala Ala Glu Thr Gln Pro Ala Pro Asn Ala Ser
        2005                2010                2015 ccc atg aag cgc tcc atc tcc aca ctg gct cca cgc ccg cat ggg act      6096
Pro Met Lys Arg Ser Ile Ser Thr Leu Ala Pro Arg Pro His Gly Thr
        2020                2025                2030 cag ctt tgc aac aca gtc ctg gac cgg cca cct cct agc cag gtg tcc      6144
Gln Leu Cys Asn Thr Val Leu Asp Arg Pro Pro Pro Ser Gln Val Ser
        2035                2040                2045 cat cac cac cac cac cgc tgc cac cgg cgc agg gac aag aag cag agg      6192
His His His His His Arg Cys His Arg Arg Arg Asp Lys Lys Gln Arg
        2050                2055                2060 tcc ctg gaa aag ggg ccc agc ctg tct gtt gac aca gaa ggt gca cca      6240
Ser Leu Glu Lys Gly Pro Ser Leu Ser Val Asp Thr Glu Gly Ala Pro
2065                2070                2075                2080 agt act gct gca gga tct ggc ctg ccc cat gga gaa ggg tcc aca ggc      6288
Ser Thr Ala Ala Gly Ser Gly Leu Pro His Gly Glu Gly Ser Thr Gly
        2085                2090                2095 tgc cgg cgg gag cgt aag caa gag cga ggc cgg tcc cag gag cgg agg      6336
Cys Arg Arg Glu Arg Lys Gln Glu Arg Gly Arg Ser Gln Glu Arg Arg
        2100                2105                2110 cag ccc tcc tcc tct tct tca gag aag cag cgc ttc tat tcc tgt gac      6384
Gln Pro Ser Ser Ser Ser Ser Glu Lys Gln Arg Phe Tyr Ser Cys Asp
        2115                2120                2125 cgc ttt ggg agc cgg gag ccc cca caa cct aag ccc tcc ctc agt agc      6432
Arg Phe Gly Ser Arg Glu Pro Pro Gln Pro Lys Pro Ser Leu Ser Ser
        2130                2135                2140 cac ccc ata tcg cca aca gcg gca cta gag cca gga ccc cac ccg cag      6480
His Pro Ile Ser Pro Thr Ala Ala Leu Glu Pro Gly Pro His Pro Gln
        2145                2150                2155                2160 ggc agt ggt tcc gtt aat ggg agc ccc ttg atg tca aca tct ggt gct      6528
Gly Ser Gly Ser Val Asn Gly Ser Pro Leu Met Ser Thr Ser Gly Ala
        2165                2170                2175
```

-continued

```
agc acg ccg ggc cga ggt ggg cgg agg cag ctc ccc cag act ccc ctg      6576
Ser Thr Pro Gly Arg Gly Gly Arg Arg Gln Leu Pro Gln Thr Pro Leu
        2180                2185                2190 acc cca cgc ccc agc atc acc tac aag acg gcc aat tcc tcg cct gtc      6624
Thr Pro Arg Pro Ser Ile Thr Tyr Lys Thr Ala Asn Ser Ser Pro Val
    2195                2200                2205 cac ttt gct gag ggt cag agt ggc ctt cca gcc ttc tcc cct ggc cgt      6672
His Phe Ala Glu Gly Gln Ser Gly Leu Pro Ala Phe Ser Pro Gly Arg
    2210                2215                2220 ctc agc cgc ggc ctt tct gaa cac aat gcc ctg ctc cag aaa gag ccc      6720
Leu Ser Arg Gly Leu Ser Glu His Asn Ala Leu Leu Gln Lys Glu Pro
2225                2230                2235                2240 ctg agc cag cct cta gct tct ggc tcc cgc att ggc tct gac cct tac      6768
Leu Ser Gln Pro Leu Ala Ser Gly Ser Arg Ile Gly Ser Asp Pro Tyr
        2245                2250                2255 cta ggg cag cgt ctg gac agt gag gcc tct gcc cac aac ctg cct gag      6816
Leu Gly Gln Arg Leu Asp Ser Glu Ala Ser Ala His Asn Leu Pro Glu
        2260                2265                2270 gat aca ctc acc ttt gaa gag gcc gtg gcc acc aac tct ggc cgc tcc      6864
Asp Thr Leu Thr Phe Glu Glu Ala Val Ala Thr Asn Ser Gly Arg Ser
        2275                2280                2285 tcc agg act tcc tat gtg tcc tcc ctc act tcc caa tcc cac cct ctc      6912
Ser Arg Thr Ser Tyr Val Ser Ser Leu Thr Ser Gln Ser His Pro Leu
        2290                2295                2300 cgc cgt gta ccc aat ggc tac cac tgc act ttg gga ctc agc acc ggc      6960
Arg Arg Val Pro Asn Gly Tyr His Cys Thr Leu Gly Leu Ser Thr Gly
2305                2310                2315                2320 gtc cgg gcg cgg cac agc tac cac cac cca gac cag gat cac tgg tgc t   7009
Val Arg Ala Arg His Ser Tyr His His Pro Asp Gln Asp His Trp Cys
        2325                2330                2335 ag                                                                   7011

<210> SEQ ID NO 10
<211> LENGTH: 2336
<212> TYPE: PRT
<213> ORGANISM: Rattus norvegicus

<400> SEQUENCE: 10

Met Val Arg Phe Gly Asp Glu Leu Gly Gly Arg Tyr Gly Gly Thr Gly
 1               5                   10                  15

Gly Gly Glu Arg Ala Arg Gly Gly Ala Gly Gly Ala Gly Gly Pro
            20                  25                  30

Gly Gln Gly Gly Leu Pro Pro Gly Gln Arg Val Leu Tyr Lys Gln Ser
        35                  40                  45

Ile Ala Gln Arg Ala Arg Thr Met Ala Leu Tyr Asn Pro Ile Pro Val
    50                  55                  60

Lys Gln Asn Cys Phe Thr Val Asn Arg Ser Leu Phe Val Phe Ser Glu
65                  70                  75                  80

Asp Asn Val Val Arg Lys Tyr Ala Lys Arg Ile Thr Glu Trp Pro Pro
                85                  90                  95

Phe Glu Tyr Met Ile Leu Ala Thr Ile Ile Ala Asn Cys Ile Val Leu
            100                 105                 110

Ala Leu Glu Gln His Leu Pro Asp Gly Asp Lys Thr Pro Met Ser Glu
        115                 120                 125

Arg Leu Asp Asp Thr Glu Pro Tyr Phe Ile Gly Ile Phe Cys Phe Glu
    130                 135                 140

Ala Gly Ile Lys Ile Ile Ala Leu Gly Phe Val Phe His Lys Gly Ser
```

```
                145                 150                 155                 160
Tyr Leu Arg Asn Gly Trp Asn Val Met Asp Phe Val Val Leu Thr
                165                 170                 175
Glu Ile Leu Ala Thr Ala Gly Thr Asp Phe Asp Leu Arg Thr Leu Arg
                180                 185                 190
Ala Val Arg Val Leu Arg Pro Leu Lys Leu Val Ser Gly Ile Pro Ser
            195                 200                 205
Leu Gln Val Val Leu Lys Ser Ile Met Lys Ala Met Val Pro Leu Leu
        210                 215                 220
Gln Ile Gly Leu Leu Leu Phe Phe Ala Ile Leu Met Phe Ala Ile Ile
225                 230                 235                 240
Gly Leu Glu Phe Tyr Met Gly Lys Phe His Lys Ala Cys Phe Pro Asn
                245                 250                 255
Ser Thr Asp Ala Glu Pro Val Gly Asp Phe Pro Cys Gly Lys Glu Ala
            260                 265                 270
Pro Ala Arg Leu Cys Asp Ser Asp Thr Glu Cys Arg Glu Tyr Trp Pro
        275                 280                 285
Gly Pro Asn Phe Gly Ile Thr Asn Phe Asp Asn Ile Leu Phe Ala Ile
    290                 295                 300
Leu Thr Val Phe Gln Cys Ile Thr Met Glu Gly Trp Thr Asp Ile Leu
305                 310                 315                 320
Tyr Asn Thr Asn Asp Ala Ala Gly Asn Thr Trp Asn Trp Leu Tyr Phe
                325                 330                 335
Ile Pro Leu Ile Ile Ile Gly Ser Phe Phe Met Leu Asn Leu Val Leu
            340                 345                 350
Gly Val Leu Ser Gly Glu Phe Ala Lys Glu Arg Glu Arg Val Glu Asn
        355                 360                 365
Arg Arg Ala Phe Leu Lys Leu Arg Arg Gln Gln Gln Ile Glu Arg Glu
    370                 375                 380
Leu Asn Gly Tyr Leu Glu Trp Ile Phe Lys Ala Glu Glu Val Met Leu
385                 390                 395                 400
Ala Glu Glu Asp Lys Asn Ala Glu Glu Lys Ser Pro Leu Asp Ala Val
                405                 410                 415
Leu Lys Arg Ala Ala Thr Lys Lys Ser Arg Asn Asp Leu Ile His Ala
            420                 425                 430
Glu Glu Gly Glu Asp Arg Phe Val Asp Leu Cys Ala Ala Gly Ser Pro
        435                 440                 445
Phe Ala Arg Ala Ser Leu Lys Ser Gly Lys Thr Glu Ser Ser Ser Tyr
    450                 455                 460
Phe Arg Arg Lys Glu Lys Met Phe Arg Phe Leu Ile Arg Arg Met Val
465                 470                 475                 480
Lys Ala Gln Ser Phe Tyr Trp Val Val Leu Cys Val Val Ala Leu Asn
                485                 490                 495
Thr Leu Cys Val Ala Met Val His Tyr Asn Gln Pro Gln Arg Leu Thr
            500                 505                 510
Thr Ala Leu Tyr Phe Ala Glu Phe Val Phe Leu Gly Leu Phe Leu Thr
        515                 520                 525
Glu Met Ser Leu Lys Met Tyr Gly Leu Gly Pro Arg Ser Tyr Phe Arg
    530                 535                 540
Ser Ser Phe Asn Cys Phe Asp Phe Gly Val Ile Val Gly Ser Ile Phe
545                 550                 555                 560
Glu Val Val Trp Ala Ala Ile Lys Pro Gly Thr Ser Phe Gly Ile Ser
                565                 570                 575
```

```
Val Leu Arg Ala Leu Arg Leu Arg Ile Phe Lys Val Thr Lys Tyr
            580                 585                 590

Trp Asn Ser Leu Arg Asn Leu Val Val Ser Leu Leu Asn Ser Met Lys
            595                 600                 605

Ser Ile Ile Ser Leu Leu Phe Leu Leu Phe Leu Phe Ile Val Val Phe
            610                 615                 620

Ala Leu Leu Gly Met Gln Leu Phe Gly Gly Gln Phe Asn Phe Gln Asp
625                 630                 635                 640

Glu Thr Pro Thr Thr Asn Phe Asp Thr Phe Pro Ala Ala Ile Leu Thr
                    645                 650                 655

Val Phe Gln Ile Leu Thr Gly Glu Asp Trp Asn Ala Val Met Tyr His
            660                 665                 670

Gly Ile Glu Ser Gln Gly Gly Val Ser Lys Gly Met Phe Ser Ser Phe
            675                 680                 685

Tyr Phe Ile Val Leu Thr Leu Phe Gly Asn Tyr Thr Leu Leu Asn Val
            690                 695                 700

Phe Leu Ala Ile Ala Val Asp Asn Leu Ala Asn Ala Gln Glu Leu Thr
705                 710                 715                 720

Lys Asp Glu Glu Glu Met Glu Glu Ala Ala Asn Gln Lys Leu Ala Leu
                    725                 730                 735

Gln Lys Ala Lys Glu Val Ala Glu Val Ser Pro Met Ser Ala Ala Asn
            740                 745                 750

Ile Ser Ile Ala Ala Arg Gln Gln Asn Ser Ala Lys Ala Arg Ser Val
            755                 760                 765

Trp Glu Gln Arg Ala Ser Gln Leu Arg Leu Gln Asn Leu Arg Ala Ser
770                 775                 780

Cys Glu Ala Leu Tyr Ser Glu Met Asp Pro Glu Glu Arg Leu Arg Tyr
785                 790                 795                 800

Ala Ser Thr Arg His Val Arg Pro Asp Met Lys Thr His Met Asp Arg
            805                 810                 815

Pro Leu Val Val Glu Pro Gly Arg Asp Gly Leu Arg Gly Pro Ala Gly
            820                 825                 830

Asn Lys Ser Lys Pro Glu Gly Thr Glu Ala Thr Glu Gly Ala Asp Pro
            835                 840                 845

Pro Arg Arg His His Arg His Arg Asp Arg Asp Lys Thr Ser Ala Ser
850                 855                 860

Thr Pro Ala Gly Gly Glu Gln Asp Arg Thr Asp Cys Pro Lys Ala Glu
865                 870                 875                 880

Ser Thr Glu Thr Gly Ala Arg Glu Arg Ala Arg Pro Arg Arg Ser
            885                 890                 895

His Ser Lys Glu Ala Pro Gly Ala Asp Thr Gln Val Arg Cys Glu Arg
            900                 905                 910

Ser Arg Arg His His Arg Arg Gly Ser Pro Glu Glu Ala Thr Glu Arg
            915                 920                 925

Glu Pro Arg Arg His Arg Ala His Ala Gln Asp Ser Ser Lys
            930                 935                 940

Glu Gly Lys Glu Gly Thr Ala Pro Val Leu Val Pro Lys Gly Glu Arg
945                 950                 955                 960

Arg Ala Arg His Arg Gly Pro Arg Thr Gly Pro Arg Glu Thr Glu Asn
                    965                 970                 975

Ser Glu Glu Pro Thr Arg Arg His Arg Ala Lys His Lys Val Pro Pro
            980                 985                 990
```

```
Thr Leu Glu Pro Pro Glu Arg Glu Val Ala Glu Lys Glu Ser Asn Val
        995                1000                1005

Val Glu Gly Asp Lys Glu Thr Arg Asn His Gln Pro Lys Glu Pro Arg
   1010                1015                1020

Cys Asp Leu Glu Ala Ile Ala Val Thr Gly Val Gly Ser Leu His Met
1025                1030                1035                1040

Leu Pro Ser Thr Cys Leu Gln Lys Val Asp Glu Gln Pro Glu Asp Ala
            1045                1050                1055

Asp Asn Gln Arg Asn Val Thr Arg Met Gly Ser Gln Pro Ser Asp Pro
        1060                1065                1070

Ser Thr Thr Val His Val Pro Val Thr Leu Thr Gly Pro Pro Gly Glu
        1075                1080                1085

Ala Thr Val Val Pro Ser Ala Asn Thr Asp Leu Glu Gly Gln Ala Glu
        1090                1095                1100

Gly Lys Lys Glu Ala Glu Ala Asp Asp Val Leu Arg Arg Gly Pro Arg
1105                1110                1115                1120

Pro Ile Val Pro Tyr Ser Ser Met Phe Cys Leu Ser Pro Thr Asn Leu
            1125                1130                1135

Leu Arg Arg Phe Cys His Tyr Ile Val Thr Met Arg Tyr Phe Glu Met
            1140                1145                1150

Val Ile Leu Val Val Ile Ala Leu Ser Ser Ile Ala Leu Ala Ala Glu
        1155                1160                1165

Asp Pro Val Arg Thr Asp Ser Phe Arg Asn Asn Ala Leu Lys Tyr Met
    1170                1175                1180

Asp Tyr Ile Phe Thr Gly Val Phe Thr Phe Glu Met Val Ile Lys Met
1185                1190                1195                1200

Ile Asp Leu Gly Leu Leu Leu His Pro Gly Ala Tyr Phe Arg Asp Leu
        1205                1210                1215

Trp Asn Ile Leu Asp Phe Ile Val Val Ser Gly Ala Leu Val Ala Phe
        1220                1225                1230

Ala Phe Ser Ser Phe Met Gly Gly Ser Lys Gly Lys Asp Ile Asn Thr
        1235                1240                1245

Ile Lys Ser Leu Arg Val Leu Arg Val Leu Arg Pro Leu Lys Thr Ile
        1250                1255                1260

Lys Arg Leu Pro Lys Leu Lys Ala Val Phe Asp Cys Val Val Asn Ser
1265                1270                1275                1280

Leu Lys Asn Val Leu Asn Ile Leu Ile Val Tyr Met Leu Phe Met Phe
            1285                1290                1295

Ile Phe Ala Val Ile Ala Val Gln Leu Phe Lys Gly Lys Phe Phe Tyr
        1300                1305                1310

Cys Thr Asp Glu Ser Lys Glu Leu Glu Arg Asp Cys Arg Gly Gln Tyr
        1315                1320                1325

Leu Asp Tyr Glu Lys Glu Glu Val Glu Ala Gln Pro Arg Gln Trp Lys
    1330                1335                1340

Lys Tyr Asp Phe His Tyr Asp Asn Val Leu Trp Ala Leu Leu Thr Leu
1345                1350                1355                1360

Phe Thr Val Ser Thr Gly Glu Gly Trp Pro Met Val Leu Lys His Ser
            1365                1370                1375

Val Asp Ala Thr Tyr Glu Glu Gln Gly Pro Ser Pro Gly Phe Arg Met
            1380                1385                1390

Glu Leu Ser Ile Phe Tyr Val Val Tyr Phe Val Val Phe Pro Phe Phe
        1395                1400                1405

Phe Val Asn Ile Phe Val Ala Leu Ile Ile Ile Thr Phe Gln Glu Gln
```

-continued

```
            1410                1415                1420
Gly Asp Lys Val Met Ser Glu Cys Ser Leu Glu Lys Asn Glu Arg Ala
1425                1430                1435                1440
Cys Ile Asp Phe Ala Ile Ser Ala Lys Pro Leu Thr Arg Tyr Met Pro
                1445                1450                1455
Gln Asn Lys Gln Ser Phe Gln Tyr Lys Thr Trp Thr Phe Val Val Ser
            1460                1465                1470
Pro Pro Phe Glu Tyr Phe Ile Met Ala Met Ile Ala Leu Asn Thr Val
        1475                1480                1485
Val Leu Met Met Lys Phe Tyr Asp Ala Pro Tyr Glu Tyr Glu Leu Met
    1490                1495                1500
Leu Lys Cys Leu Asn Ile Val Phe Thr Ser Met Phe Ser Leu Glu Cys
1505                1510                1515                1520
Ile Leu Lys Ile Ile Ala Phe Gly Val Leu Asn Tyr Phe Arg Asp Ala
                1525                1530                1535
Trp Asn Val Phe Asp Phe Val Thr Val Leu Gly Ser Ile Thr Asp Ile
            1540                1545                1550
Leu Val Thr Glu Ile Ala Asn Asn Phe Ile Asn Leu Ser Phe Leu Arg
        1555                1560                1565
Leu Phe Arg Ala Ala Arg Leu Ile Lys Leu Cys Arg Gln Gly Tyr Thr
    1570                1575                1580
Ile Arg Ile Leu Leu Trp Thr Phe Val Gln Ser Phe Lys Ala Leu Pro
1585                1590                1595                1600
Tyr Val Cys Leu Leu Ile Ala Met Leu Phe Phe Ile Tyr Ala Ile Ile
                1605                1610                1615
Gly Met Gln Val Phe Gly Asn Ile Ala Leu Asp Asp Gly Thr Ser Ile
            1620                1625                1630
Asn Arg His Asn Asn Phe Arg Thr Phe Leu Gln Ala Leu Met Leu Leu
        1635                1640                1645
Phe Arg Ser Ala Thr Gly Glu Ala Trp His Glu Ile Met Leu Ser Cys
    1650                1655                1660
Leu Gly Asn Arg Ala Cys Asp Pro His Ala Asn Ala Ser Glu Cys Gly
1665                1670                1675                1680
Ser Asp Phe Ala Tyr Phe Tyr Phe Val Ser Phe Ile Phe Leu Cys Ser
                1685                1690                1695
Phe Leu Met Leu Asn Leu Phe Val Ala Val Ile Met Asp Asn Phe Glu
            1700                1705                1710
Tyr Leu Thr Arg Asp Ser Ser Ile Leu Gly Pro His His Leu Asp Glu
        1715                1720                1725
Phe Ile Arg Val Trp Ala Glu Tyr Asp Pro Ala Ala Cys Gly Arg Ile
    1730                1735                1740
Ser Tyr Asn Asp Met Phe Glu Met Leu Lys His Met Ser Pro Pro Leu
1745                1750                1755                1760
Gly Leu Gly Lys Lys Cys Pro Ala Arg Val Ala Tyr Lys Arg Leu Val
                1765                1770                1775
Arg Met Asn Met Pro Ile Ser Asn Glu Asp Met Thr Val His Phe Thr
            1780                1785                1790
Ser Thr Leu Met Ala Leu Ile Arg Thr Ala Leu Glu Ile Lys Leu Ala
        1795                1800                1805
Pro Ala Gly Thr Lys Gln His Gln Cys Asp Ala Glu Leu Arg Lys Glu
    1810                1815                1820
Ile Ser Ser Val Trp Ala Asn Leu Pro Gln Lys Thr Leu Asp Leu Leu
1825                1830                1835                1840
```

-continued

```
Val Pro Pro His Lys Pro Asp Glu Met Thr Val Gly Lys Val Tyr Ala
            1845                1850                1855
Ala Leu Met Ile Phe Asp Phe Tyr Lys Gln Asn Lys Thr Thr Arg Asp
            1860                1865                1870
Gln Thr His Gln Ala Pro Gly Gly Leu Ser Gln Met Gly Pro Val Ser
            1875                1880                1885
Leu Phe His Pro Leu Lys Ala Thr Leu Glu Gln Thr Gln Pro Ala Val
        1890                1895                1900
Leu Arg Gly Ala Arg Val Phe Leu Arg Gln Lys Ser Ala Thr Ser Leu
1905                1910                1915                1920
Ser Asn Gly Gly Ala Ile Gln Thr Gln Glu Ser Gly Ile Lys Glu Ser
            1925                1930                1935
Leu Ser Trp Gly Thr Gln Arg Thr Gln Asp Val Leu Tyr Glu Ala Arg
            1940                1945                1950
Ala Pro Leu Glu Arg Gly His Ser Ala Glu Ile Pro Val Gly Gln Pro
            1955                1960                1965
Gly Ala Leu Ala Val Asp Val Gln Met Gln Asn Met Thr Leu Arg Gly
        1970                1975                1980
Pro Asp Gly Glu Pro Gln Pro Gly Leu Glu Ser Gln Gly Arg Ala Ala
1985                1990                1995                2000
Ser Met Pro Arg Leu Ala Ala Glu Thr Gln Pro Ala Pro Asn Ala Ser
            2005                2010                2015
Pro Met Lys Arg Ser Ile Ser Thr Leu Ala Pro Arg Pro His Gly Thr
            2020                2025                2030
Gln Leu Cys Asn Thr Val Leu Asp Arg Pro Pro Ser Gln Val Ser
        2035                2040                2045
His His His His His Arg Cys His Arg Arg Asp Lys Lys Gln Arg
        2050                2055                2060
Ser Leu Glu Lys Gly Pro Ser Leu Ser Val Asp Thr Glu Gly Ala Pro
2065                2070                2075                2080
Ser Thr Ala Ala Gly Ser Gly Leu Pro His Gly Glu Gly Ser Thr Gly
            2085                2090                2095
Cys Arg Arg Glu Arg Lys Gln Glu Arg Gly Arg Ser Gln Glu Arg Arg
            2100                2105                2110
Gln Pro Ser Ser Ser Ser Ser Glu Lys Gln Arg Phe Tyr Ser Cys Asp
        2115                2120                2125
Arg Phe Gly Ser Arg Glu Pro Pro Gln Pro Lys Pro Ser Leu Ser Ser
        2130                2135                2140
His Pro Ile Ser Pro Thr Ala Ala Leu Glu Pro Gly Pro His Pro Gln
2145                2150                2155                2160
Gly Ser Gly Ser Val Asn Gly Ser Pro Leu Met Ser Thr Ser Gly Ala
            2165                2170                2175
Ser Thr Pro Gly Arg Gly Gly Arg Arg Gln Leu Pro Gln Thr Pro Leu
            2180                2185                2190
Thr Pro Arg Pro Ser Ile Thr Tyr Lys Thr Ala Asn Ser Ser Pro Val
        2195                2200                2205
His Phe Ala Glu Gly Gln Ser Gly Leu Pro Ala Phe Ser Pro Gly Arg
        2210                2215                2220
Leu Ser Arg Gly Leu Ser Glu His Asn Ala Leu Leu Gln Lys Glu Pro
2225                2230                2235                2240
Leu Ser Gln Pro Leu Ala Ser Gly Ser Arg Ile Gly Ser Asp Pro Tyr
            2245                2250                2255
```

-continued

Leu Gly Gln Arg Leu Asp Ser Glu Ala Ser Ala His Asn Leu Pro Glu
            2260                2265                2270

Asp Thr Leu Thr Phe Glu Glu Ala Val Ala Thr Asn Ser Gly Arg Ser
        2275                2280                2285

Ser Arg Thr Ser Tyr Val Ser Ser Leu Thr Ser Gln Ser His Pro Leu
    2290                2295                2300

Arg Arg Val Pro Asn Gly Tyr His Cys Thr Leu Gly Leu Ser Thr Gly
2305                2310                2315                2320

Val Arg Ala Arg His Ser Tyr His His Pro Asp Gln Asp His Trp Cys
            2325                2330                2335

<210> SEQ ID NO 11
<211> LENGTH: 4
<212> TYPE: PRT
<213> ORGANISM: Conus geographus

<400> SEQUENCE: 11

Gly Val Ile Ala
  1

<210> SEQ ID NO 12
<211> LENGTH: 5
<212> TYPE: PRT
<213> ORGANISM: Conus magus

<400> SEQUENCE: 12

Met Val Ile Ile Ala
  1               5

<210> SEQ ID NO 13
<211> LENGTH: 23
<212> TYPE: DNA
<213> ORGANISM: Rattus norvegicus

<400> SEQUENCE: 13
attcttgtgg tcatcgcctt gag                                    23

<210> SEQ ID NO 14
<211> LENGTH: 23
<212> TYPE: DNA
<213> ORGANISM: Rattus norvegicus

<400> SEQUENCE: 14
gacaggcctc caggagcttg gtg                                    23

<210> SEQ ID NO 15
<211> LENGTH: 27
<212> TYPE: DNA
<213> ORGANISM: Rattus norvegicus

<400> SEQUENCE: 15
gagattgcgg caacgaacaa cttcatc                                27

<210> SEQ ID NO 16
<211> LENGTH: 25
<212> TYPE: DNA
<213> ORGANISM: Rattus norvegicus

<400> SEQUENCE: 16
aagttgttcg tttccgcaat ctccg                                  25

<210> SEQ ID NO 17

-continued

```
<211> LENGTH: 27
<212> TYPE: DNA
<213> ORGANISM: Rattus norvegicus

<400> SEQUENCE: 17
gagattgcgc agacgaacaa cttcatc                                              27

<210> SEQ ID NO 18
<211> LENGTH: 25
<212> TYPE: DNA
<213> ORGANISM: Rattus norvegicus

<400> SEQUENCE: 18
aagttgttcg tctgcgcaat ctccg                                                25

<210> SEQ ID NO 19
<211> LENGTH: 27
<212> TYPE: DNA
<213> ORGANISM: Rattus norvegicus

<400> SEQUENCE: 19
gagattgcgg aagctaacaa cttcatc                                              27

<210> SEQ ID NO 20
<211> LENGTH: 25
<212> TYPE: DNA
<213> ORGANISM: Rattus norvegicus

<400> SEQUENCE: 20
aagttgttag cttccgcaat ctccg                                                25

<210> SEQ ID NO 21
<211> LENGTH: 27
<212> TYPE: DNA
<213> ORGANISM: Rattus norvegicus

<400> SEQUENCE: 21
gagattgcgg cagctaacaa cttcatc                                              27

<210> SEQ ID NO 22
<211> LENGTH: 25
<212> TYPE: DNA
<213> ORGANISM: Rattus norvegicus

<400> SEQUENCE: 22
aagttgttag ctgccgcaat ctccg                                                25

<210> SEQ ID NO 23
<211> LENGTH: 27
<212> TYPE: DNA
<213> ORGANISM: Rattus norvegicus

<400> SEQUENCE: 23
gagattgcga accctaacaa cttcatc                                              27

<210> SEQ ID NO 24
<211> LENGTH: 25
<212> TYPE: DNA
<213> ORGANISM: Rattus norvegicus

<400> SEQUENCE: 24
aagttgttag ggttcgcaat ctccg                                                25
```

-continued

```
<210> SEQ ID NO 25
<211> LENGTH: 26
<212> TYPE: DNA
<213> ORGANISM: Rattus norvegicus

<400> SEQUENCE: 25
tgcctggaac atcttcgact ttgtga                                         26

<210> SEQ ID NO 26
<211> LENGTH: 26
<212> TYPE: DNA
<213> ORGANISM: Rattus norvegicus

<400> SEQUENCE: 26
cagaggagaa tgcggatggt gtaacc                                         26

<210> SEQ ID NO 27
<211> LENGTH: 25
<212> TYPE: DNA
<213> ORGANISM: Rattus norvegicus

<400> SEQUENCE: 27
cagagatgcc tggaacgtct ttgac                                          25

<210> SEQ ID NO 28
<211> LENGTH: 25
<212> TYPE: DNA
<213> ORGANISM: Rattus norvegicus

<400> SEQUENCE: 28
ataacaagat gcggatggtg tagcc                                          25
```

HUMAN N-TYPE CALCIUM CHANNEL ISOFORM

RELATED APPLICATION

This application claims benefit under 35 U.S.C. §119(e) from United States provisional application serial. No. 60/077,901, filed Mar. 13, 1998, the disclosure of which is incorporated by reference herein.

FIELD OF THE INVENTION

The invention pertains to human N-type calcium channel $\alpha_{1B}$ subunit isoforms.

BACKGROUND OF THE INVENTION

Voltage gated calcium channels, also known as voltage dependent calcium channels (VDCCs) are multisubunit membrane spanning proteins which permit controlled calcium influx from an extracellular environment into the interior of a cell. Several types of voltage gated calcium channel have been described in different tissues, including N-type, P/Q-type, L-type and T-type channels. A voltage gated calcium channel permits entry into the cell of calcium upon depolarization of the membrane of the cell, which is a lessening of the difference in electrical potential between the outside and the inside of the cell.

A voltage gated calcium channel contains several proteins, including $\alpha_1$, $\alpha_2$, $\beta$, and $\gamma$ subunits. Subtypes of the calcium channel subunits also are known. For instance, $\alpha_1$ subtypes include $\alpha_{1A}$, $\alpha_{1B}$, $\alpha_{1C}$, $\alpha_{1D}$, $\alpha_{1E}$ and $\alpha_{1S}$. Each subunit may have one or more isoforms which result from alternative splicing of RNA in the formation of a completed messenger RNA which encodes the subunit. For example, at least four isoforms of the rat N-type $\alpha_{1B}$ subunit are known (see, e.g., Lin et al., Neuron 18:153–166, 1997).

Isoforms of calcium channel $\alpha_1$ subunits may be expressed differently in different tissues (see, e.g., Lin et al., 1997). Differential expression of subunits isoforms raises the possibility of developing therapeutics which are specific for distinct isoforms of the $\alpha_1$ subunits, thereby lessening side effects resulting from the use of therapeutics which are effective for more than one calcium channel isoform. Two isoforms of the human N-type calcium channel $\alpha_{1B}$ subunit were published by Williams et al in 1992 (Science 257:389–395). Given the existence of several additional rat isoforms in a highly conserved gene family, it is surprising that additional human isoforms of the N-type calcium channel $\alpha_{1B}$ subunit have not been discovered. Such isoforms would be useful for developing isoform-specific therapeutics.

SUMMARY OF THE INVENTION

The invention provides isolated nucleic acid molecules, unique fragments of those molecules, expression vectors containing the foregoing, and host cells transfected with those molecules. The invention also provides isolated polypeptides and inhibitors of the foregoing nucleic acids and polypeptides which reduce voltage-gated calcium influx. The foregoing can be used in the diagnosis or treatment of conditions characterized by increased or decreased human N-type calcium channel $h\alpha_{1B+SFVG}$ subunit activity and can be used in methods in which it is therapeutically useful to increase or decrease human N-type calcium channel $h\alpha_{1B+SFVG}$ subunit activity such as treatments for stroke, pain (e.g., neuropathic pain), traumatic brain injury and conditions characterized by increased or decreased voltage regulated calcium influx. Here, we present the identification of a novel human N-type calcium channel $\alpha_{1B}$ subunit, $h\alpha_{1B+SFVG}$, which plays a role in voltage-gated calcium influx.

It was discovered that a brain $\alpha_{1B}$ calcium channel subunit isoform (splice variant) contains a four amino acid insert relative to published human $\alpha_{1B}$ calcium channel isoforms (SEQ ID NO:5 [GenBank accession number M94172], SEQ ID NO:7 [GenBank accession number M94173]). Surprisingly, this insert, SFVG (SEQ ID NO:2, encoded by SEQ ID NO:1), is similar but not identical to an insert found in a rat $\alpha_{1B}$ channel (GenBank accession number M92905). A significant proportion of the human N-type calcium channel $\alpha_{1B}$ subunit mRNA in brain was found to be the $h\alpha_{1B+SFVG}$ sub-type; given the abundance of its expression the isolation of this sub-type so long after the identification of other $\alpha_{1B}$ isoforms is unexpected. The SFVG-containing human N-type calcium channel $h\alpha_{1B+SFVG}$ subunit also lacks an amino acid sequence, ET, which is present in published human N-type calcium channel $h\alpha_{1B+SFVG}$ subunit isoforms (amino acids 1557–1558 of SEQ ID NOs:5 and 7).

The invention involves in one aspect an isolated human N-type calcium channel $\alpha_{1B}$ subunit polypeptide which includes the amino acid sequence of SEQ ID NO:2 (an $h\alpha_{1B+SFVG}$ polypeptide). In one embodiment, the polypeptide comprises the amino acid sequence of SEQ ID NO:4, and preferably consists of the amino acid sequence of SEQ ID NO:4. In another embodiment the $h\alpha_{1B+SFVG}$ calcium channel polypeptide is a fragment or variant of the foregoing polypeptides, wherein the fragment or variant includes the amino acid sequence of SEQ ID NO:2 or additions, deletions or substitutions thereof which confer the same function as SEQ ID NO: 2. Preferred variants include those having additions, substitutions or deletions relative to the human N-type calcium channel $h\alpha_{1B+SFVG}$ subunit polypeptide sequence disclosed herein, particularly those variants which retain one or more of the activities of the human N-type calcium channel $h\alpha_{1B+SFVG}$ subunit, including subunits with or without the ET exon sequence.

According to another aspect of the invention, an isolated nucleic acid molecule which encodes any of the foregoing human N-type calcium channel $h\alpha_{1B+SFVG}$ subunit polypeptide is provided. In certain embodiments, the nucleic acid molecule includes SEQ ID NO:1. In one preferred embodiment, the human N-type calcium channel $h\alpha_{1B+SFVG}$ subunit polypeptides is encoded by a nucleic acid molecule which comprises the nucleotide sequence of SEQ ID NO:3 (Williams et al. sequence +SFVG, -ET), and which preferably consists of the nucleotide sequence of SEQ ID NO:3. In another embodiment the nucleic acid is an allele of the nucleic acid sequence of SEQ ID NO:3.

In another aspect the invention is an expression vector comprising the human N-type calcium channel $h\alpha_{1B+SFVG}$ subunit nucleic acid molecule operably linked to a promoter. Also included within the invention is a host cell transformed or transfected with the expression vector.

According to another aspect of the invention, an agent which selectively binds the human N-type calcium channel $h\alpha_{1B+SFVG}$ subunit polypeptide or a nucleic acid that encodes the human N-type calcium channel $h\alpha_{1B+SFVG}$ subunit polypeptide is provided. By "selectively binds" it is meant that the agent binds the human N-type calcium channel $h\alpha_{1B+SFVG}$ subunit polypeptide or nucleic acid, or any fragment thereof which retains the amino acids of SEQ ID NO:2 or the nucleotides of SEQ ID NO:1, to a greater extent than the agent binds other human N-type calcium channel $\alpha_{1B}$ subunit isoforms, and preferably does not bind other human N-type calcium channel $\alpha_{1B}$ subunit isoforms. In one embodiment, the agent is a polypeptide which binds selectively to the human N-type calcium channel h$\alpha_{1B+SFVG}$ subunit polypeptide. The polypeptide can be a monoclonal antibody, a polyclonal antibody, or an antibody fragment selected from the group consisting of a Fab fragment, a F(ab)$_2$ fragment and a fragment including a CDR3 region. In another embodiment, the agent is an antisense nucleic acid which selectively binds to a nucleic acid encoding the human N-type calcium channel h$\alpha_{1B+SFVG}$ subunit polypeptide. Preferably the foregoing agents are inhibitors (antagonists) or agonists of the calcium channel activity of the human N-type calcium channel h$\alpha_{1B+SFVG}$ subunit polypeptide.

According to another aspect of the inventions, a dominant negative human N-type calcium channel h$\alpha_{1B+SFVG}$ subunit polypeptide is provided. The dominant negative polypeptide is an inhibitor of the function of the calcium channel.

The invention also provides compositions including any of the foregoing polypeptides, nucleic acids or agents in combination with a pharmaceutically acceptable carrier.

In another aspect of the invention a method for inhibiting human N-type calcium channel h$\alpha_{1B+SFVG}$ subunit activity in a mammalian cell is provided. The method involves the step of contacting the mammalian cell with an amount of a human N-type calcium channel h$\alpha_{1B+SFVG}$ subunit inhibitor effective to inhibit calcium influx in the mammalian cell. Preferably the inhibitor is selected from the group consisting of a peptide or an antibody which selectively binds the human N-type calcium channel h$\alpha_{1B+SFVG}$ subunit polypeptide, an antisense nucleic acid which binds a nucleic acid encoding human N-type calcium channel h$\alpha_{1B+SFVG}$ subunit polypeptide and a dominant negative human N-type calcium channel h$\alpha_{1B+SFVG}$ subunit polypeptide.

According to still another aspect the invention, a method for treating a subject having a stroke, pain (e.g., neuropathic pain), or traumatic brain injury is provided. The method involves the step of administering to a subject in need of such treatment an inhibitor of the human N-type calcium channel h$\alpha_{1B+SFVG}$ subunit polypeptide in an amount effective to inhibit voltage regulated calcium influx. In another embodiment of the foregoing methods, the inhibitor is administered prophylactically to a subject at risk of having a stroke.

The human N-type calcium channel h$\alpha_{1B+SFVG}$ subunit polypeptides and nucleic acids which encode such polypeptides are useful for increasing the amount of human N-type calcium channel h$\alpha_{1B+SFVG}$ subunit polypeptides in a cell. Increasing the amount of human N-type calcium channel h$\alpha_{1B+SFVG}$ subunit polypeptides in a cell results in increased voltage regulated calcium influx. This is useful where it is desired to increase the amount of voltage regulated calcium influx which is mediated by a human N-type calcium channel.

Thus according to another aspect of the invention, a method for increasing human N-type calcium channel h$\alpha_{1B+SFVG}$ subunit expression in a cell is provided. The method involves the step of contacting the cell with a molecule selected from the group consisting of a human N-type calcium channel h$\alpha_{1B+SFVG}$ subunit nucleic acid and a human N-type calcium channel h$\alpha_{1B+SFVG}$ subunit polypeptide in an amount effective to increase voltage regulated calcium influx in the cell. In certain embodiments, the cell is contacted with one or more human N-type calcium channel non-h$\alpha_{1B+SFVG}$ subunits, such as a $\beta$ subunit, or nucleic acids encoding such non-h$\alpha_{1B+SFVG}$ subunits.

According to another aspect of the invention, a method for increasing calcium channel voltage regulated calcium influx in a subject is provided. The method involves the step of administering to a subject in need of such treatment a molecule selected from the group consisting of a human N-type calcium channel h$\alpha_{1B+SFVG}$ subunit nucleic acid and a human N-type calcium channel h$\alpha_{1B+SFVG}$ subunit polypeptide in an amount effective to increase voltage regulated calcium influx in the subject.

According to a further aspect of the invention, a method for identifying lead compounds for a pharmacological agent useful in the treatment of disease associated with increased or decreased voltage regulated calcium influx mediated by a human N-type calcium channel is provided. A cell or other membrane-encapsulated space comprising a human N-type calcium channel h$\alpha_{1B+SFVG}$ subunit polypeptide is provided. The cell or other membrane-encapsulated space preferably is loaded with a calcium-sensitive compound which is detectable in the presence of calcium. The cell or other membrane-encapsulated space is contacted with a candidate pharmacological agent under conditions which, in the absence of the candidate pharmacological agent, cause a first amount of voltage regulated calcium influx into the cell or other membrane-encapsulated space. A test amount of voltage regulated calcium influx then is determined. For example, in a preferred embodiment, fluorescence of a calcium-sensitive compound then is detected as a measure of the voltage regulated calcium influx. If the test amount of voltage regulated calcium influx is less than the first amount, then the candidate pharmacological agent is a lead compound for a pharmacological agent which reduces voltage regulated calcium influx. If the test amount of voltage regulated calcium influx is greater than the first amount, then the candidate pharmacological agent is a lead compound for a pharmacological agent which increases voltage regulated calcium influx.

In another aspect of the invention, methods for identifying compounds which selectively or preferentially bind a human N-type calcium channel h$\alpha_{1B+SFVG}$ subunit isoform are provided. In one embodiment, the method includes providing a first cell or membrane encapsulated space which expresses a human N-type calcium channel h$\alpha_{1B+SFVG}$ subunit isoform, and providing a second cell or membrane encapsulated space which expresses a human N-type calcium channel non-h$\alpha_{1B+SFVG}$ subunit isoform, wherein the second cell or membrane encapsulated space is identical to the first cell except for the $\alpha_{1B}$ isoform expressed. The first cell or membrane encapsulated space and the second cell or membrane encapsulated space are contacted with a compound, and the binding of the compound to the first cell or membrane encapsulated space and the second cell or membrane encapsulated space is determined. A compound which binds the first cell or membrane encapsulated space but does not bind the second cell or membrane encapsulated space is a compound which selectively binds the human N-type calcium channel h$\alpha_{1B+SFVG}$ subunit isoform. A compound which binds the first cell or membrane encapsulated space in an amount greater than the compound binds the second cell or membrane encapsulated space is a compound which preferentially binds the human N-type calcium channel h$\alpha_{1B+SFVG}$ subunit isoform. In another embodiment of the method, a human N-type calcium channel h$\alpha_{1B+SFVG}$ subunit isoform polypeptide or nucleic acid and a human N-type calcium channel non-h$\alpha_{1B+SFVG}$ subunit isoform polypeptide or nucleic acid are provided and contacted with a compound. The binding of the compound to the human N-type calcium channel hα$_{1B+SFVG}$ subunit isoform polypeptide or nucleic acid and the human N-type calcium channel non-hα$_{1B+SFVG}$ subunit isoform polypeptide or nucleic acid then is determined. A compound which binds the human N-type calcium channel hα$_{1B+SFVG}$ subunit isoform polypeptide or nucleic acid but does not bind the human N-type calcium channel non-hα$_{1B+SFVG}$ subunit isoform polypeptide or nucleic acid is a compound which selectively binds the human N-type calcium channel hα$_{1B+SFVG}$ subunit isoform polypeptide or nucleic acid. A compound which binds the human N-type calcium channel hα$_{1B+SFVG}$ subunit isoform polypeptide or nucleic acid in an amount greater than the human N-type calcium channel non-hα$_{1B+SFVG}$ subunit isoform polypeptide or nucleic acid is a compound which preferentially binds the human N-type calcium channel hα$_{1B+SFVG}$ subunit isoform polypeptide or nucleic acid. Also included in the invention are compounds identified using the foregoing methods.

According to another aspect of the invention, a method for selectively treating a subject having a condition characterized by aberrant brain neuronal calcium current is provided. The method includes the step of administering to a subject in need of such treatment a pharmacological agent which is selective for a human N-type calcium channel hα$_{1B+SFVG}$ subunit, in an amount effective to normalize the aberrant neuronal calcium current. Aberrant means a level of calcium current (calcium influx) which is outside of a normal range as understood in the medical arts. Normalize means that the calcium current is brought within the normal range.

Also presented herein is an identification of characteristics of certain calcium channel subunit isoforms with respect to voltage-dependent activation. It has been discovered, surprisingly, that the presence or absence of an exon comprising the amino acids ET is important for the kinetics of channel activation. Thus, in still other aspects of the invention, a variety of novel assays, screens, recombinant products, model systems (such as animal models) and methods are provided which utilize the unexpected different activation functions between and among the calcium channel subunit isoforms for the identification of novel agents, treatments, etc. useful in the modulation of conditions which arise from or manifest differences in action potential neurotransmitter release, voltage-dependent calcium channel activation, and so on. For example, methods for the identification of agents which alter activation potential dependent neurotransmitter release are provided. The methods include selecting an agent which binds a calcium channel isoform having or lacking a IVS3-S4 ET exon as described herein, and determining calcium channel activation or activation potential dependent neurotransmitter release in the presence and the absence of the agent. In some embodiments, candidate compounds may be screened by such methods. The methods also can include measurement of these parameters in other calcium channel subunits which manifest such differences in activation kinetics, including subunits in which an NP exon is added or is substituted for the ET exon.

Use of the foregoing compositions in the preparation of a medicament, and particularly in the preparation of a medicament for the treatment of stroke, pain (e.g., neuropathic pain), traumatic brain injury, or a condition which results from excessive or insufficient voltage regulated calcium influx, is provided.

These and other aspects of the invention are described in greater detail below.

BRIEF DESCRIPTION OF THE SEQUENCES

Figure 1:
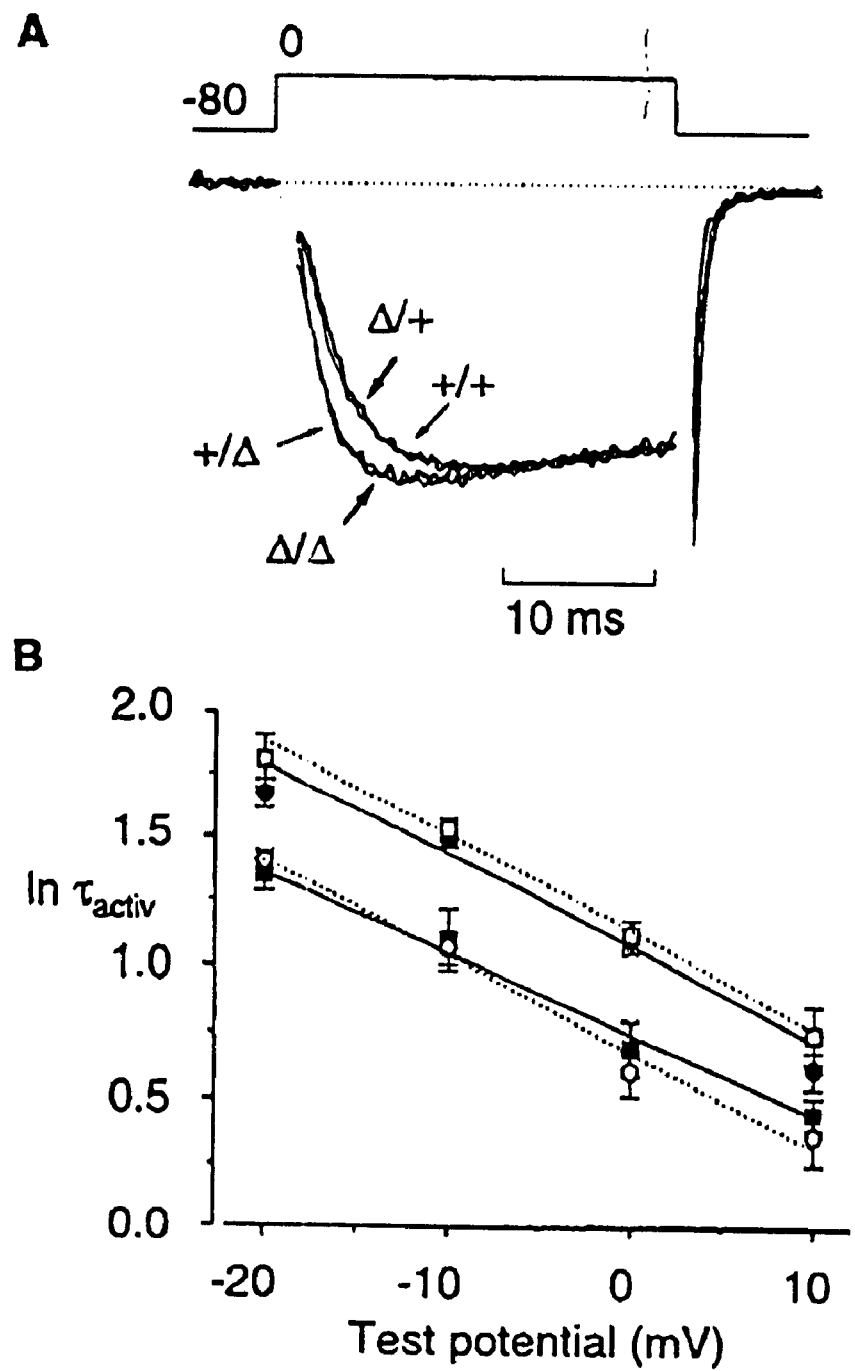
FIGS. 1A & B, show that the presence of ET in domain IVS3-S4 of α$_{1B}$ slows the rate of N-type Ca channel activation.

SEQ ID NO:1 is the nucleotide sequence of the human N-type calcium channel hα$_{1B+SFVG}$ subunit cDNA IIIS3-S4 "SFVG" site.

SEQ ID NO:2 is the amino acid sequence of the human N-type calcium channel hα$_{1B+SFVG}$ subunit polypeptide IIIS3-S4 "SFVG" site.

SEQ ID NO:3 is the nucleotide sequence of the human N-type calcium channel hα$_{1B+SFVG}$ subunit cDNA.

SEQ ID NO:4 is the amino acid sequence of the human N-type calcium channel hα$_{1B+SFVG}$ subunit polypeptide.

SEQ ID NO:5 is the nucleotide sequence of the coding region of a human α$_{1B}$ calcium channel which lacks the IIIS3-S4 "SFVG" site (Prior art, GenBank accession number M94172).

SEQ ID NO:6 is the amino acid sequence of a human α$_{1B}$ calcium channel which lacks the IIIS3-S4 "SFVG" site (Prior art, GenBank accession number M94172).

SEQ ID NO:7 is the nucleotide sequence of the coding region of a human α$_{1B}$ calcium channel which lacks the IIIS3-S4 "SFVG" site (Prior art, GenBank accession number M94173).

SEQ ID NO:8 is the amino acid sequence of a human α$_{1B}$ calcium channel which lacks the IIIS3-S4 "SFVG" site (Prior art, GenBank accession number M94173).

SEQ ID NO:9 is the nucleotide sequence of the coding region of a rat α$_{1B}$ calcium channel which contains a SFMG site (Prior art, GenBank accession number M92905).

SEQ ID NO:10 is the amino acid sequence of a rat α$_{1B}$ calcium channel which contains a SFMG site (Prior art, GenBank accession number M92905).

SEQ ID NO:11 is the amino acid sequence of an ω-conotoxin peptide from C. geographus.

SEQ ID NO:12 is the amino acid sequence of ω-conotoxin peptide from C. magus.

SEQ ID NOS:13–28 are primers for PCR and/or sequencing.

DETAILED DESCRIPTION OF THE INVENTION

The present invention in one aspect involves the identification of a cDNA encoding a novel human isoform of the N-type calcium channel, referred to herein as the human N-type calcium channel hα$_{1B+SFVG}$ subunit. As used herein, hα$_{1B+SFVG}$ refers to any human N-type calcium channel α$_{1B}$ subunit clone that contains the SFVG sequence set forth in SEQ ID NO:2. The nucleotide sequence of the human N-type calcium channel hα$_{1B+SFVG}$ subunit insert, the IIIS3-S4 "SFVG" site, is presented as SEQ ID NO:1 and the amino acid sequence of the human N-type calcium channel hα$_{1B+SFVG}$ subunit insert, the IIIS3-S4 "SFVG" site, is presented as SEQ ID NO:2. The 12 nucleotides of SEQ ID NO:1 are inserted immediately following nt 3855 in the coding sequence of the human N-type calcium channel α$_{1B}$ subunit in the codon encoding amino acid 1237, such that the four amino acids of SEQ ID NO:2 are inserted in the polypeptide after amino acid 1237 (see SEQ ID NO:3). The closely related human N-type calcium channel $\alpha_{1B-b}$ subunit, which does not contain the IIIS3-S4 "SFVG" site, was deposited in GenBank under accession numbers M94172 and M94173 (SEQ ID NOs:5–8). A related rat N-type calcium channel $\alpha_{1B}$ subunit was deposited in GenBank under accession number M92905 (SEQ ID NOs:9 and 10). Surprisingly, the amino acid sequence of the human N-type calcium channel $h\alpha_{1B+SFVG}$ subunit differs from the rat amino acid sequence in the SFVG site, which sequence is located in an area of the molecule in which the human and rat amino acid sequences are otherwise 100% identical. This species difference in the very highly conserved protein domain of the human N-type calcium channel $h\alpha_{1B+SFVG}$ subunit is entirely unexpected, and permits the screening of compounds which selectively bind to and/or modulate the human N-type calcium channel $h\alpha_{1B+SFVG}$ subunit. Because the present human N-type calcium channel $h\alpha_{1B+SFVG}$ subunit is a splice variant of other human N-type calcium channel $\alpha_{1B}$ subunits, it is apparent that the invention is meant to embrace human N-type calcium channel $\alpha_{1B}$ subunit variants which vary by alternative splicing of sequences other than the SFVG (SEQ ID NO:2) insert. For example, the invention embraces polypeptides which contain or do not contain an Ala residue immediately following amino acid position 414 of SEQ ID NO:3, or a Glu-Thr insert (ET in single letter code) at amino acid positions 1557–1558 (see, e.g., SEQ ID NO:6), as well as nucleic acid molecules encoding such splice variant polypeptides. As shown in the Examples, the $h\alpha_{1B+SFVG}$ subunit is a significant portion of the $\alpha_{1B}$ calcium channel expressed in human brain, and is differentially distributed in different parts of the brain. This opens the possibility for the selective treatment of disorders which involve those parts of the brain.

The invention involves in one aspect human N-type calcium channel $h\alpha_{1B+SFVG}$ subunit nucleic acids and polypeptides, as well as therapeutics relating thereto. The invention also embraces isolated functionally equivalent variants, useful analogs and fragments of the foregoing nucleic acids and polypeptides; complements of the foregoing nucleic acids; and molecules which selectively bind the foregoing nucleic acids and polypeptides.

The human N-type calcium channel $h\alpha_{1B+SFVG}$ subunit nucleic acids and polypeptides of the invention are isolated. The term "isolated", as used herein in reference to a nucleic acid molecule, means a nucleic acid sequence: (i) amplified in vitro by, for example, polymerase chain reaction (PCR); (ii) synthesized by, for example, chemical synthesis; (iii) recombinantly produced by cloning; or (iv) purified, as by cleavage and electrophoretic or chromatographic separation. The term "isolated", as used herein in reference to a polypeptide, means a polypeptide encoded by an isolated nucleic acid sequence, as well as polypeptides synthesized by, for example, chemical synthetic methods, and polypeptides separated from biological materials, and then purified, using conventional protein analytical or preparatory procedures, to an extent that permits them to be used according to the methods described herein.

As used herein a human N-type calcium channel $h\alpha_{1B+SFVG}$ subunit nucleic acid refers to an isolated nucleic acid molecule which codes for a human N-type calcium channel $h\alpha_{1B+SFVG}$ subunit. Human N-type calcium channel $h\alpha_{1B+SFVG}$ subunit nucleic acids are those nucleic acid molecules which code for human N-type calcium channel $h\alpha_{1B+SFVG}$ subunit polypeptides which include the sequence of SEQ ID NO:2. The nucleic acid molecules include the nucleotide sequence of SEQ ID NO:1 and nucleotide sequences which differ from the sequence of SEQ ID NO:1 in codon sequence due to the degeneracy of the genetic code. The human N-type calcium channel $h\alpha_{1B+SFVG}$ subunit nucleic acids of the invention also include alleles of the foregoing nucleic acids, as well as fragments of the foregoing nucleic acids, provided that the allele or fragment encodes the amino acid sequence of SEQ ID NO:2. Such fragments can be used, for example, as probes in hybridization assays and as primers in a polymerase chain reaction (PCR). Preferred human N-type calcium channel $h\alpha_{1B+SFVG}$ subunit nucleic acids include the nucleic acid sequence of SEQ ID NO: 1. Complements of the foregoing nucleic acids also are embraced by the invention.

As used herein "human N-type calcium channel $h\alpha_{1B+SFVG}$ subunit activity" refers to an ability of a molecule to modulate voltage regulated calcium influx. A molecule which inhibits human N-type calcium channel $h\alpha_{1B+SFVG}$ subunit activity (an antagonist) is one which inhibits voltage regulated calcium influx via this calcium channel and a molecule which increases human N-type calcium channel $h\alpha_{1B+SFVG}$ subunit activity (an agonist) is one which increases voltage regulated calcium influx via this calcium chaimel. Changes in human N-type calcium channel $\alpha_{1B+SFVG}$ subunit activity can be measured by changes in voltage regulated calcium influx by in vitro assays such as those disclosed herein, including patch-clamp assays and assays employing calcium sensitive fluorescent compounds such as fura-2.

Alleles of the human N-type calcium channel $h\alpha_{1B+SFVG}$ subunit nucleic acids of the invention can be identified by conventional techniques. For example, alleles of human human N-type calcium channel $h\alpha_{1B+SFVG}$ subunit can be isolated by hybridizing a probe which includes SEQ ID NO:1 under stringent conditions with a cDNA library and selecting positive clones. Thus, an aspect of the invention is those nucleic acid sequences which code for human N-type calcium channel $h\alpha_{1B+SFVG}$ subunit polypeptides and which hybridize to a nucleic acid molecule consisting of SEQ ID NO:1 under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1×SDS at temperatures up to 65° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of alleles of human N-type calcium channel $h\alpha_{1B+SFVG}$ subunit nucleic acids of the invention. The skilled artisan also is familiar with the methodology for screening cells and libraries for expression of such molecules which then are routinely isolated, followed by isolation of the pertinent nucleic acid molecule and sequencing.

In screening for human N-type calcium channel $h\alpha_{1B+SFVG}$ subunit nucleic acids, a Southern blot may be performed using the foregoing stringent conditions, together with a radioactive probe. After washing the membrane to which the DNA is finally transferred, the membrane can be placed against X-ray film to detect the radioactive signal.

The human N-type calcium channel $h\alpha_{1B+SFVG}$ subunit nucleic acids of the invention also include degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating human N-type calcium channel $h\alpha_{1B+SFVG}$ subunit polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated fragments of SEQ ID NO:3 which include the nucleotide sequence of SEQ ID NO:1. The fragments can be used as probes in Southern blot assays to identify such nucleic acids, or can be used in amplification assays such as those employing PCR. Smaller fragments are those comprising 12, 13, 14, 15, 16, 17, 18, 20, 22, 25, 30, 40, 50, or 75 nucleotides, and every integer therebetween and are useful e.g. as primers for nucleic acid amplification procedures. As known to those skilled in the art, larger probes such as 200, 250, 300, 400 or more nucleotides are preferred for certain uses such as Southern blots, while smaller fragments will be preferred for uses such as PCR. Fragments also can be used to produce fusion proteins for generating antibodies or determining binding of the polypeptide fragments. Likewise, fragments can be employed to produce non-fused fragments of the human N-type calcium channel $h\alpha_{1B+SFVG}$ subunit polypeptides, useful, for example, in the preparation of antibodies, in immunoassays, and the like. The foregoing nucleic acid fragments further can be used as antisense molecules to inhibit the expression of human N-type calcium chaimel $h\alpha_{1B+SFVG}$ subunit nucleic acids and polypeptides, particularly for therapeutic purposes as described in greater detail below.

The invention also includes functionally equivalent variants of the human N-type calcium channel $h\alpha_{1B+SFVG}$ subunit, which include variant nucleic acids and polypeptide which retain one or more of the functional properties of the human N-type calcium channel $h\alpha_{1B+SFVG}$ subunit, but always including SEQ ID NO:2. For example, variants include a fusion protein which includes the extracellular and transmembrane domains of the human N-type calcium channel $h\alpha_{1B+SFVG}$ subunit (including SEQ ID NO:2), which retains the ability to bind ligand and/or transduce a voltage gated calcium current. Still other functionally equivalent variants include variants of SEQ ID NO:2 which retain functions of subunit including SEQ ID NO: 2. Functionally equivalent variants also include a human N-type calcium channel $h\alpha_{1B+SFVG}$ subunit which has had a portion of the extracellular domain (but not SEQ ID NO:2) removed or replaced by a similar domain from another calcium channel $\alpha_1$ subunit (e.g. a "domain-swapping" variant). Other functionally equivalent variants will be known to one of ordinary skill in the art, as will methods for preparing such variants. TIhe activity of a functionally equivalent variant can be determined using the methods provided herein, in Lin et al., Neuron 18:153–166, 1997, and in U.S. Pat. No. 5,429,921. Such variants are useful, inter alia, in assays for identification of compounds which bind and/or regulate the calcium influx function of the human N-type calcium channel $h\alpha_{1B+SFVG}$ subunit, and for determining the portions of the human N-type calcium channel $h\alpha_{1B+SFVG}$ subunit which are required for calcium influx activity.

Variants which are non-functional also can be prepared as described above. Such variants are useful, for example, as negative controls in experiments testing subunit activity, and as inhibition of N-type calcium channel activity.

A human N-type calcium channel $h\alpha_{1B+SFVG}$ subunit nucleic acid, in one embodiment, is operably linked to a gene expression sequence which directs the expression of the human N-type calcium channel $h\alpha_{1B+SFVG}$ subunit nucleic acid within a eukaryotic or prokaryotic cell. The "gene expression sequence" is any regulatory nucleotide sequence, such as a promoter sequence or promoter-enhancer combination, which facilitates the efficient transcription and translation of the human N-type calcium channel $h\alpha_{1B+SFVG}$ subunit nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, β-actin promoter and other constitutive promoters. Exemplary viral promoters which function constitutively in eukaryotic cells include, for example, promoters from the simian virus, papilloma virus, adenovirus, human immunodeficiency virus (HIV), Rous sarcoma virus, cytomegalovirus, the long terminal repeats (LTR) of Moloney murine leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

In general, the gene expression sequence shall include, as necessary, 5' non-transcribing and 5' non-translating sequences involved with the initiation of transcription and translation, respectively, such as a TATA box, capping sequence, CAAT sequence, and the like. Especially, such 5' non-transcribing sequences will include a promoter region which includes a promoter sequence for transcriptional control of the operably joined human N-type calcium channel $h\alpha_{1B+SFVG}$ subunit nucleic acid. The gene expression sequences optionally includes enhancer sequences or upstream activator sequences as desired.

The human N-type calcium channel $h\alpha_{1B+SFVG}$ subunit nucleic acid sequence and the gene expression sequence are said to be "operably linked" when they are covalently linked in such a way as to place the transcription and/or translation of the human N-type calcium channel $h\alpha_{1B+SFVG}$ subunit coding sequence under the influence or control of the gene expression sequence. If it is desired that the human N-type calcium channel h$\alpha_{1B+SFVG}$ subunit sequence be translated into a functional protein, two DNA sequences are said to be operably linked if induction of a promoter in the 5' gene expression sequence results in the transcription of the human N-type calcium channel h$\alpha_{1B+SFVG}$ subunit sequence and if the nature of the linkage between the two DNA sequences does not (1) result in the introduction of a frame-shift mutation, (2) interfere with the ability of the promoter region to direct the transcription of the human N-type calcium channel h$\alpha_{1B+SFVG}$ subunit sequence, or (3) interfere with the ability of the corresponding RNA transcript to be translated into a protein. Thus, a gene expression sequence would be operably linked to a human N-type calcium channel h$\alpha_{1B+SFVG}$ subunit nucleic acid sequence if the gene expression sequence were capable of effecting transcription of that human N-type calcium channel h$\alpha_{1B+SFVG}$ subunit nucleic acid sequence such that the resulting transcript might be translated into the desired protein or polypeptide.

The human N-type calcium channel h$\alpha_{1B+SFVG}$ subunit nucleic acid and the human N-type calcium channel h$\alpha_{1B+SFVG}$ subunit polypeptide (including the human N-type calcium channel h$\alpha_{1B+SFVG}$ subunit inhibitors described below) of the invention can be delivered to the eukaryotic or prokaryotic cell alone or in association with a vector. In its broadest sense, a "vector" is any vehicle capable of facilitating: (1) delivery of a human N-type calcium channel h$\alpha_{1B+SFVG}$ subunit nucleic acid or polypeptide to a target cell or (2) uptake of a human N-type calcium channel h$\alpha_{1B+SFVG}$ subunit nucleic acid or polypeptide by a target cell. Preferably, the vectors transport the human N-type calcium channel h$\alpha_{1B+SFVG}$ subunit nucleic acid or polypeptide into the target cell with reduced degradation relative to the extent of degradation that would result in the absence of the vector. Optionally, a "targeting ligand" can be attached to the vector to selectively deliver the vector to a cell which expresses on its surface the cognate receptor (e.g. a receptor, an antigen recognized by an antibody) for the targeting ligand. In this manner, the vector (containing a human N-type calcium channel h$\alpha_{1B+SFVG}$ subunit nucleic acid or a human N-type calcium channel h$\alpha_{1B+SFVG}$ subunit polypeptide) can be selectively delivered to a specific cell. In general, the vectors useful in the invention are divided into two classes: biological vectors and chemical/physical vectors. Biological vectors are more useful for delivery/uptake of human N-type calcium channel h$\alpha_{1B+SFVG}$ subunit nucleic acids to/by a target cell. Chemical/physical vectors are more useful for delivery/uptake of human N-type calcium channel h$\alpha_{1B+SFVG}$ subunit nucleic acids or human N-type calcium channel h$\alpha_{1B+SFVG}$ subunit proteins to/by a target cell.

Biological vectors include, but are not limited to, plasmids, phagemids, viruses, other vehicles derived from viral or bacterial sources that have been manipulated by the insertion or incorporation of the nucleic acid sequences of the invention, and free nucleic acid fragments which can be attached to the nucleic acid sequences of the invention. Viral vectors are a preferred type of biological vector and include, but are not limited to, nucleic acid sequences from the following viruses: retroviruses, such as Moloney murine leukemia virus; Harvey murine sarcoma virus; murine mammary tumor virus; Rous sarcoma virus; adenovirus; adeno-associated virus; SV40-type viruses; polyoma viruses; Epstein-Barr viruses; papilloma viruses; herpes virus; vaccinia virus; and polio virus. One can readily employ other vectors not named but known in the art.

Preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., "*Gene Transfer and Expression, A Laboratory Manual*," W. H. Freeman C.O., New York (1990) and Murry, E. J. Ed. "*Methods in Molecular Biology*," vol. 7, Humana Press, Inc., Clifton, N.J. (1991).

Another preferred virus for certain applications is the adeno-associated virus, a double-stranded DNA virus. The adeno-associated virus can be engineered to be replication-deficient and is capable of infecting a wide range of cell types and species. It further has advantages, such as heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a human N-type calcium channel h$\alpha_{1B+SFVG}$ subunit polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEFBOS plasmid containing the promoter of polypeptide Elongation Factor 1$\alpha$, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford- Perricaudet, which is defective for E1 and E3 proteins (*J. Clin. Invest.* 90:626–630, 1992).

In addition to the biological vectors, chemical/physical vectors may be used to deliver a human N-type calcium channel $h\alpha_{1B+SFVG}$ subunit nucleic acid or polypeptide to a target cell and facilitate uptake thereby. As used herein, a "chemical/physical vector" refers to a natural or synthetic molecule, other than those derived from bacteriological or viral sources, capable of delivering the isolated human N-type calcium channel $h\alpha_{1B+SFVG}$ subunit nucleic acid or polypeptide to a cell.

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vesicles which are useful as a delivery vector in vivo or in vitro. It has been shown that large unilamellar vesicles (LUV), which range in size from $0.2-4.0\mu$ can encapsulate large macromolecules. RNA, DNA, and intact virions can be encapsulated within the aqueous interior and be delivered to cells in a biologically active form (Fraley, et al., *Trends Biochem. Sci.*, v. 6, p. 77 (1981)). In order for a liposome to be an efficient nucleic acid transfer vector, one or more of the following characteristics should be present: (1) encapsulation of the nucleic acid of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular tissue by coupling the liposome to a specific ligand such as a monoclonal antibody, sugar, glycolipid, or protein. Ligands which may be useful for targeting a liposome to a particular cell will depend on the particular cell or tissue type. Additionally when the vector encapsulates a nucleic acid, the vector may be coupled to a nuclear targeting peptide, which will direct the human N-type calcium channel $h\alpha_{1B+SFVG}$ subunit nucleic acid to the nucleus of the host cell.

Liposomes are commercially available from Gibco BRL, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, V. 3, p. 235–241 (1985).

Other exemplary compositions that can be used to facilitate uptake by a target cell of the human N-type calcium channel $h\alpha_{1B+SFVG}$ subunit nucleic acids include calcium phosphate and other chemical mediators of intracellular transport, microinjection compositions, electroporation and homologous recombination compositions (e.g., for integrating a human N-type calcium channel $h\alpha_{1B+SFVG}$ subunit nucleic acid into a preselected location within a target cell chromosome).

The invention also embraces so-called expression kits, which allow the artisan to prepare a desired expression vector or vectors. Such expression kits include at least separate portions of the previously discussed coding sequences. Other components may be added, as desired, as long as the previously mentioned sequences, which are required, are included.

It will also be recognized that the invention embraces the use of the human N-type calcium channel $h\alpha_{1B+SFVG}$ subunit cDNA sequences in expression vectors, as well as to transfect host cells and cell lines, be these prokaryotic (e.g., *E. coli*), or eukaryotic (e.g., COS cells, yeast expression systems and recombinant baculovirus expression in insect cells). Especially useful are mammalian cells such as human, pig, goat, primate, etc. They may be of a wide variety of tissue types, and include primary cells and cell lines. Specific examples include neuronal cells including PC12 cells, Xenopus oocytes, bone marrow stem cells and embryonic stem cells. The expression vectors require that the pertinent sequence, i.e., those nucleic acids described supra, be operably linked to a promoter.

The invention also provides isolated human N-type calcium channel $h\alpha_{1B+SFVG}$ subunit polypeptides which include the amino acid sequence of SEQ ID NO:2, encoded by the human N-type calcium channel hciB SFVG subunit nucleic acids described above. The preferred human N-type calcium channel $h\alpha_{1B+SFVG}$ subunit polypeptide has the amino acid sequence of SEQ ID NO:4. Human N-type calcium channel $h\alpha_{1B+SFVG}$ subunit polypeptides also embrace alleles, functionally equivalent variants and analogs (those non-allelic polypeptides which vary in amino acid sequence from SEQ ID NO:4 by 1, 2, 3, 4, 5, or more amino acids) provided that such polypeptides include the amino acids of SEQ ID NO:2 and retain human N-type calcium channel $h\alpha_{1B+SFVG}$ subunit activity, and fragments of SEQ ID NO:4 which include SEQ ID NO:2. Non-functional variants also are embraced by the invention; these are useful as antagonists of calcium channel function, as negative controls in assays, and the like. Such alleles, variants, analogs and fragments are useful, for example, alone or as fusion proteins for a variety of purposes such as to generate antibodies, or as a component of an immunoassay.

Fragments of a polypeptide preferably are those fragments which retain a distinct functional capability of the human N-type calcium channel $h\alpha_{1B+SFVG}$ subunit polypeptide, in particular voltage regulated calcium influx. Other functional capabilities which can be retained in a fragment of a human N-type calcium channel $h\alpha_{1B+SFVG}$ subunit polypeptide include interaction with antibodies and interaction with other polypeptides (such as other subunits of the human N-type calcium channel). Those skilled in the art are well versed in methods for selecting fragments which retain a functional capability of the human N-type calcium channel $h\alpha_{1B+SFVG}$ subunit. Confirmation of the functional capability of the fragment can be carried out by synthesis of the fragment and testing of the capability according to standard methods. For example, to test the voltage regulated calcium influx of a human N-type calcium channel $h\alpha_{1B+SFVG}$ subunit fragment, one inserts or expresses the fragment in a cell in which calcium influx can be measured. Such methods, which are standard in the art, are described further in the examples.

The invention embraces variants of the human N-type calcium channel $h\alpha_{1B+SFVG}$ subunit polypeptides described above. As used herein, a "variant" of a human N-type calcium channel $h\alpha_{1B+SFVG}$ subunit polypeptide is a polypeptide which contains one or more modifications to the primary amino acid sequence of a human N-type calcium channel $h\alpha_{1B+SFVG}$ subunit polypeptide. Modifications which create a human N-type calcium channel $h\alpha_{1B+SFVG}$ SFVG subunit variant can be made to a human N-type calcium channel $h\alpha_{1B+SFVG}$ subunit polypeptide for a variety of reasons, including 1) to reduce or eliminate an activity of a human N-type calcium channel $h\alpha_{1B+SFVG}$ subunit polypeptide, such as voltage gated calcium influx; 2) to enhance a property of a human N-type calcium channel $h\alpha_{1B+SFVG}$ subunit polypeptide, such as protein stability in an expression system or the stability of protein-protein binding, 3) to provide a novel activity or property to a human N-type calcium channel $h\alpha_{1B+SFVG}$ subunit polypeptide, such as addition of an antigenic epitope or addition of a detectable moiety; or 4) to establish that an amino acid substitution does or does not affect voltage gated calcium influx. Modifications to a human $h\alpha_{1B+SFVG}$ calcium channel polypeptide are typically made to the nucleic acid which encodes the human N-type calcium channel $h\alpha_{1B+SFVG}$ subunit polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the human N-type calcium channel $h\alpha_{1B+SFVG}$ subunit amino acid sequence, but always including SEQ ID NO:2. One of skill in the art will be familiar with methods for predicting the effect on protein conformation of a change in protein sequence, and can thus "design" a variant human N-type calcium channel $h\alpha_{1B+SFVG}$ subunit according to known methods. One example of such a method is described by Dahiyat and Mayo in *Science* 278:82–87, 1997, whereby proteins can be designed de novo. The method can be applied to a known protein to vary a only a portion of the polypeptide sequence. By applying the computational methods of Dahiyat and Mayo, specific variants of a cancer associated antigen polypeptide can be proposed and tested to determine whether the variant retains a desired conformation.

Variants include human N-type calcium channel $h\alpha_{1B+SFVG}$ subunit polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a human N-type calcium channel $h\alpha_{1B+SFVG}$ subunit polypeptide by eliminating proteolysis by proteases in an expression system (e.g., dibasic amino acid residues in yeast expression systems in which KEX2 protease activity is present).

Mutations of a nucleic acid which encode a human N-type calcium channel $h\alpha_{1B+SFVG}$ subunit polypeptide preferably preserve the amino acid reading frame of the coding sequence, and preferably do not create regions in the nucleic acid which are likely to hybridize to form secondary structures, such as hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with a desired property. Further mutations can be made to variants (or to non-variant human N-type calcium channel $h\alpha_{1B+SFVG}$ subunit polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a human N-type calcium channel $h\alpha_{1B+SFVG}$ subunit gene or cDNA clone to enhance expression of the polypeptide.

The activity of variants of human N-type calcium channel $h\alpha_{1B+SFVG}$ subunit polypeptides can be tested by cloning the gene encoding the variant human N-type calcium channel $h\alpha_{1B+SFVG}$ subunit polypeptide into a bacterial or mammalian expression vector, introducing the vector into an appropriate host cell, expressing the variant human N-type calcium channel $h\alpha_{1B+SFVG}$ subunit polypeptide, and testing for a functional capability of the human N-type calcium channel $h\alpha_{1B+SFVG}$ subunit polypeptides as disclosed herein. For example, the variant human N-type calcium channel $h\alpha_{1B+SFVG}$ subunit polypeptide can be tested for ability to provide voltage regulated calcium influx, as set forth below in the examples. Preparation of other variant polypeptides may favor testing of other activities, as will be known to one of ordinary skill in the art.

The skilled artisan will also realize that conservative amino acid substitutions may be made in human N-type calcium channel $h\alpha_{1B+SFVG}$ subunit polypeptides to provide functionally equivalent variants of the foregoing polypeptides, i.e, variants which retain the functional capabilities of the human N-type calcium channel $h\alpha_{1B+SFVG}$ subunit polypeptides. As used herein, a "conservative amino acid substitution" refers to an amino acid substitution which does not alter the relative charge or size characteristics of the polypeptide in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the human N-type calcium channel $h\alpha_{1B+SFVG}$ subunit polypeptides include conservative amino acid substitutions of SEQ ID NO:4, but excluding the portion of the polypeptide consisting of SEQ ID NO:2 (SFVG). Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Conservative amino-acid substitutions in the amino acid sequence of human N-type calcium channel $h\alpha_{1B+SFVG}$ subunit polypeptide to produce functionally equivalent variants of human N-type calcium channel $h\alpha_{1B+SFVG}$ subunit polypeptides typically are made by alteration of the nucleic acid sequence encoding human N-type calcium channel $h\alpha_{1B+SFVG}$ subunit polypeptides (e.g., SEQ ID NO:3). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a human N-type calcium channel $h\alpha_{1B+SFVG}$ subunit polypeptide. Where amino acid substitutions are made to a small unique fragment of a human N-type calcium channel $h\alpha_{1B+SFVG}$ subunit polypeptide, such as a leucine zipper domain, the substitutions can be made by directly synthesizing the peptide. The activity of functionally equivalent fragments of human N-type calcium channel $h\alpha_{1B+SFVG}$ subunit polypeptides can be tested by cloning the gene encoding the altered human N-type calcium channel $h\alpha_{1B+SFVG}$ subunit polypeptide into a bacterial or mammalian expression vector, introducing the vector into an appropriate host cell, expressing the altered human N-type calcium channel h$\alpha_{1B+SFVG}$ subunit polypeptide, and testing for the ability of the human N-type calcium channel h$\alpha_{1B+SFVG}$ subunit polypeptide to transduce voltage regulated calcium influx. Peptides which are chemically synthesized can be tested directly for function.

A variety of methodologies well-known to the skilled practitioner can be utilized to obtain isolated human N-type calcium channel h$\alpha_{1B+SFVG}$ subunit molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating human N-type calcium channel h$\alpha_{1B+SFVG}$ subunit polypeptides. These include, but are not limited to, immunochromatography, HPLC, size-exclusion chromatography, ion-exchange chromatography and immune-affinity chromatography.

The invention as described herein has a number of uses, some of which are described elsewhere herein. For example, the invention permits isolation of the human N-type calcium channel h$\alpha_{1B+SFVG}$ subunit polypeptide molecules containing the amino acid sequence of SEQ ID NO:2 by e.g., expression of a recombinant nucleic acid to produce large quantities of polypeptide which may be isolated using standard protocols. As another example, the isolation of the human N-type calcium channel h$\alpha_{1B+SFVG}$ subunit gene makes it possible for the artisan to diagnose a disorder characterized by loss of expression of human N-type calcium channel h$\alpha_{1B+SFVG}$ subunit. These methods involve determining expression of the human N-type calcium channel h$\alpha_{1B+SFVG}$ subunit nucleic acid, and/or human N-type calcium channel h$\alpha_{1B+SFVG}$ subunit polypeptides derived therefrom. In the former situation, such determinations can be carried out via any standard nucleic acid determination assay, including the polymerase chain reaction, or assaying with labeled hybridization probes.

The invention also embraces agents which bind selectively to the human N-type calcium channel h$\alpha_{1B+SFVG}$ subunit (having or encoding SEQ ID NO:2) and agents which bind preferentially to the human N-type calcium channel h$\alpha_{1B+SFVG}$ subunit (having or encoding SEQ ID NO:2) as well as agents which bind to variants and fragments of the polypeptides and nucleic acids as described herein. Selective binding means that the agent binds to the human N-type calcium channel h$\alpha_{1B+SFVG}$ subunit but not to human N-type calcium channel non-h$\alpha_{1B+SFVG}$ subunits (i.e., those subunits which do not have or encode SEQ ID NO:2). Preferential binding means that the agent binds more to the human N-type calcium channel h$\alpha_{1B+SFVG}$ subunit than to human N-type calcium channel h$\alpha_{1B+SFVG}$ subunit, e.g., the agent binds with greater affinity or avidity to the human N-type calcium channel h$\alpha_{1B+SFVG}$ subunit having or encoding SEQ ID NO:2. The agents include polypeptides which bind to human N-type calcium channel h$\alpha_{1B+SFVG}$ subunit, and antisense nucleic acids, both of which are described in greater detail below. The agents can inhibit or increase human N-type calcium channel h$\alpha_{1B+SFVG}$ subunit activity (antagonists and agonists, respectively).

Some of the agents are inhibitors. A human N-type calcium channel h$\alpha_{1B+SFVG}$ subunit inhibitor is an agent that inhibits human N-type calcium channel h$\alpha_{1B+SFVG}$ subunit mediated voltage gated calcium influx. Human N-type calcium channel h$\alpha_{1B+SFVG}$ subunit inhibitors also include dominant negative peptides and known N-type calcium channel inhibitors including the ω-conotoxin peptides and derivative thereof such as ziconotide (SNX-111). Small organic molecule calcium channel inhibitors, such as fluspirilene, NNC 09-0026(−)-trans-1-butyl-4-(4-dimethylaminophenyl)-3-[(4-trifluoromethyl-phenoxy) methyl]piperidinedihydrochloride); SB 201823-A (4-[2-(3, 4-dichlorophenoxy)ethyl]-1-pentyl piperidinehydrochloride); NS 649 (2-amino-1-(2,5-dimethoxyphenyl)-5-trifluoromethyl benzimidazole); CNS 1237 (N-acenaphthyl-N'-4-methoxynaphth-1-yl guanidine) and riluzole may also exhibit specificity for the human N-type calcium channel h$\alpha_{1B+SFVG}$ subunit.

Calcium influx assays can be performed to screen and/or determine whether a human N-type calcium channel h$\alpha_{1B+SFVG}$ subunit inhibitor has the ability to inhibit human N-type calcium channel h$\alpha_{1B+SFVG}$ subunit activity, and whether the inhibition is selective. As used herein, "inhibit" refers to inhibiting by at least 10% voltage gated calcium influx, preferably inhibiting by at least 25% voltage gated calcium influx, and more preferably inhibiting by at least 40% voltage gated calcium influx as measured by any of the methods well known in the art. An exemplary assay of voltage gated calcium influx is described below in the Examples.

Inhibitors may selectively inhibit h$\alpha_{1B+SFVG}$ based on the state of depolarization of the membrane with which the h$\alpha_{1B+SFVG}$ is associated. It is well known that certain compounds preferentially bind to voltage-gated calcium channels at particular voltages. For example, dihydropyridine compounds preferentially bind to L-type voltage-gated calcium channels when the membrane is depolarized. Bean (*Proc. Nat'l. Acad. Sci.* 81:6388, 1984) described the binding of nitrendipine to cardiac L-type channels only when the membrane is depolarized. Similar results have been found for nimodipine action in sensory neurons (McCarthy & TanPiengco, *J. Neurosci.* 12:2225, 1992).

Activators of human N-type calcium channel h$\alpha_{1B+SFVG}$ activity also are enhanced by the invention. Activators may be identified and/or tested using methods described above for inhibitors. The SFVG site is located in a portion of the h$\alpha_{1B+SFVG}$ channel which is important for voltage dependent gating of $Ca^{2+}$ influx. Therefore, in screening for modulators of h$\alpha_{1B+SFVG}$, including inhibitors and activators (i.e. antagonists and agonists), it is preferred that compounds (e.g. libraries of potential channel inhibitors) are tested for modulation of h$\alpha_{1B+SFVG}$ activity at a variety of voltages which cause partial or complete membrane depolarization, or hyperpolarization. These assays are conducted according to standard procedures of testing calcium channel function (e.g. patch clamping, fluorescent $Ca^{2+}$ influx assays) which require no more than routine experimentation. Using such methods, modulators of h$\alpha_{1B+SFVG}$ activity which are active at particular voltages (e.g. complete membrane depolarization) can be identified. Such compounds are useful for selectively modulating calcium channel activity in conditions which may display voltage dependence. For example, following a stroke membranes are depolarized and such compounds may be active in selectively blocking calcium channel activity for treatment of stroke. Other uses will be apparent to one of ordinary skill in the art.

In one embodiment the human N-type calcium channel h$\alpha_{1B+SFVG}$ subunit inhibitor is an antisense oligonucleotide that selectively binds to a human N-type calcium channel $h\alpha_{1B+SFVG}$ subunit nucleic acid molecule, to reduce the expression of human N-type calcium channel $h\alpha_{1B+SFVG}$ subunit in a cell. This is desirable in virtually any medical condition wherein a reduction of human N-type calcium channel $h\alpha_{1B+SFVG}$ subunit activity is desirable, e.g., voltage gated calcium influx.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840–844, 1996). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which polypeptides are not expected to bind. Thus, the present invention also provides for antisense oligonucleotides which are complementary to allelic or homologous cDNAs and genomic DNAs corresponding to human N-type calcium channel $h\alpha_{1B+SFVG}$ subunit nucleic acid containing SEQ ID NO:1.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides arc covalently linked via a synthetic internueleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkyiphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding human N-type calcium channel $h\alpha_{1B+SFVG}$ subunit polypeptides, together with pharmaceutically acceptable carriers.

Antisense oligonucleotides may be administered as part of a pharmaceutical composition. Such a pharmaceutical composition may include the antisense oligonucleotides in combination with any standard pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The characteristics of the carrier will depend on the route of administration. Pharmaceutically acceptable carriers include diluents, fillers, salts, buffers, stabilizers, solubilizers, and other materials which are well known in the art.

Agents which bind human N-type calcium channel $h\alpha_{1B+SFVG}$ subunit also include binding peptides which bind to the human N-type calcium channel $h\alpha_{1B+SFVG}$ subunit and complexes containing the human N-type calcium channel $h\alpha_{1B+SFVG}$ subunit. When the binding polypeptides are inhibitors, the polypeptides bind to and inhibit the activity of human N-type calcium channel $h\alpha_{1B+SFVG}$ subunit. To determine whether a human N-type calcium channel $h\alpha_{1B+SFVG}$ subunit binding peptide binds to human N-type calcium channel $h\alpha_{1B+SFVG}$ subunit any known binding assay may be employed. For example, the peptide may be immobilized on a surface and then contacted with a labeled human N-type calcium channel $h\alpha_{1B+SFVG}$ subunit. The amount of human N-type calcium channel $h\alpha_{1B+SFVG}$ subunit which interacts with the human N-type calcium channel $h\alpha_{1B+SFVG}$ subunit binding peptide or the amount which does not bind to the human N-type calcium channel h$\alpha_{1B+SFVG}$ subunit binding peptide may then be quantitated to determine whether the human N-type calcium channel h$\alpha_{1B+SFVG}$ subunit binding peptide binds to human N-type calcium channel h$\alpha_{1B+SFVG}$ subunit. Further, the binding of a human N-type calcium channel h$\alpha_{1B+SFVG}$ subunit and a human N-type calcium channel non-h$\alpha_{1B+SFVG}$ subunit can be compared to determine if the binding peptide binds selectively or preferentially.

The human N-type calcium channel h$\alpha_{1B+SFVG}$ subunit binding peptides include peptides of numerous size and type that bind selectively or preferentially to human N-type calcium channel h$\alpha_{1B+SFVG}$ subunit polypeptides, and complexes of both human N-type calcium channel h$\alpha_{1B+SFVG}$ subunit polypeptides and their binding partners. These peptides may be derived from a variety of sources. For example, binding peptides include known N-type calcium channel inhibitors such as the ω-conotoxin peptides GVIA SEQ ID NO: 11 (from *C. geographus*) and MVIIA SEQ ID NO: 12 (from *C. magus*). Other such human N-type calcium channel h$\alpha_{1B+SFVG}$ subunit binding peptides can be provided by modifying the foregoing peptides or by screening degenerate peptide libraries which can be readily prepared in solution, in immobilized form or as phage display libraries. Combinatorial libraries also can be synthesized of peptides containing one or more amino acids. Libraries further can be synthesized of peptides and non-peptide synthetic moieties. Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the human N-type calcium channel h$\alpha_{1B+SFVG}$ subunit polypeptide. This process can be repeated through several cycles of reselection of phage that bind to the human N-type calcium channel h$\alpha_{1B+SFVG}$ subunit polypeptide. Repeated rounds lead to enrichment of phage bearing particular sequences. DNA sequence analysis can be conducted to identify the sequences of the expressed polypeptides. The minimal linear portion of the sequence that binds to the human N-type calcium channel h$\alpha_{1B+SFVG}$ subunit polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the human N-type calcium channel h$\alpha_{1B+SFVG}$ subunit polypeptides. Thus, the human N-type calcium channel h$\alpha_{1B+SFVG}$ subunit polypeptides of the invention, or a fragment thereof, can be used to screen peptide libraries, including phage display libraries, to identify and select peptide binding partners of the human N-type calcium channel h$\alpha_{1B+SFVG}$ polypeptides of the invention. Such molecules can be used, as described, for screening assays, for purification protocols, for interfering directly with the functioning of human N-type calcium channel h$\alpha_{1B+SFVG}$ subunit and for other purposes that will be apparent to those of ordinary skill in the art.

Peptides may easily be synthesized or produced by recombinant means by those of skill in the art. Using routine procedures known to those of ordinary skill in the art, one can determine whether a peptide which binds to human N-type calcium channel h$\alpha_{1B+SFVG}$ subunit is useful according to the invention by determining whether the peptide is one which inhibits the activity of human N-type calcium channel h$\alpha_{1B+SFVG}$ subunit in a voltage gated calcium influx assay, as discussed above.

The human N-type calcium channel h$\alpha_{1B+SFVG}$ subunit binding peptide agent may also be an antibody or a functionally active antibody fragment. Antibodies are well known to those of ordinary skill in the science of immunology. As used herein, the term "antibody" means not only intact antibody molecules but also fragments of antibody molecules retaining human N-type calcium channel h$\alpha_{1B+SFVG}$ subunit binding ability. Such fragments are also well known in the art and are regularly employed both in vitro and in vivo. In particular, as used herein, the term "antibody" means not only intact immunoglobulin molecules but also the well-known active fragments $F(ab')_2$, and Fab. $F(ab')_2$, and Fab fragments which lack the Fc fragment of intact antibody, clear more rapidly from the circulation, and may have less non-specific tissue binding of an intact antibody (Wahl et al., *J. Nucl. Med.* 24:316–325 (1983)).

In one set of embodiments, the antibody useful according to the methods of the present invention is an intact, fully human anti-human N-type calcium channel h$\alpha_{1B+SFVG}$ subunit monoclonal antibody in an isolated form or in a pharmaceutical preparation. The following is a description of a method for developing a monoclonal antibody that interacts with and inhibits the activity of human N-type calcium channel h$\alpha_{1B+SFVG}$ subunit. The description is exemplary and is provided for illustrative purposes only.

Murine monoclonal antibodies may be made by any of the methods known in the art utilizing human N-type calcium channel h$\alpha_{1B+SFVG}$ subunit, or a fragment thereof, as an immunogen provided that the channel or fragment contains the amino acid sequence of SEQ ID NO:2.

Human monoclonal antibodies may be made by any of the methods known in the art, such as those disclosed in U.S. Pat. No. 5,567,610, issued to Borrebaeck et al., U.S. Pat. No. 5,565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51–63 (Marcel Dekker, Inc, new York, 1987), and Boerner el al., *J. Immunol.*, 147: 86–95 (1991). In addition to the conventional methods for preparing human monoclonal antibodies, such antibodies may also be prepared by immunizing transgenic animals that are capable of producing human antibodies (e.g., Jakobovits et al., *Proc. Nat'l. Acad. Sci. USA*, 90: 2551 (1993), Jakobovits et al., *Nature*, 362: 255–258 (1993), Bruggermann et al., *Year in Immuno.*, 7:33 (1993) and U.S. Pat. No. 5,569,825 issued to Lonberg).

Alternatively the antibody may be a polyclonal antibody specific for human N-type calcium channel h$\alpha_{1B+SFVG}$ subunit which inhibits human N-type calcium channel h$\alpha_{1B+SFVG}$ subunit activity. The preparation and use of polyclonal antibodies is known to one of ordinary skill in the art.

Significantly, as is well known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab')$_2$" fragment, retains both of the antigen binding sites of the intact antibody. Similarly, an antibody from which the Fc region has been enzymatically cleaved, or which has been produced without the Fc region, designated an "Fab" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to antigen epitopes.

The sequences of the antigen-binding Fab' portion of the anti-human N-type calcium channel h$\alpha_{1B+SFVG}$ subunit monoclonal antibodies identified as being useful according to the invention in the assays provided above, as well as the relevant FR and CDR regions, can be determined using amino acid sequencing methods that are routine in the art. It is well established that non-CDR regions of a mammalian antibody may be replaced with corresponding regions of non-specific or hetero-specific antibodies while retaining the epitope specificity of the original antibody. This technique is useful for the development and use of "humanized" antibodies in which non-human CDRs are covalently joined to human FR and/or Fc/pFc' regions to produce a functional antibody. Techniques to humanize antibodies are particularly useful when non-human animal (e.g., murine) antibodies which inhibit human N-type calcium channel h$\alpha_{1B+SFVG}$ subunit activity are identified. These non-human animal antibodies can be humanized for use in the treatment of a human subject in the methods according to the invention. An example of a method for humanizing a murine antibody is provided in PCT International Publication No. WO 92/04381 which teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, and Fab fragments of an anti-human N-type calcium channel h$\alpha_{1B+SFVG}$ subunit monoclonal antibody; chimeric antibodies in which the Fc and/or FR and/or CDR1 and/or CDR2 and/or light chain CDR3 regions of an anti-human N-type calcium channel h$\alpha_{1B+SFVG}$ subunit antibody have been replaced by homologous human or non-human sequences; chimeric F(ab')$_2$ fragment antibodies in which the FR and/or CDR1 and/or CDR2 and/or light chain CDR3 regions of an anti-human N-type calcium channel h$\alpha_{1B+SFVG}$ subunit antibody have been replaced by homologous human or non-human sequences; and chimeric Fab fragment antibodies in which the FR and/or CDR1 and/or CDR2 and/or light chain CDR3 regions have been replaced by homologous human or non-human sequences. Thus, those skilled in the art may alter an anti-human N-type calcium channel h$\alpha_{1B+SFVG}$ subunit antibody by the construction of CDR grafted or chimeric antibodies or antibody fragments containing, all or part thereof, of the disclosed heavy and light chain V-region CDR amino acid sequences (Jones et al., *Nature* 321:522, 1986; Verhoeyen et al., *Science* 39:1534, 1988 and Tempest et al., *Bio/Technology* 9:266, 1991), without destroying the specificity of the antibodies for human N-type calcium channel h$\alpha_{1B+SFVG}$ subunit. Such CDR grafted or chimeric antibodies or antibody fragments can be effective in inhibiting human N-type calcium channel h$\alpha_{1B+SFVG}$ subunit activity in animals (e.g. primates) and humans.

In preferred embodiments, the chimeric antibodies of the invention are fully human monoclonal antibodies. As noted above, such chimeric antibodies may be produced in which some or all of the FR regions of human N-type calcium channel h$\alpha_{1B+SFVG}$ subunit have been replaced by other homologous human FR regions. In addition, the Fc portions may be replaced so as to produce IgA or IgM as well as IgG antibodies bearing some or all of the CDRs of the anti-human N-type calcium channel h$\alpha_{1B+SFVG}$ subunit antibody. Of particular importance is the inclusion of the anti-human N-type calcium channel h$\alpha_{1B+SFVG}$ subunit heavy chain CDR3 region and, to a lesser extent, the other CDRs of anti-human N-type calcium channel h$\alpha_{1B+SFVG}$ subunit antibodies. Such fully human chimeric antibodies will have particular utility in that they will not evoke an immune response against the antibody itself.

It is also possible, in accordance with the present invention, to produce chimeric antibodies including non-human sequences. Thus, one may use, for example, murine, ovine, equine, bovine or other mammalian Fc or FR sequences to replace some or all of the Fc or FR regions of the anti-human N-type calcium channel h$\alpha_{1B+SFVG}$ subunit antibody. Some of the CDRs may be replaced as well. Again, however, it is preferred that at least the heavy chain CDR3 region of the anti-human N-type calcium channel h$\alpha_{1B+SFVG}$ subunit antibody be included in such chimeric antibodies and, to a lesser extent, it is also preferred that some or all of the other CDRs of anti-human N-type calcium channel h$\alpha_{1B+SFVG}$ subunit be included. Such chimeric antibodies bearing non-human immunoglobulin sequences admixed with the CDRs of the human anti-human N-type calcium channel h$\alpha_{1B+SFVG}$ subunit monoclonal antibody are not preferred for use in humans and are particularly not preferred for extended use because they may evoke an immune response against the non-human sequences. They may, of course, be used for brief periods or in immunosuppressed individuals but, again, fully human antibodies are preferred. Because, however, such antibodies may be used for brief periods or in immunosuppressed subjects, chimeric antibodies bearing non-human mammalian Fc and FR sequences but including at least the anti-human N-type calcium channel hα$_{1B+SFVG}$ subunit heavy chain CDR3 are contemplated as alternative embodiments of the present invention.

For inoculation or prophylactic uses, the antibodies of the present invention are preferably intact antibody molecules including the Fc region. Such intact antibodies will have longer half-lives than smaller fragment antibodies (e.g. Fab) and are more suitable for intravenous, intraperitoneal, intramuscular, intracavity, subcutaneous, or transdermal administration.

Fab fragments, including chimeric Fab fragments, are preferred in methods in which the antibodies of the invention are administered directly to a local tissue environment. For example, the Fab fragments are preferred when the antibody of the invention is administered directly to the brain. Fabs offer several advantages over F(ab')$_2$ and whole immunoglobulin molecules for this therapeutic modality. First, because Fabs have only one binding site for their cognate antigen, the formation of immune complexes is precluded whereas such complexes can be generated when bivalent F(ab')$_2$ s and whole immunoglobulin molecules encounter their target antigen. This is of some importance because immune complex deposition in tissues can produce adverse inflammatory reactions. Second, because Fabs lack an Fc region they cannot trigger adverse inflammatory reactions that are activated by Fc, such as activation of the complement cascade. Third, the tissue penetration of the small Fab molecule is likely to be much better than that of the larger whole antibody. Fourth, Fabs can be produced easily and inexpensively in bacteria, such as *E. coli*, whereas whole immunoglobulin antibody molecules require mammalian cells for their production in useful amounts. Production of Fabs in *E. coli* makes it possible to produce these antibody fragments in large fermenters which are less expensive than cell culture-derived products.

Smaller antibody fragments and small binding peptides having binding specificity for the human N-type calcium channel hα$_{1B+SFVG}$ subunit which can be used to inhibit human N-type calcium channel hα$_{1B+SFVG}$ subunit activity also are embraced within the present invention. For example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated VH single domain, also have been reported (see, for example, Ward et al., *Nature* 341:644–646 (1989)).

According to the invention human N-type calcium channel hα$_{1B+SFVG}$ subunit inhibitors also include "dominant negative" polypeptides derived from SEQ ID NO:4. A dominant negative polypeptide is an inactive variant of a polypeptide, which, by interacting with the cellular machinery, displaces an active polypeptide from its interaction with the cellular machinery or competes with the active polypeptide, thereby reducing the effect of the active polypeptide. For example, a dominant negative receptor which binds a ligand but does not transmit a signal in response to binding of the ligand can reduce the biological effect of expression of the ligand. Likewise, a dominant negative human N-type calcium channel hα$_{1B+SFVG}$ subunit of an active complex (e.g. N-type calcium channel) can interact with the complex but prevent the activity of the complex (e.g. voltage gated calcium influx).

The end result of the expression of a dominant negative human N-type calcium channel hα$_{1B+SFVG}$ subunit polypeptide of the invention in a cell is a reduction in voltage gated calcium influx. One of ordinary skill in the art can assess the potential for a dominant negative variant of a human N-type calcium channel hα$_{1B+SFVG}$ subunit polypeptide, and using standard mutagenesis techniques to create one or more dominant negative variant polypeptides. For example, given the teachings contained herein of a human N-type calcium channel hα$_{1B+SFVG}$ subunit polypeptide, one of ordinary skill in the art can modify the sequence of the human N-type calcium channel hα$_{1B+SFVG}$ subunit polypeptide by site-specific mutagenesis, scanning mutagenesis, partial gene deletion or truncation, and the like. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in human N-type calcium channel hα$_{1B+SFVG}$ subunit activity (e.g.,voltage gated calcium influx) and/or for retention of such an activity. Other similar methods for creating and testing dominant negative variants of a human N-type calcium channel hα$_{1B+SFVG}$ subunit polypeptide will be apparent to one of ordinary skill in the art.

Each of the compositions of the invention is useful for a variety of therapeutic and non-therapeutic purposes. For example, the human N-type calcium channel hα$_{1B+SFVG}$ subunit nucleic acids of the invention are useful as oligonucleotide probes. Such oligonucleotide probes can be used herein to identify genomic or cDNA library clones possessing an identical or substantially similar nucleic acid sequence. A suitable oligonucleotide or set of oligonucleotides, which is capable of hybridizing under stringent hybridization conditions to the desired sequence, a variant or fragment thereof, or an anti-sense complement of such an oligonucleotide or set of oligonucleotides, can be synthesized by means well known in the art (see, for example, *Synthesis and Application of DNA and RNA*, S. A. Narang, ed., 1987, Academic Press, San Diego, Calif.) and employed as a probe to identify and isolate the desired sequence, variant or fragment thereof by techniques known in the art. Techniques of nucleic acid hybridization and clone identification are disclosed by Sambrook, et al., *Molecular Cloning, A Laboratory Manual*, 2d ed., Cold Spring Harbor Laboratory Press, Plainview, N.Y. (1989), and by Hames, B. D., et al., in *Nucleic Acid Hybridization, A Practical Approach*, IRL Press, Washington, D.C. (1985). To facilitate the detection of a desired nucleic acid sequence, or variant or fragment thereof, whether for cloning purposes or for the mere detection of the presence of the sequence, the above-described probes may be labeled with a detectable group. Such a detectable group may be any material having a detectable physical or chemical property. Such materials have been well-developed in the field of nucleic acid hybridization and, in general, most any label useful in such methods can be applied to the present invention. Particularly useful are radioactive labels. Any radioactive label may be employed which provides for an adequate signal and has a sufficient half-life. If single stranded, the oligonucleotide may be radioactively labeled using kinase reactions. Alternatively, oligonucleotides are also useful as nucleic acid hybridization probes when labeled with a non-radioactive marker such as biotin, an enzyme or a fluorescent group. See, for example, Leary, J. J., et al., *Proc. Natl. Acad. Sci.* (*USA*) 80:4045 (1983); Renz, M. et al., *Nucl. Acids Res.* 12:3435 (1984); and Renz, M., *EMBO J.* 6:817 (1983).

Additionally, complements of the human N-type calcium channel hα$_{1B+SFVG}$ subunit nucleic acids can be useful as antisense oligonucleotides, e.g., by delivering the antisense oligonucleotide to an animal to induce a human N-type calcium channel h$\alpha_{1B+SFVG}$ subunit "knockout" phenotype. The administration of antisense RNA probes to block gene expression is discussed in Lichtenstein, C., *Nature* 333:801–802 (1988).

Alternatively, the human N-type calcium channel h$\alpha_{1B+SFVG}$ subunit nucleic acid of the invention can be used to prepare a non-human transgenic animal. A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Transgenic animals having a particular property associated with a particular disease can be used to study the affects of a variety of drugs and treatment methods on the disease, and thus serve as genetic models for the study of a number of human diseases. The invention, therefore, contemplates the use of human N-type calcium channel h$\alpha_{1B+SFVG}$ subunit knockout and transgenic animals as models for the study of disorders involving voltage gated calcium influx.

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division. See e.g., Brinster et al., *Proc. Nat. Acad. Sci. USA*, 82: 4438 (1985); Brinster et al., cell 27: 223 (1981); Costantini et al., *Nature* 294: 982 (1981); Harpers et al., *Nature* 293: 540 (1981); Wagner et al., *Proc. Nat. Acad. Sci. USA* 78:5016 (1981); Gordon et al., *Proc. Nat. Acad. Sci. USA* 73: 1260 (1976). The fertilized egg is then implanted into the uterus of the recipient female and allowed to develop into an animal.

An alternative method for producing transgenic animals involves the incorporation of the desired gene sequence into a virus which is capable of affecting the cells of a host animal. See e.g., Elbrecht et al., *Molec. Cell. Biol.* 7: 1276 (1987); Lacey et al., *Nature* 322: 609 (1986); Leopol et al., *Cell* 51: 885 (1987). Embryos can be infected with viruses, especially retroviruses, modified to carry the nucleotide sequences of the invention which encode human N-type calcium channel h$\alpha_{1B+SFVG}$ subunit proteins or sequences which disrupt the native human N-type calcium channel h$\alpha_{1B+SFVG}$ subunit gene to produce a knockout animal.

Another method for producing transgenic animals involves the injection of pluripotent embryonic stem cells into a blastocyst of a developing embryo. Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. See e.g., Robertson et al., *Cold Spring Harbor Conference Cell Proliferation* 10: 647 (1983); Bradley et al., *Nature* 309: 255 (1984); Wagner et al., *Cold Spring Harbor Symposium Quantitative Biology* 50: 691(1985).

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia*, 47: 897–905(1991). Other procedures for introduction of DNA into tissues of animals are described in U.S. Pat. No. 4,945,050 (Sandford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer et al., *Cell*, 63:1099–1112 (1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, *Teratocarcinomas and Embryonic Stem Cells, A Practical Approach*, E. J. Robertson, ed., IRL Press (1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. Capecchi, *Science*, 244: 1288–1292 (1989). Methods for positive selection of the recombination event (e.g., neo resistance) and dual positive-negative selection (e.g., neo resistance and gancyclovir resistance) and the subsequent identification of the desired clones by PCR have been described by Capecchi, supra and Joyner et al., *Nature*, 338: 153–156 (1989). The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene.

Procedures for the production of non-rodent mammals and other animals have been discussed by others. See Houdebine and Chourrout, supra; Pursel et al., Science 244: 1281–1288 (1989); and Simms et al., *Bio/Technology*, 6: 179–183 (1988).

Inactivation or replacement of the endogenous N-type calcium channel h$\alpha_{1B+SFVG}$ subunit gene can be achieved by a homologous recombination system using embryonic stem cells. The resultant transgenic non-human mammals (preferably primates) having a knockout N-type calcium channel h$\alpha_{1B+SFVG}$ subunit characteristic may be made transgenic for the human N-type calcium channel h$\alpha_{1B+SFVG}$ subunit and used as a model for screening compounds as modulators (agonists or antagonists/inhibitors) of the human N-type calcium channel h$\alpha_{1B+SFVG}$ subunit. In this manner, such therapeutic drugs can be identified.

Additionally, a normal or mutant version of human N-type calcium channel h$\alpha_{1B+SFVG}$ subunit can be inserted into the mouse (or the animal) germ line to produce transgenic animals which constitutively or inducibly express the normal or mutant form of human N-type calcium channel h$\alpha_{1B+SFVG}$ subunit. These animals are useful in studies to define the role and function of human N-type calcium channel h$\alpha_{1B+SFVG}$ subunit in cells. These studies are particularly useful in animals, which do not normally express human N-type calcium channel h$\alpha_{1B+SFVG}$ subunit, such as non-primates.

A human N-type calcium channel h$\alpha_{1B+SFVG}$ subunit polypeptide, or a fragment thereof, also can be used to isolate human N-type calcium channel h$\alpha_{1B+SFVG}$ subunit native binding partners, including, e.g., the N-type calcium channel. Isolation of such binding partners may be performed according to well-known methods. For example, isolated human N-type calcium channel h$\alpha_{1B+SFVG}$ subunit polypeptides can be attached to a substrate (e.g., chromatographic media, such as polystyrene beads, or a filter), and then a solution suspected of containing the N-type calcium channel may be applied to the substrate. If a N-type calcium channel which can interact with human N-type calcium channel h$\alpha_{1B+SFVG}$ subunit polypeptides is present in the solution, then it will bind to the substrate-bound human N-type calcium channel h$\alpha_{1B+SFVG}$ subunit polypeptide. The N-type calcium channel then may be isolated. Other polypeptides which are binding partners for human N-type calcium channel h$\alpha_{1B+SFVG}$ subunit may be isolated by similar methods without undue experimentation.

The compositions of the invention are also useful for therapeutic purposes. Accordingly the invention encompasses a method for inhibiting human N-type calcium channel h$\alpha_{1B+SFVG}$ subunit activity in a mammalian cell. The invention further provides methods for reducing or increasing human N-type calcium channel h$\alpha_{1B+SFVG}$ subunit activity in a cell. In one embodiment, the method involves contacting the mammalian cell with an amount of a human N-type calcium channel h$\alpha_{1B+SFVG}$ subunit inhibitor effective to inhibit voltage gated calcium influx in the mammalian cell. Such methods are useful in vitro for altering voltage gated calcium influx for the purpose of, for example, elucidating the mechanisms involved in stroke, pain, e.g., neuropathic pain, and traumatic brain injury and for restoring the voltage gated calcium influx in a cell having a defective human N-type calcium channel h$\alpha_{1B+SFVG}$ subunit. In vivo, such methods are useful, for example, for reducing N-type voltage gated calcium influx, e.g., to treat stroke, pain, e.g., neuropathic pain, traumatic brain injury, or any condition in which human N-type calcium channel h$\alpha_{1B+SFVG}$ subunit activity is elevated.

An amount of a human N-type calcium channel h$\alpha_{1B+SFVG}$ subunit inhibitor which is effective to inhibit voltage gated calcium influx in the mammalian cell is an amount which is sufficient to reduce voltage gated calcium influx by at least 10%, preferably at least 20%, more preferably 30% and still more preferably 40%. An amount of a human N-type calcium channel h$\alpha_{1B+SFVG}$ subunit which is effective to increase voltage gated calcium influx in the mammalian cell is an amount which is sufficient to increase voltage gated calcium influx by at least 10%, preferably at least 20%, more preferably 30% and still more preferably 40%. Such alterations in voltage gated calcium influx can be measured by the assays described herein.

As described above with respect to inhibitors, modulators of h$\alpha_{1B+SFVG}$ may selectively inhibit or increase h$\alpha_{1B+SFVG}$ function based on the state of depolarization of the membrane with which the h$\alpha_{1B+SFVG}$ is associated. Therefore, in screening for modulators of h$\alpha_{1B+SFVG}$, it is preferred that compounds (e.g. synthetic combinatorial libraries, natural products, peptide libraries, etc.) are tested for modulation of h$\alpha_{1B+SFVG}$ activity at a variety of voltages which cause partial or complete membrane depolarization, or hyperpolarization. These assays are conducted according to standard procedures of testing calcium channel function (e.g. patch clamping, fluorescent $Ca^{2+}$ influx assays) which require no more than routine experimentation. Using such methods, modulators of h$\alpha_{1B+SFVG}$ activity which are active at particular voltages (e.g. complete membrane depolarization) can be identified. Such compounds are useful for selectively modulating calcium channel activity in conditions which may display voltage dependence.

The invention also encompasses a method for increasing human N-type calcium channel h$\alpha_{1B+SFVG}$ subunit expression in a cell or subject. It is desirable to increase human N-type calcium channel h$\alpha_{1B+SFVG}$ subunit in a subject that has a disorder characterized by a deficiency in voltage gated calcium influx. The amount of human N-type calcium channel h$\alpha_{1B+SFVG}$ subunit can be increased in such cell or subject by contacting the cell with, or administering to the subject, a human N-type calcium channel h$\alpha_{1B+SFVG}$ subunit nucleic acid or a human N-type calcium channel h$\alpha_{1B+SFVG}$ subunit polypeptide of the invention to the subject in an amount effective to increase voltage gated calcium influx in the cell or the subject. An increase in human N-type calcium channel h$\alpha_{1B+SFVG}$ subunit activity can be measured by the assays described herein, e.g., assays of calcium influx.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus, retroviruses, herpes virus, and targeted liposomes also is contemplated according to the invention.

The preparations of the invention are administered in effective amounts. An effective amount is that amount of a pharmaceutical preparation that alone, or together with further doses, produces the desired response. In the case of treating a condition characterized by aberrant voltage gated calcium influx, the desired response is reducing or increasing calcium influx to a level which is within a normal range. Preferably, the change in calcium influx produces a detectable reduction in a physiological function related to the condition, e.g, a reduction in neurotoxicity following stroke. The responses can be monitored by routine methods. In the case of a condition where an increase in voltage gated calcium influx is desired, an effective amount is that amount necessary to increase said influx in the target tissue. The converse is the case when a reduction in influx is desired. An increase or decrease in neurotransmitter release also could be measured to monitor the response.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. It is preferred generally that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Generally, doses of active compounds would be from about 0.01 mg/kg per day to 1000 mg/kg per day. It is expected that doses ranging from 50–500 mg/kg will be suitable and in one or several administrations per day. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compound, although fewer doses typically will be given when compounds are prepared as slow release or sustained release medications.

When administered, the pharmaceutical preparations of the invention are applied in pharmaceutically-acceptable amounts and in pharmaceutically-acceptably compositions. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The human N-type calcium channel $h\alpha_{1B+SFVG}$ subunit inhibitors or human N-type calcium channel $h\alpha_{1B+SFVG}$ subunit nucleic acids and polypeptides useful according to the invention may be combined, optionally, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; and phosphoric acid in a salt.

The pharmaceutical compositions also may contain, optionally, suitable preservatives, such as: benzalkonium chloride; chlorobutanol; parabens and thimerosal.

A variety of administration routes are available. The particular mode selected will depend, of course, upon the particular compound selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intrathecal, intramuscular, or infusion. Intravenous or intramuscular routes are not particularly suitable for long-term therapy and prophylaxis.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous preparation of the human N-type calcium channel $h\alpha_{1B+SFVG}$ subunit inhibitor or human N-type calcium channel $h\alpha_{1B+SFVG}$ subunit nucleic acids and polypeptides, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or di-glycerides. In addition, fatty acids such as oleic acid may be used in the preparation of injectables. Carrier formulation suitable for oral, subcutaneous, intravenous, intrathecal, intramuscular, etc. administrations can be found in Remington's Pharmaceutical Sciences, Mack Publishing Co., Easton, Pa.

Other delivery systems can include time-release, delayed release or sustained release delivery systems such as the biological/chemical vectors is discussed above. Such systems can avoid repeated administrations of the active compound, increasing convenience to the subject and the physician. Many types of release delivery systems are available and known to those of ordinary skill in the art. Use of a long-term sustained release implant may be desirable. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The invention further provides efficient methods of identifying pharmacological agents or lead compounds for agents useful in the treatment of conditions associated with aberrant voltage gated cell calcium influx mediated by human N-type calcium channel $h\alpha_{1B+SFVG}$ subunit and the compounds and agents so identified. Generally, the screening methods involve assaying for compounds which inhibit or enhance voltage gated calcium influx through human N-type calcium channels. Such methods are adaptable to automated, high throughput screening of compounds. Examples of such methods are described in U.S. Pat. No. 5,429,921.

A variety of assays for pharmacological agents are provided, including, labeled in vitro protein binding assays, $Ca^{+2}$ influx assays, etc. For example, protein binding screens are used to rapidly examine the binding of candidate pharmacological agents to a human N-type calcium channel h$\alpha_{1B+SFVG}$ subunit. The candidate pharmacological agents can be derived from, for example, combinatorial peptide libraries. Convenient reagents for such assays are known in the art. An exemplary cell-based assay of calcium influx involves contacting a neuronal cell having a human N-type calcium channel h$\alpha_{1B+SFVG}$ subunit with a candidate pharmacological agent under conditions whereby the influx of calcium can be stimulated by application of a voltage to the test system, i.e., by membrane depolarization. Specific conditions are well known in the art and are described in Lin et al., *Neuron* 18:153–166, 1997, and in U.S. Pat. No. 5,429, 921. A reduction in the voltage gated calcium influx in the presence of the candidate pharmacological agent indicates that the candidate pharmacological agent reduces the induction of calcium influx of human N-type calcium channel h$\alpha_{1B+SFVG}$ subunit in response to the voltage stimulus. An increase in the voltage gated calcium influx in the presence of the candidate pharmacological agent indicates that the candidate pharmacological agent increases the induction of calcium influx of human N-type calcium channel h$\alpha_{1B+SFVG}$ subunit in response to the voltage stimulus. Methods for determining changes in the intracellular calcium concentration are known in the art and are addressed elsewhere herein.

Human N-type calcium channel h$\alpha_{1B+SFVG}$ subunit used in the methods of the invention can be added to an assay mixture as an isolated polypeptide (where binding of a candidate pharmaceutical agent is to be measured) or as a cell or other membrane-encapsulated space which includes a human N-type calcium channel h$\alpha_{1B+SFVG}$ subunit polypeptide. In the latter assay configuration, the cell or other membrane-encapsulated space can contain the human N-type calcium chaimel h$\alpha_{1B+SFVG}$ subunit as a preloaded polypeptide or as a nucleic acid (e.g. a cell transfected with an expression vector containing a human N-type calcium channel h$\alpha_{1B+SFVG}$ subunit). In the assays described herein, the human N-type calcium channel h$\alpha_{1B+SFVG}$ subunit polypeptide can be produced recombinantly, or isolated from biological extracts, but preferably is synthesized in vitro. Human N-type calcium channel h$\alpha_{1B+SFVG}$ subunit polypeptides encompass chimeric proteins comprising a fusion of a human N-type calcium channel h$\alpha_{1B+SFVG}$ subunit polypeptide with another polypeptide, e.g., a polypeptide capable of providing or enhancing protein-protein binding, or enhancing stability of the human N-type calcium channel h$\alpha_{1B+SFVG}$ subunit polypeptide under assay conditions. A polypeptide fused to a human N-type calcium channel h$\alpha_{1B+SFVG}$ subunit polypeptide or fragment thereof may also provide means of readily detecting the fusion protein, e.g., by immunological recognition or by fluorescent labeling.

The assay mixture also comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate pharmacological agents are small organic compounds, i.e., those having a molecular weight of more than 50 yet less than about 2500. Candidate agents comprise functional chemical groups necessary for structural interactions with polypeptides, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids having non-natural bonds or subunits are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known pharmacological agents may be subjected to directed or random chemical modifications such as acylation, alkylation, esterification, amidification, etc. to produce structural analogs of the agents. Candidate agents can be selected randomly or can be based on existing compounds which bind to and/or modulate the function of N-type calcium channels. For example, compounds which are known to inhibit N-type calcium channels include fluspirilene, ziconotide (SNX-111), the (ω-conotoxin peptides GVIA (SEQ ID NO: 11) and MVIIA (SEQ ID NO: 12), as well as small organic molecule calcium channel inhibitors, such as fluspirilene, NNC 09-0026(−)-trans-1-butyl-4-(4-dimethylaminophenyl)-3-[(4-trifluoromethyl-phenoxy)methyl] piperidinedihydrochloride); SB 201823-A (4-[2-(3,4-dichlorophenoxy)ethyl]-1-pentyl piperidinehydrochloride); NS 649 (2-amino-1-(2,5-dimethoxyphenyl)-5-trifluoromethyl benzimidazole); CNS 1237 (N-acenaphthyl-N'-4-methoxynaphth-1-yl guanidine) and riluzole. Therefore, a source of candidate agents are libraries of molecules based on the foregoing N-type calcium channel inhibitors, in which the structure of the inhibitor is changed at one or more positions of the molecule to contain more or fewer chemical moieties or different chemical moieties. The structural changes made to the molecules in creating the libraries of analog inhibitors can be directed, random, or a combination of both directed and random substitutions and/or additions. One of ordinary skill in the art in the preparation of combinatorial libraries can readily prepare such libraries based on the existing N-type calcium channel inhibitors.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

The mixture of the foregoing assay materials is incubated under conditions whereby, but for the presence of the candidate pharmacological agent, the human N-type calcium channel $h\alpha_{1B+SFVG}$ subunit transduces a control amount of voltage gated calcium influx. For determining the binding of a candidate pharmaceutical agent to a human N-type calcium channel $h\alpha_{1B+SFVG}$ subunit, the mixture is incubated under conditions which permit binding. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 1 minute and 10 hours.

After incubation, the level of voltage gated calcium influx or the level of specific binding between the human N-type calcium channel $h\alpha_{1B+SFVG}$ subunit polypeptide and the candidate pharmaceutical agent is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximize signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as a calcium influx assay. The calcium influx resulting from voltage stimulus of the human N-type calcium channel $h\alpha_{1B+SFVG}$ subunit polypeptide typically alters a directly or indirectly detectable product, e.g., a calcium sensitive molecule such as fura-2-AM. For cell free binding assays, one of the components usually comprises, or is coupled to, a detectable label. A wide variety of labels can be used, such as those that provide direct detection (e.g., radioactivity, luminescence, optical or electron density, etc). or indirect detection (e.g., epitope tag such as the FLAG epitope, enzyme tag such as horseradish peroxidase, etc.). The label may be bound to a human N-type calcium channel $h\alpha_{1B+SFVG}$ subunit polypeptide or the candidate pharmacological agent.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

The invention will be more fully understood by reference to the following examples. These examples, however, are merely intended to illustrate the embodiments of the invention and are not to be construed to limit the scope of the invention.

EXAMPLES

Example 1

Analysis of Human Brain N-type Calcium Channel Splice Variants

The abundance of splice variants of N-type calcium channels in human brain was determined using polymerase chain reaction analysis and RNase protection assays as described in Lin et al. (*Neuron* 18:153–166, 1997). Human N-type calcium channel $\alpha_{1B}$ subunit clones were sequenced by standard methods of nucleotide sequencing and it was determined that one type of clone had a 12 nucleotide insert (SEQ ID NO:1) as compared to previously published human N-type calcium channel $\alpha_{1B}$ subunit sequences. The present human N-type calcium channel $\alpha_{1B}$ subunit nucleic acid molecule (designated $h\alpha_{1B+SFVG}$) corresponds to the published nucleotide sequence for human N-type calcium channel $\alpha_{1B}$ subunits with the 12 nucleotide insert located after nucleotide 3855 (as numbered in Williams et al., *Science* 257:389–395, 1992). The nucleotide sequence of SEQ ID NO:1 supplies the third base of the codon encoding Ser1237, three new codons (Ser1238, Phe12239 and Val1240), and the first two bases of codon Gly1241, as shown in SEQ ID NO:3: tcG AGC TTC GTG GGa (insert in caps). This insert thus encodes a four amino acid insert in the protein which is similar to, but surprisingly is not identical to, amino acids 1236–1239 of a rat N-type calcium channel $\alpha_{1B}$ subunit (SEQ ID NO:10, GenBank accession number M92905). The human N-type calcium channel $h\alpha_{1B+SFVG}$ subunit was found to make up a significant portion of the N-type calcium channel $\alpha_{1B}$ subunits mRNA in human brain. It was also determined that the $h\alpha_{1B+SFVG}$ subunit was differentially distributed in different parts of the brain, e.g. in certain portions of the brain $h\alpha_{1B+SFVG}$ was more highly expressed than in other portions of the brain.

Example 2

Construction of Human N-type Calcium Channel $h\alpha_{1B+SFVG}$ Subunit Nucleic Acids The human N-type calcium channel $h\alpha_{1B+SFVG}$ subunit containing the SFVG insert is constructed according to standard procedures described in, e.g., *Current Protocols in Molecular Biology* (F. M. Ausubel, et al., eds., John Wiley & Sons, Inc., New York), using PCR primers which contain the nucleotides encoding SFVG (e.g., SEQ ID NO:1) to amplify the published human N-type calcium channel $\alpha_{1B}$ subunit nucleic acid. Fragments generated by PCR are then assembled by ligation to prepare a complete cDNA encoding the human $h\alpha_{1B+SFVG}$ subunit.

Example 3

Function of the Human N-type Calcium Channel $h\alpha_{1B+SFVG}$ Subunit

The voltage gated calcium channel activity of the human N-type calcium channel $h\alpha_{1B+SFVG}$ subunit is tested using to the methods described in Lin et al. (1997) for a rat N-type calcium channel subunit, and as described in Example 4 below.

Example 4

Activation Differences in Rat N-type Calcium Channels±the ET Exon

Functional Assessment of the Calcium Channel $\alpha_{1B}$ cDNA Constructs

The functional properties of all calcium (Ca) channel $\alpha_{1B}$ cDNA constructs described in this paper were assessed in the Xenopus oocyte expression system. All methods and procedures were essentially the same as described in Lin et al. (1997). cRNAs were in vitro transcribed using the mMESSAGE mMACHINE kit (Ambion) from the various $\alpha_{1B}$ cDNA constructs subcloned into the Xenopus β-globin expression vector (pBSTA; Goldin & Sumikawa et al., *Methods Enzymol.* 207:279–297, 1992). 46 nl of a 750 ng/μl cRNA solution was injected into defolliculated oocytes using a precision nanoinjector (Drummond). N-type Ca channel currents were recorded 6–7 days after injection. At least 15 minutes prior to recording, oocytes were injected with 46 nl of a 50 mM solution of BAPTA (1,2-bis(o-aminophenoxy)ethane-N,N,N',N'-tetraacetate). This we have found critical to minimize activation of an endogenous $Ca^{2+}$-activated $Cl^-$ current, even when $Ba^{2+}$ is the charge carrier (Lin et al., 1997). Cells exhibiting slowly deactivating tail currents, indicative of the presence of $Ba^{2+}$-dependent activation of the Ca-activated $Cl^-$ current, were excluded from the analysis.

N-type $Ca^{2+}$ channel currents were recorded from oocytes using the two microelectrode voltage-clamp recording technique (Warner amplifier; OC-725b). A virtual ground circuit eliminated the need for series resistance compensation when recording large currents. Micropipettes of 0.8–1.5MΩ and 0.3–0.5MΩ resistance when filled with 3 M KCl were used for the voltage and current recording electrodes, respectively. Oocytes expressing $Ca^{2+}$ channel currents usually had resting membrane potentials between −40 and −50 mV when impaled with two electrodes. A grounded metal shield was placed between the two electrodes to increase the settling time of the clamp. Recording solutions contained 5 mM $BaCl_2$, 85 mM tetraethylammonium, 5 mM KCl, and 5 mM HEPES (pH adjusted to 7.4 with methanesulfonic acid). The recording temperature was between 19° C. and 22° C.

The properties of each mutant construct were assessed by expressing it together with appropriate controls (ΔET $\alpha_{1B}$ and +ET $\alpha_{1B}$). Each mutant was tested in three separate batches of oocytes and within each batch, recordings were made from at least six oocytes for each mutant construct and control. Recordings from the oocytes expressing the various Ca channel $\alpha_{1B}$ constructs were randomized throughout the data collection period.

Data Analysis.

Data were acquired on-line and leak subtracted using a P/4 protocol (PClamp V6.0; Axon Inst.). Voltage-steps were applied every 10–30 seconds depending on the duration of the step, from a holding potential of −80 mV. Ca channel currents recorded under these conditions showed little run-down over the duration of the recordings. Three sets of current voltage-relationships were obtained from each cell using step depolarizations of 26.3 ms, 650 ms and 2.6 s in duration and digitized at 25 kHz, 10 kHz and 250 Hz, respectively. Exponential curves (activation and inactivation) were fit to the data using curve fitting routines in PClamp (Axon Instr.) and Origin (Microcal). Inactivation time constants in the range of 70–800 msec were estimated from currents evoked by the longest depolarization (2.6 s). Activation time constants were best resolved from currents evoked by the shortest depolarizations (26.3 ms; sampled at 25 kHz).

Modeling Ca Entry.

A one-compartment cell model employing standard compartmental modeling techniques in NEURON (Hines & Carnevale, *Neural Comput*. 9:1179–1209, 1997) was used to predict the amount of Ca entering a neuron expressing either $rn\alpha_{1B-b}$ or $rn\alpha_{1B-b}$ N-type Ca channel currents. The cell had a total membrane area of 1250 μm², 0.75 μF/cm² specific membrane capacitance and 30 kΩcm² specific membrane resistance. For action potential simulation a fast sodium conductance ($g_{Na}$) and a delayed rectifying potassium conductance ($g_{K,DR}$) were included (Mainen & Sejnowski, *Science* 268:1503–1506, 1995) each with densities of 300 pS/μm². $Ca^2$ influx was mediated by a fast calcium conductance ($g_{Ca}$; Yamada et al., Multiple channels and calcium dynamics. In *Methods in Neuronal Modeling*. Koch, C. & Segev, I., Eds. pp 97–134, 1989) with a density of 1 pS/μm². Resultant currents were calculated using conventional Hodgkin-Huxley kinetic schemes according to the formulae given below. The resting membrane potential was set at −70 mV and Na and K current reversal potentials at +50 mV and −75 mV, respectively. The calcium channel was computed using the Goldman-Hodgkin-Katz equation. Extracellular Ca concentration was 2.5 mM and the intracellular Ca concentration computed using entry via $I_{Ca}$ and removal via a first order pump $d[Ca^{2+}]_i/dt=(-1\times10^5 \cdot I_{Ca}/2F)-([Ca^{2+}]_i-[Ca^{2+}]_\infty)/\tau_R$, where $[Ca^{2+}]_\infty=10$ nM and $\tau_R=80$ ms. The time constants and maximal conductances were developed at room temperature and were therefore scaled to 37° C. using a $Q_{10}$ of 2.3. Formulae used for calculation of various currents were as follows:

Sodium current ($I_{na}$), m³·h: $\alpha_{m,Na}=0.82 \cdot (v+25)/(1-e^{(v+25)/9})$; $\beta_{m,Na}=-0.124 \cdot (v+25)/(1-e^{-(v+25)/9})$ $\alpha_{h,Na}=0.0024 \cdot (v+40)/(1-e^{-(v+40)/5})$; $\beta_{h,Na}=-0.0091 \cdot (v+65)/(1-e^{-(v+65)/5})$; $h_{\infty,Na}=1/(1-e^{-(v+55/6.2)})$ Delayed rectifier ($I_{K(DR)}$), m:$\alpha_{m,K(DR)}=0.02 \cdot (v-25)/(1-e^{-(v+25)/9})$; $\beta m, K(DR)=0.002 \cdot (v-25)/(1-e^{(v+25)/9})$ High threshold, N-type calcium current ($I_{ca}$), m·h: $m_{\infty, Ca}=1/(1+e^{-(v-3)/8})$; $\tau_{m, Ca}=7.8/(e^{(v+6)/16})$; $h_{Ca}=K/(K+[Ca^{2+}]_i)$ with K=0.01 mM.

The brain-dominant form, $rn\alpha_{1B-d}$, was then modeled by shifting the voltage-dependence of the N-type Ca channel conductance activation variable ($m_{\infty, Ca}$) by −7 mV, and decreasing the activation time constant ($\tau_{m, Ca}$) by 33% (Lin et al., 1997 and see FIG. 1A).

Ribonuclease Protection Assay.

The procedures are essentially the same as those described in Lin et al. (1997). Total RNA was purified from various neuronal tissue of adult rats using a guanidium thiocyanate and phenol-chloroform extraction protocol (adapted from Chomczynski & Sacchi, *Anal. Biochem.* 162:156–159, 1987). $^{32}$P-labeled antisense RNA probes overlapping ET (nt 4379–4836) in $rn\alpha_{1B-b}$ and NP (nt4605–4930) in $rb\alpha_{1A}$ (Starr et al., *Proc. Natl. Acad. Sci. USA*, 88:5621–5625, 1991) were constructed from linearized plasmids (pGEM-T vector) containing appropriate RT-PCR-derived sub-clones using the Maxi-script kit (Ambion). Probes were gel purified and stored as ethanol precipitates. 1 μg of RNA purified from sympathetic or sensory ganglia or 5 μg of RNA isolated from various CNS tissues were precipitated with $2\times10^5$ cpm of probe and resuspended in 30 μl hybridization buffer containing: 60% formamide; 0.4 M NaCl; 10 mM EDTA and 40 mM PIPES at pH 6.4. Samples were denatured at 85° C. and allowed to hybridize overnight at 60° C. The samples were then digested in a 350 μl reaction mix containing: 0.3 M NaCl, 5 mM EDTA, 3.5 μl of the RNase Cocktail (Ambion) and 10 mM Tris at pH 7.5, then treated with proteinase K, extracted and precipitated with 10 μg of tRNA as carrier. After resuspension in 30 μl formamide loading buffer, the samples wee denatured and separated on a 5% polyacrylamide gel. After exposure to a phosphor imaging plate to quantity relative band intensities (Fuji BAS 1000), the gel was subsequently exposed to film with an intensifying screen for 4–5 days at –80° C.

Site-directed Mutagenesis

A recombinant PCR-based technique was used to introduce mutations (QT, EA, AT, AA, NP) at the ET site in the IVS3-S4 linker of $\alpha_{1B-b}$. A pair of primers 5'-attcttgtggtcatcgccttgag (Bup 3460; SEQ ID NO: 13) and 5'-gacaggcctccaggagcttggtg (Bdw 5623; SEQ ID NO: 14) flanked a region of the clone that contained two restriction sites RsrII (nt3510) and BglII (nt5465) located on either side of ET (nt4674). A second primer pair contained the desired mutation and directly overlapped the ET site (Bdwmut and Bupmut; see below). Two separate PCRs were performed with Bup 3460 and Bdwmut, and Bupmut and Bdw 5623. The PCR product then served as template for a second round of PCR using Bup 3460 and Bdw 5623 generating the final mutant PCR fragment that was subsequently subcloned into $rn\alpha_{1B-b}$ at the Rsr II and Bgl II sites. Mutants were screened by restriction digest and confirmed by DNA sequencing. All PCR was performed using Expand High Fidelity (Boehringer Mannheim). The mutagenesis primers used were as follows:

ET/AT: Bupmut 5'-gaattacgGCAACGaacaacttcatc-3': SEQ ID NO: 15
Bdwmut 5'-aagttgttCGTTTCcgcaatctccg-3'; SEQ ID NO: 16
ET/QT: Bupmut 5'-gagattgcgCAGACGaacaacttcatc-3'; SEQ ID NO: 17
Bdwmut 5'-aagttgttCGTCTGcgcaatctccg-3'; SEQ ID NO: 18
ET/EA: Bupmut 5'-oagattgcgGAAGCTaacaacttcatc-3'; SEQ ID NO: 19
Bdwmut 5'-aagttgttAGCTTCcgcaatctccg-3'; SEQ ID NO: 20
ET/AA: Bupmut 5'-cagattgccGCAGCTaacaacttcatc-3'; SEQ ID NO: 21
Bdwmut 5'-aagttgttAGCTGCcgcaatctccg-3'; SEQ ID NO: 22
ET/NP: Bupmut 5'-gagattgcgAACCCTaacaacttcatc-3'; SEQ ID NO: 23
Bdwmut 5'-aagttgttAGGGTTcgcaatctccg-3'; SEQ ID NO: 24

Genomic Analysis

The IVS3-S4 region of the rat $\alpha_{1B}$ and $\alpha_{1A}$ genes were analyzed by genomic PCR. Primer paris were directed to the IVS3 and IVS4 membrane spanning regions that were presumed to reside in the 5' and 3' exons flanking the ET and NP insertions of the $\alpha_{1B}$ and $\alpha_{1A}$ genes, respectively. PCR was performed in a 50 μl reaction mix containing 250 ng rat liver genomic DNA, 250 μM of each nucleotide and 0.4 μM of each primer. After a pre-incubation for 15 min at 92° C., 0.75 μl enzyme mix was added to start the amplification. The resultant gDNA products were gel purified, cloned into pGEM-T (Promega) and sequenced. The $\alpha_{1B}$ primers generated two bands of ~11 kb and ~900 bases. The 11 kb band was derived from the $\alpha_{1B}$ gene and contained the desired ET encoding exon in IVS3-S4. The 900 base product resulted from amplification of the equivalent site in the $\alpha_{1E}$ gene that contained a relatively short ~700 bp intron and no intervening exon. The $\alpha_{1A}$ primers generated a single 9 kb PCR product that was confirmed to be derived from the $\alpha_{1A}$ gene by DNA sequencing (Yale University sequencing facility). Primers were as follows:

$\alpha_{1A}$: Aup4737 5'-tgcctggaacatcttcgactttgtga; SEQ ID NO: 25
Adw4876 5'-cagaggagaatgcggatggtgtaacc; SEQ ID NO: 26
$\alpha_{1B}$: Bup4599 5'-cagagatgcctggaacgtctttgac; SEQ ID NO: 27
Bdw4744 5'-ataacaagatgcggatggtctagcc; SEQ ID NO: 28

Alternative Splicing in the Putative S3-S4 Extracellular Linkers Affects Channel Activation but not Inactivation Kinetics In a previous study it was shown that $rn\alpha_{1B-b}$ (ΔSFMG/+ET) and $rn\alpha_{1B-d}$ (+SFMG/ΔET) N-type currents differ with respect to their activation kinetics when expressed in Xenopus oocytes (compare Δ/+ and +/Δ in FIGS. 1A, B; see also Lin et al., 1997). Inactivation kinetics of the two splice variants have not, however, been compared (Lin et al., 1997). In the present study depolarizations of durations of between 26 ms and 2.6 s were employed to permit the resolution of both the time course of Ca channel activation and inactivation. Rat N-type calcium channel subunits ($rn\alpha_{1B-b}$ [Δ/+] and $rn\alpha_{1B-d}$ [+/Δ]) were expressed in Xenopus oocytes and resulting N-type Ca channel currents recorded using 5 mM Ba as the charge carrier (FIG. 1). FIG. 1A shows the averaged, normalized Ca channel current induced by the expression in Xenopus oocytes of four different $\alpha_{1B}$ constructs. Currents were evoked by step depolarizations to 0 mV from a holding potential of –80 mV. Each trace represents the average, normalized current calculated from at least 6 oocytes. SFMG-containing clones are distinguished from SFMG-lacking clones by thin and thick lines and arrows, respectively. FIG. 1B shows a plot of average activation time constants (nat. log) at different test potentials (between –20 and +10 mV) for clones +/+ (□), Δ/+ (●), +/Δ (○) and Δ/Δ (■). The presence of SFMG in domain IIIS3-S4 did not affect the rate of channel activation. There was no significant difference in $\tau_{activ}$ between clones +/+ and Δ/+ or between clones +/Δ and Δ/Δ (p>0.1 at all potentials between –20 mV and +10 mV). The presence of ET in domain IVS3-S4 slowed channel activation kinetics. $\tau_{activ}$ values for clones +/+ and Δ/+ were significantly slower compared to +/Δ and Δ/Δ, at all test potentials between –20 mV and +10 mV (p<0.05).

N-type Ca channel currents evoked by depolarization to 0 mV or higher, inactivated with a bi-exponential time course ($\tau_{fast}$ 100–150 ms and $\tau_{slow}$ 700–800 ms). The inactivation time constants of the cloned channels expressed in Xenopus oocytes ($rn\alpha_{1B-b}$, Δ/+ and $rn\alpha_{1B-d}$, +/Δ) were weakly voltage-dependent consistent with studies of native N-type Ca channels of bullfrog sympathetic neurons (Jones & Marks, 1989). The fast and slow inactivation time constants of $rn\alpha_{1B-b}$ band $rn\alpha_{1B-d}$ currents evoked by step depolarizations to between 0 mV and +30 mV were not significantly different. In contrast, the rates of channel activation of the two variants in the same cells were significantly different (FIGS. 1A,B). On the basis of these observations it was concluded that alternative splicing in domains IIIS3-S4 and IVS3-S4 of the $\alpha_{1B}$-subunit altered the time course of N-type Ca channel activation but had no effect on inactivation kinetics. These findings are consistent with the close proximity of the S3-S4 linkers to their respective S4 helices that are the putative voltage sensors of the 6 transmembrane family of voltage-gated ion channels. In contrast, the domains of the Ca channels $\alpha_{1B}$ subunit implicated in voltage-dependent inactivation of N-type Ca channels (IS6 and flanking putative extracellular and intracellular linkers; Zhang et al., *Nature* 372:97–100, 1994) are likely to be more distant from the S3-S4 linker splice sites.

The Observed Differences in the Properties of $rn\alpha_{1B-b}$ and $rn\alpha_{1B-b}$ Currents are of Sufficient Magnitude to Impact Action Potential-induced Ca Entry.

Figure 2:
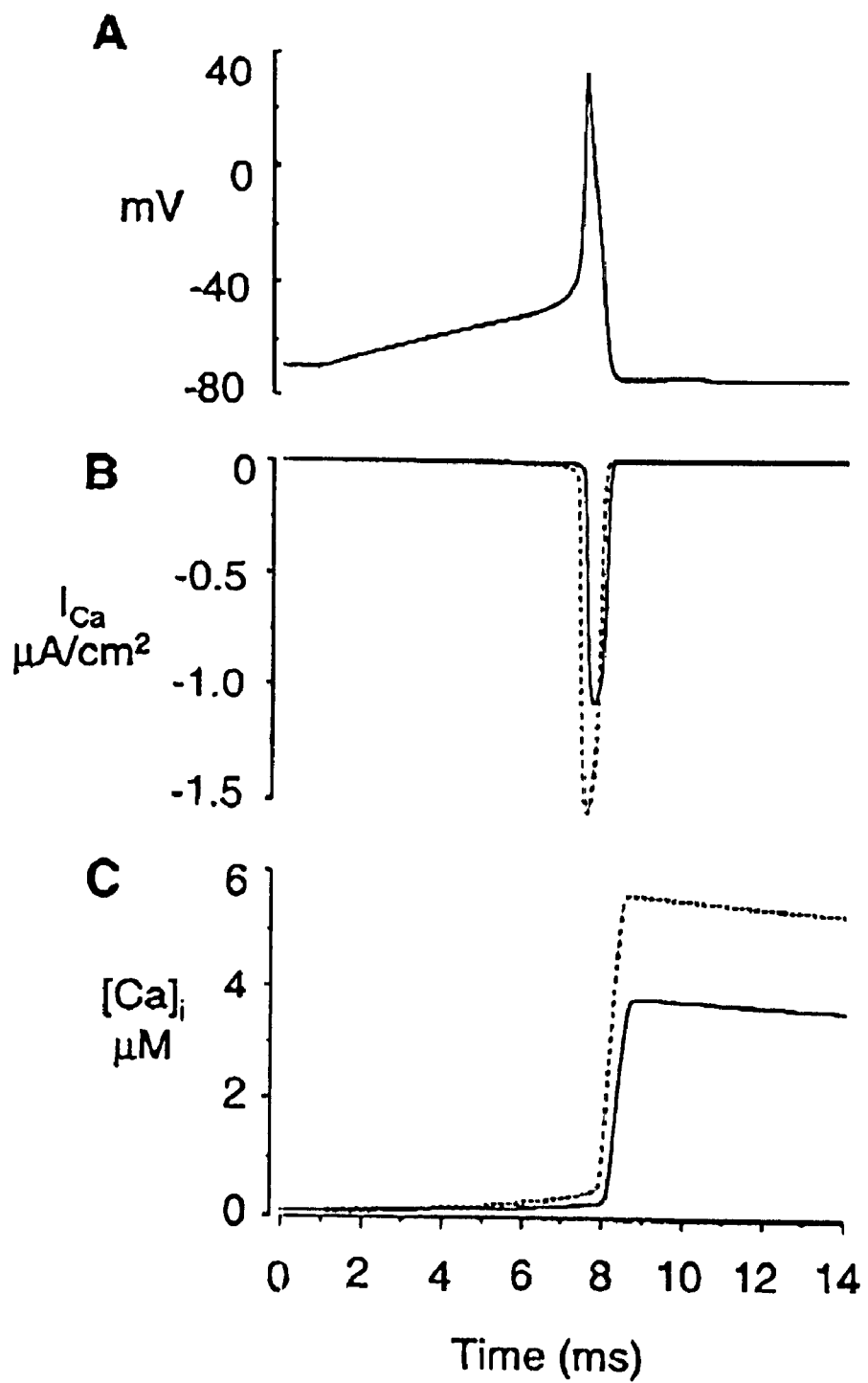
FIGS. 2A–C, show the impact of alternative splicing in the S3–S4 linkers of the α$_{1B}$ subunit on action potential-dependent Ca influx in a model neuron.

An assumption that motivates the present study is that the differences in the kinetics and voltage-dependence of activation of $rn\alpha_{1B-b}$ and $rn\alpha_{1B-d}$ N-type Ca channel currents are sufficient to influence the magnitude and time course of voltage-dependent calcium entry in native cells. A direct test of this hypothesis, however, is complicated by the inability to manipulate selectively the expression or activity of individual splice variants in their native environment. To date no isoform-specific pharmacological tools or antibodies to target Ca channel $\alpha_{1B}$, S3-S4 splice variants exist. Therefore, the available information was used to estimate the relative effectiveness of $rn\alpha_{1B-b}$ and $rn\alpha_{1B-d}$ N-type currents to support action potential-induced Ca influx in a model neuron (Hines & Carnevale, 1997). A one-compartment model was used to predict the time course and magnitude of calcium entry in a neuron during action potential-induced depolarization. Simulated action potentials with time courses similar to those recorded in native sympathetic neurons (Yamada et al., 1989; FIG. 2A) were used to trigger voltage-dependent Ca influx in model neurons (Na, K and Ca current densities of 300, 300 and 1 pS/μF, respectively) expressing either $rn\alpha_{1B-b}$ or $rn\alpha_{1B-d}$ N-type Ca channel currents. A simulated action potential was evoked by a 10 ms, 40 pA current step (FIG. 2A); a comparison of the resultant N-type channel current (FIG. 2B) and time course of intracellular calcium concentration (FIG. 2C) expected in a model neuron expressing either $rn\alpha_{1B-b}$ (Δ/+; solid line) or $rn\alpha_{1B-d}$ (+/Δ; dashed line)-type channels is shown. A shift in the voltage-dependence of the N-type Ca channel conductance activation variable ($M_{\infty, Ca}$) by −7 mV, and a decrease in the activation time constant ($\tau_{m, Ca, by}$ 33% expected for $rn\alpha_{1B-d}$ (Lin et al., 1997; and see FIG. 1A), resulted in a total increase in charge transfer and peak intracellular Ca concentration of 49% and 48%, respectively. A −50% increase in the total charge transfer (FIG. 2B) and peak intracellular Ca concentration (FIG. 2C) is predicted during an action potential in a neuron expressing $rn\alpha_{1B-d}$-type Ca channels (dashed line) relative to $rn\alpha_{1B-b}$ (solid line). All other factors being constant, the functional differences between $rn\alpha_{1B-b}$ and $rn\alpha_{1B-d}$ N-type Ca channel currents would be expected to significantly impact the amount of calcium that enters a neuron during action potential-dependent excitation.

Splicing of ET in Domain IVS3-S4 Underlies the Major Functional Difference Between $rn\alpha_{1B-b}$ and $rn\alpha_{1B-d}$ $rn\alpha_{1B-b}$ and $rn\alpha_{1B-d}$ differ in composition by 6 amino acids located in two distinct regions of the Ca channel $\alpha_{1B}$ subunit (SFMG in domain IIIS3-S4 and ET in domain IVS3-S4). To separate the relative contribution of SFMG in domain III S3-S4 and ET in domain IVS3-S4 to the different gating kinetics observed between $rn\alpha_{1B-b}$ (ΔSFMG/+ET) and $rn\alpha_{1B-d}$ (+SFMG/ΔET) two additional clones, +/+ and Δ/Δ were constructed and the functional properties of all four clones were compared. FIG. 1 (A and B) demonstrates that the presence of the dipeptide sequence ET in domain IVS3-S4 is directly correlated with the altered activation kinetics of $rn\alpha_{1B-b}$ currents compared to $rn\alpha_{1B-d}$. Activation time constants measured from N-type Ca channel currents in oocytes expressing clone Δ/+ ($rn\alpha_{1B-b}$) and +/+ were indistinguishable and 1.5 fold slower on average than those induced by the expression of clones +/Δ ($rn\alpha_{1B-d}$) and Δ/Δ (FIGS. 1A,B). The presence of ET in domain IVS3-S4 also influenced the voltage-dependence of channel activation. A comparison of the mid-points of the rising phase of the peak current-voltage plots ($V_{1/2}$) generated for the two ET containing clones, Δ/+ ($rn\alpha_{1B}$; −7.8±0.6 mV, n=6) and +/+ (−9.7±1.0 mV, n=6) shows that they are significantly different from each other (p>0.05, students' t-test). Likewise, $V_{1/2}$ values estimated from two ET-lacking constructs, +/Δ ($rn\alpha_{1B-d}$; −15.4±0.4 mV, n=7) and Δ/Δ (−13.4±0.7, n=6), were not significantly different from each other (p>0.05) and activated at potentials that were, on average, 6 mV more negative compared to ET-containing clones Δ/+ and +/+. While the presence of ET in domain IVS3-S4 dominates in regulating the voltage-dependence of activation, the analysis does reveal a small contribution of SFMG. SFMG-containing clones (+/Δ and +/+) activated at potentials that were 2 mV hyperpolarized compared to those that lacked SFMG (Δ/+ and Δ/Δ). A 2 mV shift in the voltage-dependence of activation was not significant at the 5% level, in a comparison of $V_{1/2}$ values from clones Δ/+ and +/+, but did reach significance in a comparison of +/Δ and Δ/Δ (p<0.025, students t-test).

The pattern of Expression of ET-containing Ca Channel $\alpha_{1B}$ mRNA in Different Regions of the Nervous System FIG. 1 indicates that alternative splicing of ET within domain IVS3-S4 of the Ca channel $\alpha_{1B}$-subunit accounts for the major functional differences between $rn\alpha_{1B-b}$ and $rn\alpha_{1B-A}$. This prompted a systemic analysis of the expression pattern of the six bases in $\alpha_{1B}$ mRNA that encoded ET (gaa acg). It was previously shown that ET-containing $\alpha_{1B}$ (+ET $\alpha_{1B}$) mRNA was in very low abundance in total rat brain extracts (Lin et al., 1997). To determine whether ET-lacking $\alpha_{1B}$ (ΔET $\alpha_{1B}$) mRNA dominated throughout the central nervous system RNA isolated from spinal cord, cerebellum, cortex, hippocampus, hypothalamus, medulla and thalamus of adult rats was analyzed by ribonuclease protection assay. In all regions tested >90% of the $\alpha_{1B}$ mRNA expressed in the central nervous system lacked the ET encoding sequence. In contrast, in sympathetic and sensory ganglia the majority of $\alpha_{1B}$ mRNA contained the ET encoding sequence. Together these findings suggest that +ET $\alpha_{1B}$ subunits are primarily restricted to neurons of the peripheral nervous system. Consistent with this RNA isolated from human brain and trigeminal ganglia was analyzed and analogous patterns of expression were observed: low levels of +ET $\alpha_{1B}$ mRNA in brain and high levels (>90%) in ganglia.

Site-directed Mutagenesis within IVS3-S4

Figure 3:
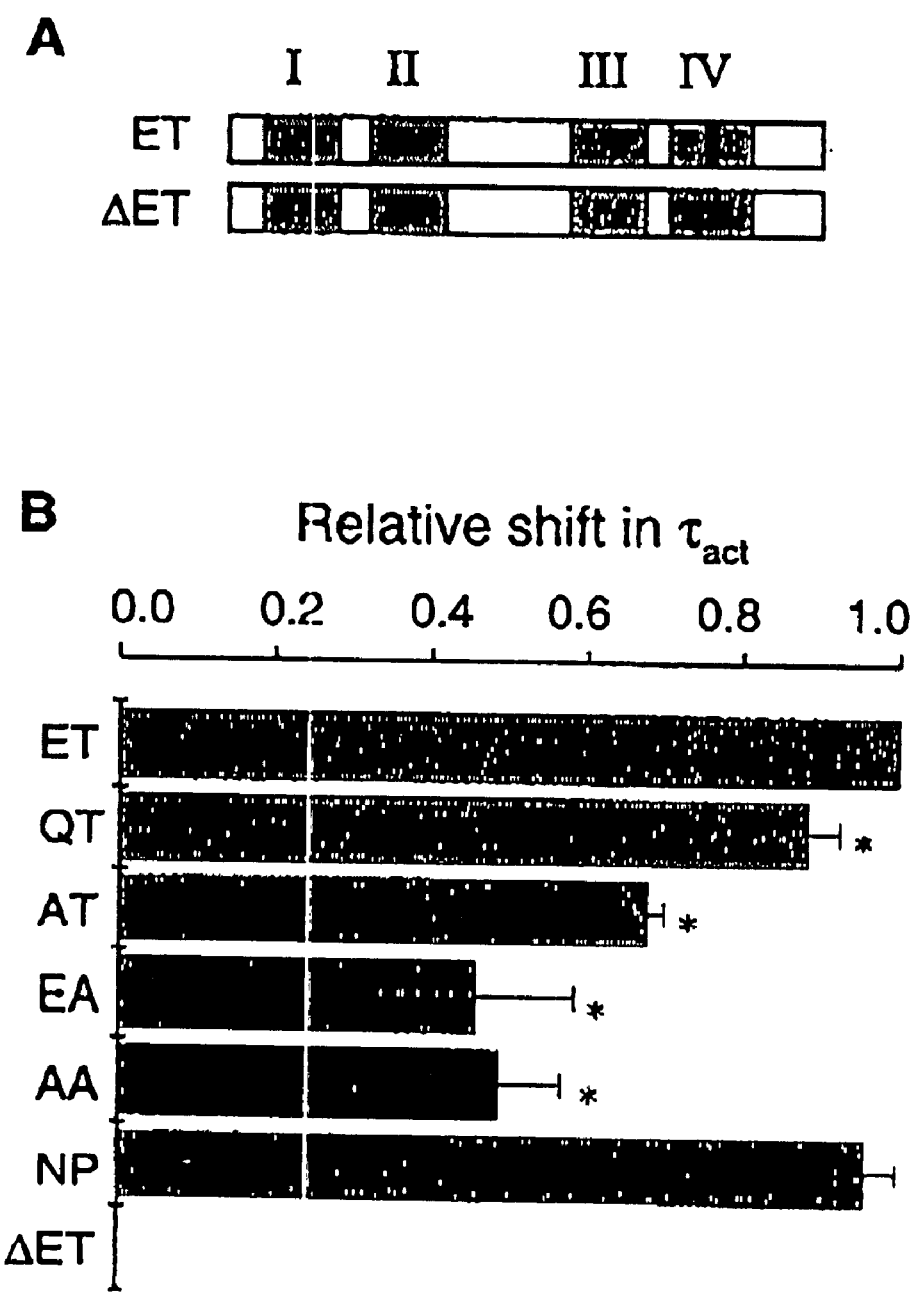
FIGS. 3A & B, show the results of a functional analysis of site-directed mutagenesis of ET splice site in domain IVS3-S4 of the α$_{1B}$ subunit.

Having shown that alternative splicing of the ET encoding sequence in the IVS3-S4 linker of $\alpha_{1B}$ has a significant effect on the kinetics and voltage-dependence of N-type Ca channel gating, the use of site-directed mutagenesis was employed to determine the relative importance of each amino acid, glutamate and threonine. A series of mutants in which ET was replaced with either QT, AT, EA, AA or NP were constructed (FIG. 3) from clone Δ/+ ($\alpha_{1B-b}$) which served as the background structure. The mutant constructs were then expressed in Xenopus oocytes and their properties compared to clones +ET (100% slow; FIG. 3) and ΔET (100% fast; FIG. 3). All mutants expressed equally well in the Xenopus oocyte expression system.

The role of the glutamate in domain IVS3-S4 was of major interest because it should be negatively charged at neutral pH and consequently might influence the gating machinery of the channel via electrostatic interactions. FIG. 3, however, shows that replacing glutamate with glutamine resulted in a channel that activated only slightly faster than +ET $\alpha_{1B}$ (FIG. 3 QT). Substituting alanine for glutamate (AT) decreased $\tau_{act}$ but, consistent with the QT mutant, suggests that the presence of a negative charge in IVS3-S4 (glu) does not underlie the slow gating kinetics of the +ET $\alpha_{1B}$ variant. Similarly, alanine substitution of either threonine alone (EA) or together with glutamate (AA) generated channels with activation kinetics that were intermediate between +ET $\alpha_{1B}$ and $\Delta$ET $\alpha_{1B}$ clones. Together, these results suggest that the presence of both glutamate and threonine in the IVS3-S4 linker is necessary to reconstitute the relatively slow channel opening rates characteristic of N-type Ca channel $\alpha_{1B}$-subunits that dominate in sensory and sympathetic ganglia.

Sequence comparisons of several cDNAs encoding $\alpha_{1B}$-subunits of other voltage-gated Ca channels suggests that alternative splicing in the IVS3-S4 linker could be a general mechanism for regulating voltage-dependent Ca channel gating. This has recently been demonstrated for $\alpha_{1A}$ (Sutton et al., *Soc. Neurosci. Abs.* 24:21, 1998), a Ca channel subunit that is closely related both structurally and functionally to the N-type Ca channel $\alpha_{1B}$ subunit. A comparison of the IVS3-S4 region of various mammalian $\alpha_{1A}$ cDNAs derived from kidney, pancreas and brain (see also Yu et al., *Proc. Natl. Acad Sci. USA* 89:10494–10498, 1992; Ligon et al., *J. Biol. Chem.* 273:13905–13911, 1998; Sutton et al., 1998) is consistent with alternative splicing of six bases encoding Asp Pro (NP) amino acids in this region. The distribution of +NP $\alpha_{1A}$ and $\Delta$NP $\alpha_{1A}$ mRNAs in different regions of the rat nervous system has not been quantified. Therefore RNase protection analysis was used to determine the expression pattern of the IVS3-S4 splice variants of $\alpha_{1A}$. Low levels of +NP $\alpha_{1A}$ mRNA were found in rat, spinal cord, striatum and thalamus, a pattern that parallels the low levels of +ET $\alpha_{1B}$ mRNA in the CNS. However, the pattern of NP expression in the cerebellum, cortex and hippocampus did not conform to this picture since mRNA isolated from these tissues contained a significant proportion of +NP $\alpha_{1A}$ mRNAs. In fact, in the hippocampus +NP $\alpha_{1A}$ mRNAs dominated (~60%). Consistent with the abundance of +ET $\alpha_{1B}$ mRNAs in peripheral tissue, the majority of $\alpha_{1A}$ mRNA in superior cervical and dorsal root ganglia contained the six bases encoding NP in domain IVS3-S4 of $\alpha_{1A}$. The absolute level of $\alpha_{1A}$ mRNA expressed in sympathetic neurons was very low as expected from the absence of P-type currents in recordings from rat sympathetic neurons (Mintz et al., 1992).

The high degree of sequence homology between $\alpha_{1B}$ and $\alpha_{1A}$ in the IVS3-S4 linker region together with the finding that a 6 base sequence is alternatively spliced at both these sites, suggested that ET and NP share a common functional role. To test this hypothesis the functional impact on N-type Ca channel currents of replacing ET in rn$\alpha_{1B-b}$ with NP was studied. FIG. 3 shows that the +NP $\alpha_{1B}$ mutant gives rise to N-type Ca channel currents in oocytes with gating kinetics indistinguishable from wild-type (i.e. +ET $\alpha_{1B}$). Activation time constants were estimated from currents induced by the expression of the various mutant $\alpha_{1B}$ constructs (QT, AT, EA, AA, NP) in oocytes and compared to clones ET and $\Delta$ET (A). Shifts in the activation time constants of the mutant channels, relative to clones ET and $\Delta$ET (100% slow) and AET (100% fast) are plotted (B). Each point represents data collected from at least 18 oocytes per mutant (each mutant was tested in three separate batches of oocytes and within each experiment at least 6 oocytes per mutant were analyzed). Values plotted are means±standard errors from the three data sets. The asterisk indicates a significant slowing of the activation time constant compared to clone ET ($P<0.05$).

ET is Encoded by a Six Base Exon in the IVS3-S4 Linker Region of the $\alpha_{1B}$ Gene The existence of an alternatively spliced exon in the IVS3-S4 region of the rat Ca channel $\alpha_{1B}$ gene has been hypothesized (Lin et al., 1997), but not yet confirmed. Genomic analysis was therefore undertaken to locate the splice junctions in the IVS3-S4 region of the $\alpha_{1B}$ gene and to pinpoint the precise location of the putative six-base, ET encoding exon. PCR amplification from rat genomic DNA using primers designed to hybridize to the transmembrane spanning S3 and S4 helices flanking IVS3-S4 in $\alpha_{1B}$ revealed the presence of a long ~10 kb stretch of intron sequence. DNA sequencing established the location of exon/intron and intron/exon boundaries and conserved ag-gt splice junction signature sequences immediately 5' and 3' to the putative ET insertion site. A six-base cassette exon encoding ET was located 8 kb into the 5' intron and establishes that ET-$\alpha_{1B}$ variants are generated by alternative splicing. The exon/intron structure in the IVS3-S4 linker region of the closely related rat $\alpha_{1A}$ gene was also determined. The rat $\alpha_{1A}$ gene also contained a long stretch of intron sequence (~8 kb) and ag-gt splice junctions at the 5' (gt) and 3' (at) ends of the intronic segment. The precise location of the NP encoding cassette exon in the rat $\alpha_{1A}$ gene has not been determined but conclude that it must reside within the 8 kb of intron sequence in the IVS3-S4 linker region. Tissue-specific alternative splicing of six base cassette exons in the IVS3-S4 linkers of both $\alpha_{1A}$ and $\alpha_{1B}$ explains the presence of splice variants of these subunits in the mammalian brain and underscores the high level of conservation between these two functionally related genes. The genomic structure of the more distantly related rat $\alpha_{1E}$ gene that encodes a pharmacoloically and functionally distinct class of Ca channel (Soong et al., *Science* 260:1133–1136, 1993) also was analyzed. The $\alpha_{1E}$ gene contains a ~700 bp intron in the IVS3-S4 linker region and no obvious intervening exon. The absence of an alternatively spliced cassette exon in the IVS3-S4 linker region of the $\alpha_{1E}$ gene is consistent with RNase protection analysis of $\alpha_{1E}$ mRNA from rat brain which revealed no evidence of sequence variations in this IVS3-S4 linker.

Each of the foregoing patents, patent applications and references is hereby incorporated by reference. While the invention has been described with respect to certain embodiments, it should be appreciated that many modifications and changes may be made by those of ordinary skill in the art without departing from the spirit of the invention. It is intended that such modification, changes and equivalents fall within the scope of the following claims.

What is claimed is:

1. An isolated human N-type calcium channel $h\alpha_{1B+SFVG}$ subunit polypeptide, wherein the polypeptide comprises the amino acid sequence of SEQ ID NO:4.

2. The isolated human N-type calcium channel $h\alpha_{1B+SFVG}$ subunit polypeptide of claim 1, wherein the polypeptide consists of the amino acid sequence of SEQ ID NO:4.

3. The isolated human N-type calcium channel $h\alpha_{1B+SFVG}$ subunit polypeptide of claim 1, wherein the polypeptide consists essentially of the amino acid sequence of SEQ ID NO:4.

4. A fragment of the isolated human N-type calcium channel $h\alpha_{1B+SFVG}$ subunit polypeptide of claim 1, which comprises the amino acid sequence of SEQ ID NO:2 and which retains the human N-type calcium channel $h\alpha_{1B+SFVG}$ subunit activity.

5. An isolated human calcium channel $h\alpha_{1B+SFVG}$ subunit polypeptide comprising SEQ ID NO:2 in an extracellular domain.

6. The isolated human calcium channel $\alpha_1$ subunit polypeptide of claim 5, wherein a portion of the extracellular domain, but not SEQ ID NO:2, is replaced by an extracellular domain from another $\alpha_1$ subunit.

* * * * *